United States Patent
Wang et al.

(10) Patent No.: US 10,443,026 B2
(45) Date of Patent: Oct. 15, 2019

(54) POLYGONAL SCAFFOLD AND MANUFACTURING METHOD THEREOF, AND PROTEIN MODULATOR AND MANUFACTURING METHOD THEREOF

(71) Applicant: NATIONAL TSING HUA UNIVERSITY, Hsinchu (TW)

(72) Inventors: Sheng-Kai Wang, Hsinchu (TW); Cin-Hao Lin, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/853,877

(22) Filed: Dec. 25, 2017

(65) Prior Publication Data
US 2019/0194590 A1 Jun. 27, 2019

(51) Int. Cl.
*C08G 69/48* (2006.01)
*C08J 3/24* (2006.01)
*C08L 77/04* (2006.01)
*C12M 1/12* (2006.01)
*C07D 487/22* (2006.01)
*C12N 5/00* (2006.01)
*A61L 27/22* (2006.01)

(52) U.S. Cl.
CPC .......... *C12M 25/14* (2013.01); *A61L 27/227* (2013.01); *C07D 487/22* (2013.01); *C08G 69/48* (2013.01); *C08J 3/246* (2013.01); *C08L 77/04* (2013.01); *C12N 5/0068* (2013.01); *A61F 2240/001* (2013.01); *C08J 2377/04* (2013.01); *C12N 2513/00* (2013.01); *C12N 2533/30* (2013.01)

(58) Field of Classification Search
CPC ...... C07D 487/22; C08G 69/10; C08G 69/46; C08G 69/48; C08J 3/246; C08J 2377/04; C08L 77/04
See application file for complete search history.

(56) References Cited

U.S. PATENT DOCUMENTS 4,894,226 A * 1/1990 Aldwin ............... A61K 47/645
424/179.1

OTHER PUBLICATIONS

Choi et al. Synthesis and Conformational Analysis of Macrocyclic Peptides Consisting of Both alpha-Helix and Polyproline Helix Segments. Biopolymers. Jul. 19, 2013, vol. 101, No. 3, pp. 279-286. (Year: 2013).*

Fillon et al. Cell Penetrating Agents Based on a Polyproline Helix Scaffold. Journal of the American Chemical Society. 2005, vol. 127, No. 33, pp. 11798-11803. (Year: 2005).*

(Continued)

*Primary Examiner* — Jeffrey E. Russel
(74) *Attorney, Agent, or Firm* — CKC & Partners Co., LLC

(57) ABSTRACT

A polygonal scaffold includes at least three polyproline II (PPII) helix rods and at least three connectors. Each of the PPII helix rods is composed of a plurality of repeat units represented by Formula (i), and at least one of the PPII helix rods has at least one hydrogen atom of at least one of the repeat units being substituted by a first chemical handle for connecting a ligand. Each of the connectors is a divalent organic group, and every two of the PPII helix rods are connected by one of the connectors to form a closed ring. Therefore, with the uniform composition, the PPII helix rods have a stable helical structure under aqueous conditions, and a desired rigidity can be provided.

24 Claims, 16 Drawing Sheets
Specification includes a Sequence Listing.

(56) References Cited

OTHER PUBLICATIONS

T. Lou. The Synthesis and Structural Studies of Oligoproline Macrocycles. Department of Chemistry, University of Toronto. (Year: 2011).*

Scully et al. Bending Rigid Molecular Rods: Formation of Oligoproline Macrocycles. Chemistry: A European Journal. 2012. vol. 18, pp. 15612-15617. (Year: 2012).*

* cited by examiner

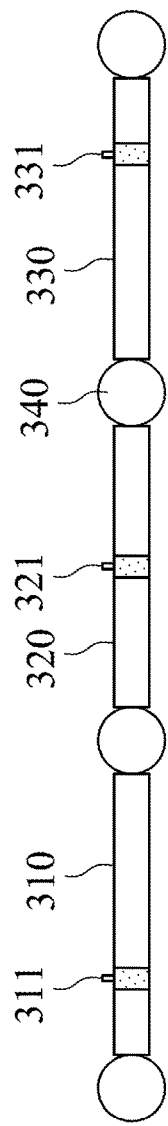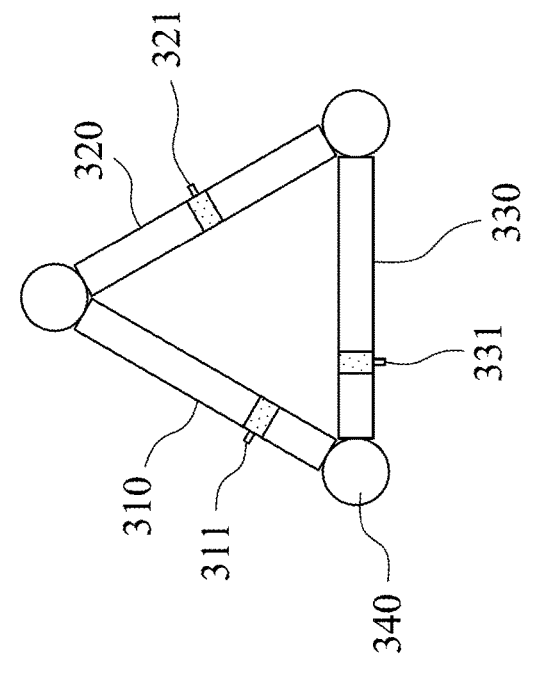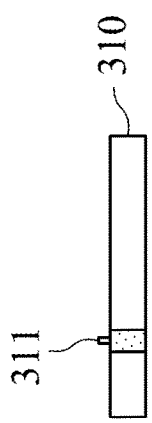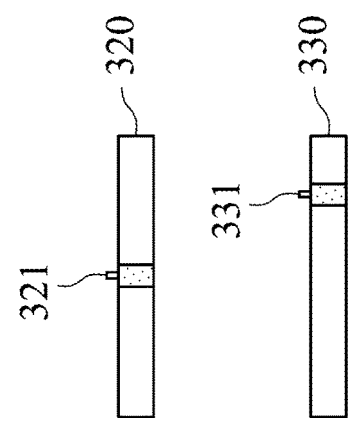
Fig. 7B
Fig. 7C
Fig. 7A

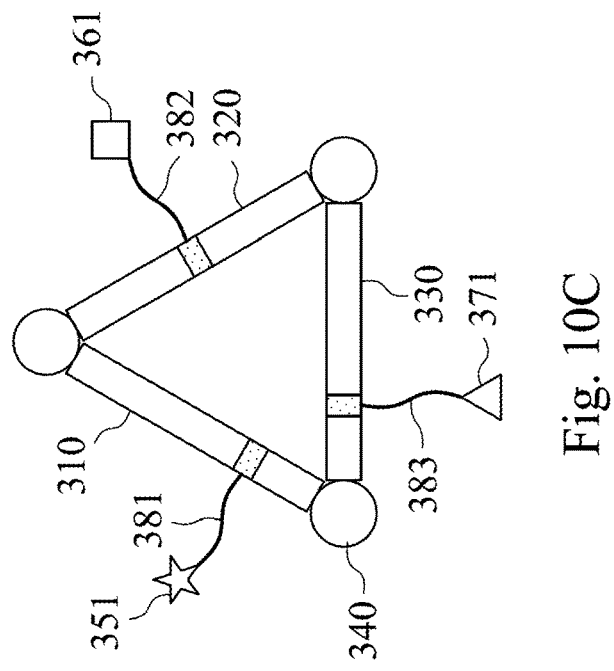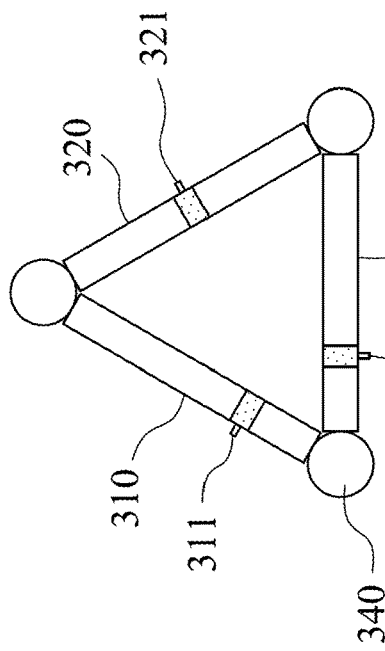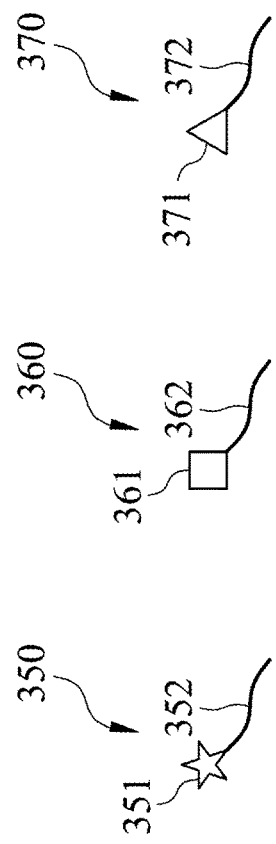
Fig. 10A
Fig. 10B
Fig. 10C

SEQUENCE LISTING

<160> NUMBER OF SEQ ID NOS: 45

<210> SEQ ID NO 1
<211> LENGTH: 9
<212> TYPE: PRT
<213> ORGANISM: Artificial Sequence
<220> FEATURE:
<223> OTHER INFORMATION: C1
<220> FEATURE:
<221> NAME/KEY: PEPTIDE
<222> LOCATION: (1)..(1)
<223> OTHER INFORMATION: Xaa at residue 11 is derivative 1 of proline

<400> SEQUENCE: 1

Xaa Pro Pro Pro Pro Pro Pro Pro Pro
1 5

<210> SEQ ID NO 2
<211> LENGTH: 9
<212> TYPE: PRT
<213> ORGANISM: Artificial Sequence
<220> FEATURE:
<223> OTHER INFORMATION: C2
<220> FEATURE:
<221> NAME/KEY: PEPTIDE
<222> LOCATION: (1)..(1)
<223> OTHER INFORMATION: Xaa at residue 1 is derivative 12 of proline

<400> SEQUENCE: 2

Xaa Pro Pro Pro Pro Pro Pro Pro Pro
1 5

<210> SEQ ID NO 3
<211> LENGTH: 9
<212> TYPE: PRT
<213> ORGANISM: Artificial Sequence
<220> FEATURE:
<223> OTHER INFORMATION: C3
<220> FEATURE:
<221> NAME/KEY: PEPTIDE
<222> LOCATION: (1)..(1)
<223> OTHER INFORMATION: Xaa at residue 1 is derivative 11 of proline
<220> FEATURE:
<221> NAME/KEY: PEPTIDE
<222> LOCATION: (4)..(4)
<223> OTHER INFORMATION: Xaa at residue 4 is derivative 1 of proline

<400> SEQUENCE: 3

Xaa Pro Pro Xaa Pro Pro Pro Pro Pro
1 5

<210> SEQ ID NO 4
<211> LENGTH: 9
<212> TYPE: PRT
<213> ORGANISM: Artificial Sequence
<220> FEATURE:
<223> OTHER INFORMATION: C4
<220> FEATURE:
<221> NAME/KEY: PEPTIDE
<222> LOCATION: (1)..(1)
<223> OTHER INFORMATION: Xaa at residue 1 is derivative 13 of proline

<400> SEQUENCE: 4

```
Xaa Pro Pro Pro Pro Pro Pro Pro Pro
1               5

<210> SEQ ID NO 5
<211> LENGTH: 9
<212> TYPE: PRT
<213> ORGANISM: Artificial Sequence
<220> FEATURE:
<223> OTHER INFORMATION: C5
<220> FEATURE:
<221> NAME/KEY: PEPTIDE
<222> LOCATION: (1)..(1)
<223> OTHER INFORMATION: Xaa at residue 1 is derivative 13 of proline
<220> FEATURE:
<221> NAME/KEY: PEPTIDE
<222> LOCATION: (7)..(7)
<223> OTHER INFORMATION: Xaa at residue 7 is derivative 2 of proline

<400> SEQUENCE: 5

Xaa Pro Pro Pro Pro Pro Xaa Pro Pro
1               5

<210> SEQ ID NO 6
<211> LENGTH: 9
<212> TYPE: PRT
<213> ORGANISM: Artificial Sequence
<220> FEATURE:
<223> OTHER INFORMATION: C6
<220> FEATURE:
<221> NAME/KEY: PEPTIDE
<222> LOCATION: (1)..(1)
<223> OTHER INFORMATION: Xaa at residue 1 is derivative 13 of proline
<220> FEATURE:
<221> NAME/KEY: PEPTIDE
<222> LOCATION: (4)..(7)
<223> OTHER INFORMATION: Xaa at residues 4 and 7 is derivative 2 of
      proline

<400> SEQUENCE: 6

Xaa Pro Pro Xaa Pro Pro Xaa Pro Pro
1               5

<210> SEQ ID NO 7
<211> LENGTH: 9
<212> TYPE: PRT
<213> ORGANISM: Artificial Sequence
<220> FEATURE:
<223> OTHER INFORMATION: C11
<220> FEATURE:
<221> NAME/KEY: PEPTIDE
<222> LOCATION: (1)..(1)
<223> OTHER INFORMATION: Xaa at residue 1 is derivative 14 of proline

<400> SEQUENCE: 7

Xaa Pro Pro Pro Pro Pro Pro Pro Pro
1               5

<210> SEQ ID NO 8
<211> LENGTH: 9
<212> TYPE: PRT
<213> ORGANISM: Artificial Sequence
<220> FEATURE:
<223> OTHER INFORMATION: C12
<220> FEATURE:
<221> NAME/KEY: PEPTIDE
<222> LOCATION: (1)..(1)
<223> OTHER INFORMATION: Xaa at residue 1 is derivative 14 of proline
<220> FEATURE:
<221> NAME/KEY: PEPTIDE
<222> LOCATION: (9)..(9)
<223> OTHER INFORMATION: Xaa at residue 9 is derivative 15 of proline
```

```
<400> SEQUENCE: 8

Xaa Pro Pro Pro Pro Pro Pro Pro Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: C13
<220> FEATURE:
<221> NAME/KEY: PEPTIDE
<222> LOCATION: (1)..(1)
<223> OTHER INFORMATION: Xaa at residue 1 is derivative 11 of proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 9

Xaa Pro Pro Pro Pro Pro Pro Pro Xaa
1               5

<210> SEQ ID NO 10
<211> LENGTH: 9
<212> TYPE: PRT
<213> ORGANISM: Artificial Sequence
<220> FEATURE:
<223> OTHER INFORMATION: C21
<220> FEATURE:
<221> NAME/KEY: PEPTIDE
<222> LOCATION: (1)..(1)
<223> OTHER INFORMATION: Xaa at residue 1 is derivative 12 of proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 10

Xaa Pro Pro Pro Pro Pro Pro Pro Xaa
1               5

<210> SEQ ID NO 11
<211> LENGTH: 9
<212> TYPE: PRT
<213> ORGANISM: Artificial Sequence
<220> FEATURE:
<223> OTHER INFORMATION: C31
<220> FEATURE:
<221> NAME/KEY: PEPTIDE
<222> LOCATION: (1)..(1)
<223> OTHER INFORMATION: Xaa at residue 1 is derivative 11 of proline
<220> FEATURE:
<221> NAME/KEY: PEPTIDE
<222> LOCATION: (4)..(4)
<223> OTHER INFORMATION: Xaa at residue 4 is derivative 1 of proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 11

Xaa Pro Pro Xaa Pro Pro Pro Pro Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: C41
```

```
<220> FEATURE:
<221> NAME/KEY: PEPTIDE
<222> LOCATION: (1)..(1)
<223> OTHER INFORMATION: Xaa at residue 1 is derivative 13 of proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 12

Xaa Pro Pro Pro Pro Pro Pro Pro Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: C51
<220> FEATURE:
<221> NAME/KEY: PEPTIDE
<222> LOCATION: (1)..(1)
<223> OTHER INFORMATION: Xaa at residue 1 is derivative 13 of proline
<220> FEATURE:
<221> NAME/KEY: PEPTIDE
<222> LOCATION: (7)..(7)
<223> OTHER INFORMATION: Xaa at residue 7 is derivative 2 of proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 13

Xaa Pro Pro Pro Pro Pro Xaa Pro Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: C61
<220> FEATURE:
<221> NAME/KEY: PEPTIDE
<222> LOCATION: (1)..(1)
<223> OTHER INFORMATION: Xaa at residue 1 is derivative 13 of proline
<220> FEATURE:
<221> NAME/KEY: PEPTIDE
<222> LOCATION: (4)..(7)
<223> OTHER INFORMATION: Xaa at residues 4 and 7 is derivative 2 of
      proline
<220> FEATURE:
<221> NAME/KEY: PEPTIDE
<222> LOCATION: (9)..(9)
<223> OTHER INFORMATION: Xaa at residue 9 is derivative 15 of proline

<400> SEQUENCE: 14

Xaa Pro Pro Xaa Pro Pro Xaa Pro Xaa
1               5

<210> SEQ ID NO 15
<211> LENGTH: 27
<212> TYPE: PRT
<213> ORGANISM: Artificial Sequence
<220> FEATURE:
<223> OTHER INFORMATION: L1
<220> FEATURE:
<221> NAME/KEY: PEPTIDE
<222> LOCATION: (1)..(1)
<223> OTHER INFORMATION: Xaa at residue 1 is derivative 16 of proline
<220> FEATURE:
<221> NAME/KEY: PEPTIDE
<222> LOCATION: (10)..(19)
```

<223> OTHER INFORMATION: Xaa at residues 10 and 19 is derivative 1 of
      proline

<400> SEQUENCE: 15

Xaa Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 16
<211> LENGTH: 27
<212> TYPE: PRT
<213> ORGANISM: Artificial Sequence
<220> FEATURE:
<223> OTHER INFORMATION: L2
<220> FEATURE:
<221> NAME/KEY: PEPTIDE
<222> LOCATION: (1)..(1)
<223> OTHER INFORMATION: Xaa at residue 1 is derivative 14 of proline
<220> FEATURE:
<221> NAME/KEY: PEPTIDE
<222> LOCATION: (4)..(22)
<223> OTHER INFORMATION: Xaa at residues 4, 13 and 22 is derivative 1
      of proline

<400> SEQUENCE: 16

Xaa Pro Pro Xaa Pro Pro Pro Pro Pro Pro Pro Pro Xaa Pro Pro
1               5                   10                  15

Pro Pro Pro Pro Pro Xaa Pro Pro Pro Pro
            20                  25

<210> SEQ ID NO 17
<211> LENGTH: 27
<212> TYPE: PRT
<213> ORGANISM: Artificial Sequence
<220> FEATURE:
<223> OTHER INFORMATION: L3
<220> FEATURE:
<221> NAME/KEY: PEPTIDE
<222> LOCATION: (1)..(1)
<223> OTHER INFORMATION: Xaa at residue 1 is derivative 17 of proline
<220> FEATURE:
<221> NAME/KEY: PEPTIDE
<222> LOCATION: (10)..(19)
<223> OTHER INFORMATION: Xaa at residues 10 and 19 is derivative 2 of
      proline

<400> SEQUENCE: 17

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 18
<211> LENGTH: 27
<212> TYPE: PRT
<213> ORGANISM: Artificial Sequence
<220> FEATURE:
<223> OTHER INFORMATION: L4
<220> FEATURE:
<221> NAME/KEY: PEPTIDE
<222> LOCATION: (1)..(1)
<223> OTHER INFORMATION: Xaa at residue 1 is derivative 18 of proline
<220> FEATURE:
<221> NAME/KEY: PEPTIDE
<222> LOCATION: (10)..(19)
<223> OTHER INFORMATION: Xaa at residues 10, 16 and 19 is derivative 2
      of proline

<400> SEQUENCE: 18

-continued

```
Xaa Pro Pro Pro Pro Pro Pro Pro Xaa Pro Pro Pro Pro Xaa
1               5                   10                  15

Pro Pro Xaa Pro Pro Pro Pro Pro Pro Pro
            20                  25

<210> SEQ ID NO 19
<211> LENGTH: 27
<212> TYPE: PRT
<213> ORGANISM: Artificial Sequence
<220> FEATURE:
<223> OTHER INFORMATION: L5
<220> FEATURE:
<221> NAME/KEY: PEPTIDE
<222> LOCATION: (1)..(1)
<223> OTHER INFORMATION: Xaa at residue 1 is derivative 18 of proline
<220> FEATURE:
<221> NAME/KEY: PEPTIDE
<222> LOCATION: (10)..(16)
<223> OTHER INFORMATION: Xaa at residues 10, 13 and 16 is derivative 2
      of proline

<400> SEQUENCE: 19

Xaa Pro Pro Pro Pro Pro Pro Pro Pro Xaa Pro Pro Xaa Pro Pro Xaa
1               5                   10                  15

Pro Pro Pro Pro Pro Pro Pro Pro Pro Pro
            20                  25

<210> SEQ ID NO 20
<211> LENGTH: 27
<212> TYPE: PRT
<213> ORGANISM: Artificial Sequence
<220> FEATURE:
<223> OTHER INFORMATION: L11
<220> FEATURE:
<221> NAME/KEY: PEPTIDE
<222> LOCATION: (1)..(1)
<223> OTHER INFORMATION: Xaa at residue 1 is derivative 16 of proline
<220> FEATURE:
<221> NAME/KEY: PEPTIDE
<222> LOCATION: (10)..(19)
<223> OTHER INFORMATION: Xaa at residues 10 and 19 is derivative 1 of
      proline
<220> FEATURE:
<221> NAME/KEY: PEPTIDE
<222> LOCATION: (27)..(27)
<223> OTHER INFORMATION: Xaa at residue 27 is derivative 15 of proline

<400> SEQUENCE: 20

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro Xaa
            20                  25

<210> SEQ ID NO 21
<211> LENGTH: 27
<212> TYPE: PRT
<213> ORGANISM: Artificial Sequence
<220> FEATURE:
<223> OTHER INFORMATION: L21
<220> FEATURE:
<221> NAME/KEY: PEPTIDE
<222> LOCATION: (1)..(1)
<223> OTHER INFORMATION: Xaa at residue 1 is derivative 14 of proline
<220> FEATURE:
<221> NAME/KEY: PEPTIDE
<222> LOCATION: (4)..(22)
<223> OTHER INFORMATION: Xaa at residues 4, 13 and 22 is derivative 1
      of proline
<220> FEATURE:
<221> NAME/KEY: PEPTIDE
```

<222> LOCATION: (27)..(27)
<223> OTHER INFORMATION: Xaa at residue 27 is derivative 15 of proline

<400> SEQUENCE: 21

```
Xaa Pro Pro Xaa Pro Pro Pro Pro Pro Pro Xaa Pro Pro Pro
1               5                   10                  15

Pro Pro Pro Pro Pro Xaa Pro Pro Pro Pro Xaa
                20                  25
```

<210> SEQ ID NO 22
<211> LENGTH: 27
<212> TYPE: PRT
<213> ORGANISM: Artificial Sequence
<220> FEATURE:
<223> OTHER INFORMATION: L31
<220> FEATURE:
<221> NAME/KEY: PEPTIDE
<222> LOCATION: (1)..(1)
<223> OTHER INFORMATION: Xaa at residue 1 is derivative 17 of proline
<220> FEATURE:
<221> NAME/KEY: PEPTIDE
<222> LOCATION: (10)..(19)
<223> OTHER INFORMATION: Xaa at residues 10 and 19 is derivative 2 of
      proline
<220> FEATURE:
<221> NAME/KEY: PEPTIDE
<222> LOCATION: (27)..(27)
<223> OTHER INFORMATION: Xaa at residue 27 is derivative 15 of proline

<400> SEQUENCE: 22

```
Xaa Pro Pro Pro Pro Pro Pro Pro Pro Xaa Pro Pro Pro Pro Pro
1               5                   10                  15

Pro Pro Xaa Pro Pro Pro Pro Pro Pro Pro Xaa
                20                  25
```

<210> SEQ ID NO 23
<211> LENGTH: 27
<212> TYPE: PRT
<213> ORGANISM: Artificial Sequence
<220> FEATURE:
<223> OTHER INFORMATION: L41
<220> FEATURE:
<221> NAME/KEY: PEPTIDE
<222> LOCATION: (1)..(1)
<223> OTHER INFORMATION: Xaa at residue 1 is derivative 18 of proline
<220> FEATURE:
<221> NAME/KEY: PEPTIDE
<222> LOCATION: (10)..(19)
<223> OTHER INFORMATION: Xaa at residues 10, 16 and 19 is derivative 2
      of proline
<220> FEATURE:
<221> NAME/KEY: PEPTIDE
<222> LOCATION: (27)..(27)
<223> OTHER INFORMATION: Xaa at residue 27 is derivative 15 of proline

<400> SEQUENCE: 23

```
Xaa Pro Pro Pro Pro Pro Pro Pro Pro Xaa Pro Pro Pro Pro Xaa
1               5                   10                  15

Pro Pro Xaa Pro Pro Pro Pro Pro Pro Pro Xaa
                20                  25
```

<210> SEQ ID NO 24
<211> LENGTH: 27
<212> TYPE: PRT
<213> ORGANISM: Artificial Sequence
<220> FEATURE:
<223> OTHER INFORMATION: L51
<220> FEATURE:
<221> NAME/KEY: PEPTIDE
<222> LOCATION: (1)..(1)

```
<223> OTHER INFORMATION: Xaa at residue 1 is derivative 18 of proline
<220> FEATURE:
<221> NAME/KEY: PEPTIDE
<222> LOCATION: (10)..(16)
<223> OTHER INFORMATION: Xaa at residues 10, 13 and 16 is derivative 2
      of proline
<220> FEATURE:
<221> NAME/KEY: PEPTIDE
<222> LOCATION: (27)..(27)
<223> OTHER INFORMATION: Xaa at residue 27 is derivative 15 of proline

<400> SEQUENCE: 24

Xaa Pro Pro Pro Pro Pro Pro Pro Pro Xaa Pro Pro Xaa Pro Pro Xaa
1               5                   10                  15

Pro Pro Pro Pro Pro Pro Pro Pro Pro Pro Xaa
            20                  25

<210> SEQ ID NO 25
<211> LENGTH: 27
<212> TYPE: PRT
<213> ORGANISM: Artificial Sequence
<220> FEATURE:
<223> OTHER INFORMATION: S1
<220> FEATURE:
<221> NAME/KEY: PEPTIDE
<222> LOCATION: (1)..(19)
<223> OTHER INFORMATION: Xaa at residues 1, 10 and 19 is derivative 1
      of proline

<400> SEQUENCE: 25

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 26
<211> LENGTH: 27
<212> TYPE: PRT
<213> ORGANISM: Artificial Sequence
<220> FEATURE:
<223> OTHER INFORMATION: S2
<220> FEATURE:
<221> NAME/KEY: PEPTIDE
<222> LOCATION: (4)..(22)
<223> OTHER INFORMATION: Xaa at residues 4, 13 and 22 is derivative 1
      of proline

<400> SEQUENCE: 26

Pro Pro Pro Xaa Pro Pro Pro Pro Pro Pro Pro Pro Xaa Pro Pro
1               5                   10                  15

Pro Pro Pro Pro Pro Pro Xaa Pro Pro Pro Pro
            20                  25

<210> SEQ ID NO 27
<211> LENGTH: 27
<212> TYPE: PRT
<213> ORGANISM: Artificial Sequence
<220> FEATURE:
<223> OTHER INFORMATION: S3
<220> FEATURE:
<221> NAME/KEY: PEPTIDE
<222> LOCATION: (1)..(19)
<223> OTHER INFORMATION: Xaa at residues 1, 10 and 19 is derivative 2
      of proline

<400> SEQUENCE: 27

Xaa Pro Pro Pro Pro Pro Pro Pro Pro Xaa Pro Pro Pro Pro Pro
1               5                   10                  15
```

Pro Pro Xaa Pro Pro Pro Pro Pro Pro
            20                  25

<210> SEQ ID NO 28
<211> LENGTH: 27
<212> TYPE: PRT
<213> ORGANISM: Artificial Sequence
<220> FEATURE:
<223> OTHER INFORMATION: S4
<220> FEATURE:
<221> NAME/KEY: PEPTIDE
<222> LOCATION: (10)..(19)
<223> OTHER INFORMATION: Xaa at residues 10, 16 and 19 is derivative 2
      of proline

<400> SEQUENCE: 28

Pro Pro Pro Pro Pro Pro Pro Pro Pro Xaa Pro Pro Pro Pro Pro Xaa
1               5                   10                  15

Pro Pro Xaa Pro Pro Pro Pro Pro Pro Pro
            20                  25

<210> SEQ ID NO 29
<211> LENGTH: 27
<212> TYPE: PRT
<213> ORGANISM: Artificial Sequence
<220> FEATURE:
<223> OTHER INFORMATION: S5
<220> FEATURE:
<221> NAME/KEY: PEPTIDE
<222> LOCATION: (10)..(16)
<223> OTHER INFORMATION: Xaa at residues 10, 13 and 16 is derivative 1
      of proline

<400> SEQUENCE: 29

Pro Pro Pro Pro Pro Pro Pro Pro Pro Xaa Pro Pro Xaa Pro Pro Xaa
1               5                   10                  15

Pro Pro Pro Pro Pro Pro Pro Pro Pro Pro
            20                  25

<210> SEQ ID NO 30
<211> LENGTH: 27
<212> TYPE: PRT
<213> ORGANISM: Artificial Sequence
<220> FEATURE:
<223> OTHER INFORMATION: S6

<400> SEQUENCE: 30

Pro Pro Pro Pro Pro Pro Pro Pro Pro Pro Pro Pro Pro Pro Pro Pro
1               5                   10                  15

Pro Pro Pro Pro Pro Pro Pro Pro Pro Pro
            20                  25

<210> SEQ ID NO 31
<211> LENGTH: 27
<212> TYPE: PRT
<213> ORGANISM: Artificial Sequence
<220> FEATURE:
<223> OTHER INFORMATION: S11
<220> FEATURE:
<221> NAME/KEY: PEPTIDE
<222> LOCATION: (1)..(19)
<223> OTHER INFORMATION: Xaa at residues 1, 10 and 19 is derivative 3
      of proline

<400> SEQUENCE: 31

Xaa Pro Pro Pro Pro Pro Pro Pro Pro Xaa Pro Pro Pro Pro Pro
1               5                   10                  15

```
Pro Pro Xaa Pro Pro Pro Pro Pro Pro
            20                  25

<210> SEQ ID NO 32
<211> LENGTH: 27
<212> TYPE: PRT
<213> ORGANISM: Artificial Sequence
<220> FEATURE:
<223> OTHER INFORMATION: S31
<220> FEATURE:
<221> NAME/KEY: PEPTIDE
<222> LOCATION: (1)..(19)
<223> OTHER INFORMATION: Xaa at residues 1, 10 and 19 is derivative 4
      of proline

<400> SEQUENCE: 32

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 33
<211> LENGTH: 27
<212> TYPE: PRT
<213> ORGANISM: Artificial Sequence
<220> FEATURE:
<223> OTHER INFORMATION: S41
<220> FEATURE:
<221> NAME/KEY: PEPTIDE
<222> LOCATION: (10)..(19)
<223> OTHER INFORMATION: Xaa at residues 10, 16 and 19 is derivative 4
      of proline

<400> SEQUENCE: 33

Pro Pro Pro Pro Pro Pro Pro Pro Pro Xaa Pro Pro Pro Pro Xaa
1               5                   10                  15

Pro Pro Xaa Pro Pro Pro Pro Pro Pro Pro
            20                  25

<210> SEQ ID NO 34
<211> LENGTH: 28
<212> TYPE: PRT
<213> ORGANISM: Artificial Sequence
<220> FEATURE:
<223> OTHER INFORMATION: S51
<220> FEATURE:
<221> NAME/KEY: PEPTIDE
<222> LOCATION: (10)..(19)
<223> OTHER INFORMATION: Xaa at residues 10, 13, 16 and 19 is derivative
      4 of proline

<400> SEQUENCE: 34

Pro Pro Pro Pro Pro Pro Pro Pro Pro Xaa Pro Pro Xaa Pro Pro Xaa
1               5                   10                  15

Pro Pro Xaa Pro Pro Pro Pro Pro Pro Pro
            20                  25

<210> SEQ ID NO 35
<211> LENGTH: 27
<212> TYPE: PRT
<213> ORGANISM: Artificial Sequence
<220> FEATURE:
<223> OTHER INFORMATION: S32
<220> FEATURE:
<221> NAME/KEY: PEPTIDE
<222> LOCATION: (1)..(19)
<223> OTHER INFORMATION: Xaa at residues 1, 10 and 19 is derivative 5 of
      proline
```

```
<400> SEQUENCE: 35

Xaa Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 36
<211> LENGTH: 27
<212> TYPE: PRT
<213> ORGANISM: Artificial Sequence
<220> FEATURE:
<223> OTHER INFORMATION: S42
<220> FEATURE:
<221> NAME/KEY: PEPTIDE
<222> LOCATION: (10)..(19)
<223> OTHER INFORMATION: Xaa at residues 10, 16 and 19 is derivative 5
      of proline

<400> SEQUENCE: 36

Pro Pro Pro Pro Pro Pro Pro Pro Pro Xaa Pro Pro Pro Pro Xaa
1               5                   10                  15

Pro Pro Xaa Pro Pro Pro Pro Pro Pro Pro
            20                  25

<210> SEQ ID NO 37
<211> LENGTH: 27
<212> TYPE: PRT
<213> ORGANISM: Artificial Sequence
<220> FEATURE:
<223> OTHER INFORMATION: S52
<220> FEATURE:
<221> NAME/KEY: PEPTIDE
<222> LOCATION: (10)..(16)
<223> OTHER INFORMATION: Xaa at residues 10, 13 and 16 is derivative 5
      of proline

<400> SEQUENCE: 37

Pro Pro Pro Pro Pro Pro Pro Pro Pro Xaa Pro Pro Xaa Pro Pro Xaa
1               5                   10                  15

Pro Pro Pro Pro Pro Pro Pro Pro Pro Pro Pro
            20                  25

<210> SEQ ID NO 38
<211> LENGTH: 27
<212> TYPE: PRT
<213> ORGANISM: Artificial Sequence
<220> FEATURE:
<223> OTHER INFORMATION: SL1
<220> FEATURE:
<221> NAME/KEY: PEPTIDE
<222> LOCATION: (1)..(19)
<223> OTHER INFORMATION: Xaa at residues 1, 10 and 19 is derivative 6
      of proline

<400> SEQUENCE: 38

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 39
<211> LENGTH: 27
<212> TYPE: PRT
<213> ORGANISM: Artificial Sequence
<220> FEATURE:
<223> OTHER INFORMATION: SL2
<220> FEATURE:
```

```
<221> NAME/KEY: PEPTIDE
<222> LOCATION: (1)..(19)
<223> OTHER INFORMATION: Xaa at residues 1, 10 and 19 is derivative 7
      of proline

<400> SEQUENCE: 39

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 40
<211> LENGTH: 27
<212> TYPE: PRT
<213> ORGANISM: Artificial Sequence
<220> FEATURE:
<223> OTHER INFORMATION: SL3
<220> FEATURE:
<221> NAME/KEY: PEPTIDE
<222> LOCATION: (1)..(19)
<223> OTHER INFORMATION: Xaa at residues 1, 10 and 19 is derivative 8
      of proline

<400> SEQUENCE: 40

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 41
<211> LENGTH: 27
<212> TYPE: PRT
<213> ORGANISM: Artificial Sequence
<220> FEATURE:
<223> OTHER INFORMATION: SL4
<220> FEATURE:
<221> NAME/KEY: PEPTIDE
<222> LOCATION: (1)..(19)
<223> OTHER INFORMATION: Xaa at residues 1, 10 and 19 is derivative 9
      of proline

<400> SEQUENCE: 41

Xaa Pro Pro Pro Pro Pro Pro Pro Pro Xaa Pro Pro Pro Pro Pro
1               5                   10                  15

Pro Pro Xaa Pro Pro Pro Pro Pro Pro Pro
            20                  25

<210> SEQ ID NO 42
<211> LENGTH: 27
<212> TYPE: PRT
<213> ORGANISM: Artificial Sequence
<220> FEATURE:
<223> OTHER INFORMATION: SL5
<220> FEATURE:
<221> NAME/KEY: PEPTIDE
<222> LOCATION: (10)..(19)
<223> OTHER INFORMATION: Xaa at residues 10, 16 and 19 is derivative 9
      of proline

<400> SEQUENCE: 42

Pro Pro Pro Pro Pro Pro Pro Pro Pro Xaa Pro Pro Pro Pro Pro Xaa
1               5                   10                  15

Pro Pro Xaa Pro Pro Pro Pro Pro Pro Pro
            20                  25

<210> SEQ ID NO 43
<211> LENGTH: 27
```

```
<212> TYPE: PRT
<213> ORGANISM: Artificial Sequence
<220> FEATURE:
<223> OTHER INFORMATION: SL6
<220> FEATURE:
<221> NAME/KEY: PEPTIDE
<222> LOCATION: (10)..(16)
<223> OTHER INFORMATION: Xaa at residues 10, 13 and 16 is derivative 9
      of proline

<400> SEQUENCE: 43

Pro Pro Pro Pro Pro Pro Pro Pro Pro Xaa Pro Pro Xaa Pro Pro Xaa
1               5                   10                  15

Pro Pro Pro Pro Pro Pro Pro Pro Pro Pro
            20                  25

<210> SEQ ID NO 44
<211> LENGTH: 9
<212> TYPE: PRT
<213> ORGANISM: Artificial Sequence
<220> FEATURE:
<223> OTHER INFORMATION: 3A

<400> SEQUENCE: 44

Pro Pro Pro Pro Pro Pro Pro Pro Pro
1               5

<210> SEQ ID NO 45
<211> LENGTH: 9
<212> TYPE: PRT
<213> ORGANISM: Artificial Sequence
<220> FEATURE:
<223> OTHER INFORMATION: 3B
<220> FEATURE:
<221> NAME/KEY: PEPTIDE
<222> LOCATION: (2)..(2)
<223> OTHER INFORMATION: Xaa at residue 2 is derivative 10 of proline

<400> SEQUENCE: 45

Pro Xaa Pro Pro Pro Pro Pro Pro Pro
1               5
```

POLYGONAL SCAFFOLD AND MANUFACTURING METHOD THEREOF, AND PROTEIN MODULATOR AND MANUFACTURING METHOD THEREOF

The sequence listing submitted via EFS, in compliance with 37 CFR § 1.52(e)(5), is incorporated herein by reference. The sequence listing text file submitted via EFS contains the file "TWT05670US_SequenceListing", created on Nov. 16, 2018, which is 19,915 bytes in size.

BACKGROUND

Technical Field

The present disclosure relates to a polygonal scaffold and manufacturing method thereof, and protein modulator and manufacturing method thereof. More particularly, the present disclosure relates to a rigid polygonal scaffold and manufacturing method thereof, and protein modulator and manufacturing method thereof.

Description of Related Art

Membrane proteins, including many receptors, are a class of proteins that attach or associate with biological phospholipid bilayer. The receptors involve in essential cellular functions such as cell recognition and signal transduction. For example, the signal of adenosine receptors can suppress activity in the central nervous system. For another example, the opioid receptors involve in pain signal. Consequently, many of the receptors have been recognized as pharmaceutical targets, in which over 50% of all modern drugs are involved.

Specifically, when suitable ligands are provided to the target receptors, physiological processes can be regulated. Moreover, when the ligands are provided to the target receptors in a multivalent manner, the interaction between the ligands and the target receptors can be increased significantly. Therefore, scaffolds bearing multiple ligands are developed to control the receptors. FIG. 1 shows conventional scaffolds bearing multiple ligands. As shown in FIG. 1, the conventional scaffolds include a polymer type 10, a dendrimer type 20, a dendron type 30, a cluster type 40, and a linear type 50. The polymer type 10, the dendrimer type 20, and the dendron type 30 can provide plenty of reactive sites (where the ligands located). However, the distance between the ligands of the polymer type 10 is difficult to be controlled because firstly the conformation of the polymer chain is usually unpredictable and secondly the chain length of polymerization reaction is not precise, which distributes within a certain range. As for the dendrimer type 20 and the dendron type 30, it is difficulty to conjugate the ligands thereon due to steric hindrances. Accordingly, the synthesis difficulty of the dendrimer type 20 and the dendron type 30 is high. The cluster type 40 has the shortcoming of disordered arrangement of the ligands, and the pattern of the ligands cannot be precisely controlled. As for the linear type 50, the linear type 50 usually has a flexible chain, which results in a higher entropy comparing to a rigid scaffold. As a result, the spatial selectivity of linear type 50 with a flexible chain is poorer than that of the rigid scaffold. Moreover, the linear type 50 is extended along one dimension. However, the surface of the cell membrane is in two dimensions. Accordingly, the spatial correspondence between the linear type 50 and the receptors is poor. FIG. 2A shows an interaction between a flexible scaffold 60 and a receptor R1, FIG. 2B shows an interaction between the flexible scaffold 60 in FIG. 2A and another receptor R2, and FIG. 2C shows an interaction between a rigid scaffold 70 and the receptor R2 in FIG. 2B, all of which are for illustrating the spatial selectivity of the flexible scaffold 60 and the rigid scaffold 70. As shown in FIGS. 2A and 2B, the ligands L of the flexible scaffold 60 can interact with the receptor R1 and the receptor R2 which have different binding site distances. However, as shown in FIG. 2C, the ligands L of the rigid scaffold 70 can only interact with the receptor R2 with a longer binding site distance due to the rigidity. It is clearly that the spatial selectivity of the flexible scaffold 60 is poorer than that of the rigid scaffold 70.

Therefore, the avidity for the receptors of the conventional scaffolds bearing multiple ligands is still poor, and the control ability for the receptors provided by the conventional scaffolds bearing multiple ligands is unsatisfactory. The relevant industry and academia still pursue a scaffold bearing multiple ligands which has properties as follows. First, the scaffold can provide sufficient rigidity, so that a better spatial selectivity can be provided. Second, the location of the ligands can be precisely controlled, which is favorable to fit the target proteins on cell membrane, so that a better selectivity can be provided.

SUMMARY

According to one aspect of the present disclosure, a polygonal scaffold includes at least three polyproline II (PPII) helix rods and at least three connectors. Each of the PPII helix rods is composed of a plurality of repeat units represented by Formula (i):

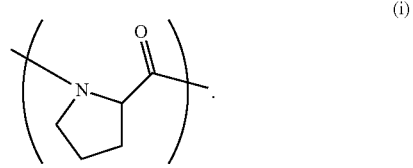

At least one of the PPII helix rods has at least one of hydrogen atoms of at least one of the repeat units being substituted by a first chemical handle for connecting a ligand. Each of the connectors is a divalent organic group, and every two of the PPII helix rods are connected by one of the connectors to form a closed ring.

According to another aspect of the present disclosure, a method for manufacturing the aforementioned polygonal scaffold includes steps as follows. A rod forming step is provided, and an assembling step is provided. In the rod forming step, the PPII helix rods are formed. In the assembling step, every two of the PPII helix rods are connected by one of the connectors to form the closed ring.

According to yet another aspect of the present disclosure, a protein modulator includes a polygonal scaffold and at least one ligand. The polygonal scaffold includes at least three PPII helix rods and at least three connectors. Each of the PPII helix rods is composed of a plurality of repeat units represented by Formula (i):

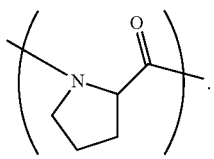

At least one of the PPII helix rods has at least one of hydrogen atoms of at least one of the repeat units being substituted by a linker. Each of the connectors is a divalent organic group, and every two of the PPII helix rods are connected by one of the connectors to form a closed ring. The ligand is connected with one of the PPII helix rods through the linker.

According to further another aspect of the present disclosure, a method for manufacturing the aforementioned protein modulator includes steps as follows. A polygonal scaffold is provided, at least one ligand-providing compound is provided, and a conjugation step is provided. The polygonal scaffold includes at least three PPII helix rods and at least three connectors. Each of the PPII helix rods is composed of a plurality of repeat units represented by Formula (i):

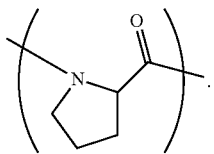

At least one of the PPII helix rods has at least one of hydrogen atoms of at least one of the repeat units being substituted by a first chemical handle for connecting the ligand. Each of the connectors is a divalent organic group, and every two of the PPII helix rods are connected by one of the connectors to form a closed ring. The ligand-providing compound includes the ligand and a second chemical handle, and the ligand is connected with the second chemical handle. In the conjugation step, the first chemical handle of the PPII helix rod is reacted with the second chemical handle of the ligand-providing compound to form the linker, thus the ligand is connected with one of the PPII helix rods through the linker.

BRIEF DESCRIPTION OF THE DRAWINGS

The present disclosure can be more fully understood by reading the following detailed description of the embodiment, with reference made to the accompanying drawings as follows:

FIG. 7A is a schematic view exemplarily illustrating Step 210 in FIG. 5;

FIG. 7B is a schematic view exemplarily illustrating Step 221 in FIG. 6;

FIG. 7C is a schematic view exemplarily illustrating Step 222 in FIG. 6;

FIG. 10A is a schematic view exemplarily illustrating Step 410 in FIG. 9;

FIG. 10B is a schematic view exemplarily illustrating Step 420 in FIG. 9;

FIG. 10C is a schematic view exemplarily illustrating Step 430 in FIG. 9;

DETAILED DESCRIPTION

The term "Xaa" represents different derivatives of proline, and the derivatives of proline is summarized in Table 1.

TABLE 1

| Derivative | Structural formula |
| --- | --- |
| 1 | |

TABLE 1-continued

| Derivative | Structural formula |
|---|---|
| 2 | 4-NHAlloc proline |
| 3 | 4-O-CH2-CHO proline |
| 4 | 4-NH2 proline |
| 5 | 4-NH-C(O)-CH2CH2-C≡CH proline |
| 6 | 4-O-(CH2)3-S-CH2CH2-O-mannose proline |
| 7 | 4-O-CH2CH2-NH-CH2CH2-O-mannose proline |
| 8 | 4-NH-C(O)-CH2CH2-triazole-CH2CH2-O-mannose proline |
| 9 | 4-NH-C(O)-CH2CH2-triazole-CH2CH2-O-GlcNAc proline |
| 10 | 4-X proline |
| 11 | N-Fmoc proline |

TABLE 1-continued

| Derivative | Structural formula |
|---|---|
| 12 | 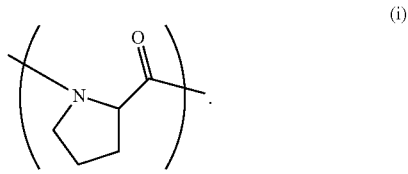 |
| 13 | |
| 14 | |
| 15 | |
| 16 | |
| 17 | |
| 18 | |

Polygonal Scaffold

A polygonal scaffold includes at least three PPII helix rods and at least three connectors. Each of the PPII helix rods is composed of a plurality of repeat units represented by Formula (i):

$$\left(\begin{array}{c}\text{(i)}\end{array}\right)$$

At least one of the PPII helix rods has at least one of hydrogen atoms of at least one of the repeat units being substituted by a first chemical handle for connecting a ligand. Each of the connectors is a divalent organic group, and every two of the PPII helix rods are connected by one of the connectors to form a closed ring.

Figure 1:
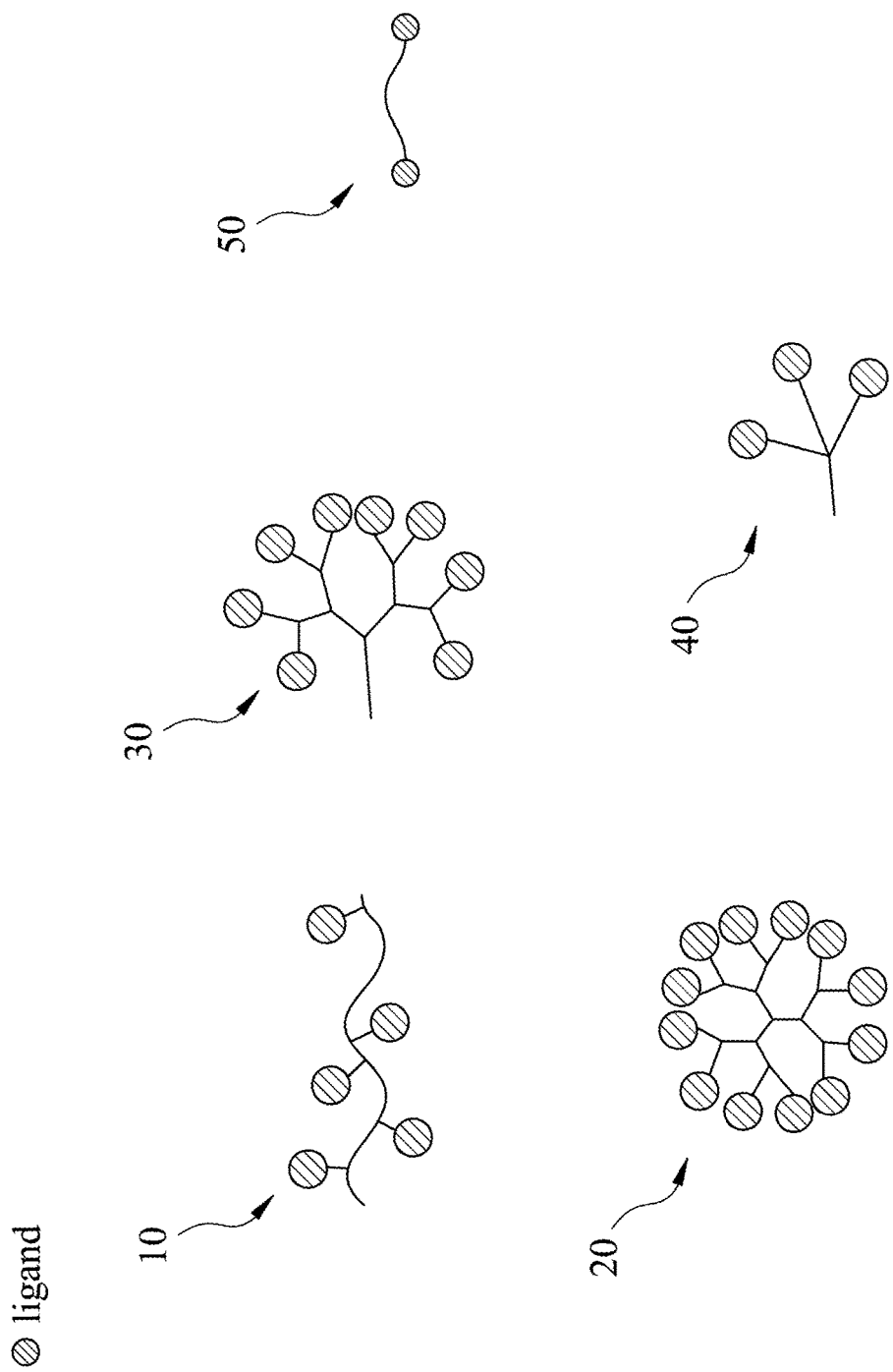
FIG. 1 shows conventional scaffolds bearing multiple ligands.
Figure 2A:
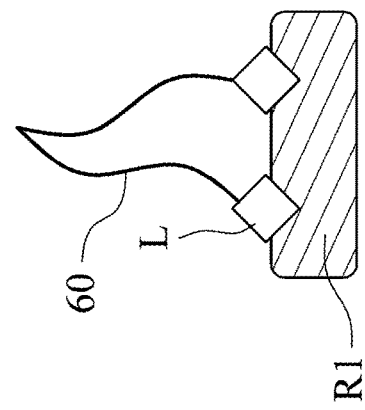
FIG. 2A shows an interaction between a flexible scaffold and a receptor.
Figure 2B:
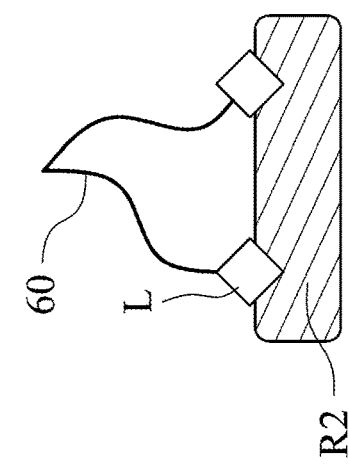
FIG. 2B shows an interaction between the flexible scaffold in FIG. 2A and another receptor.
Figure 2C:
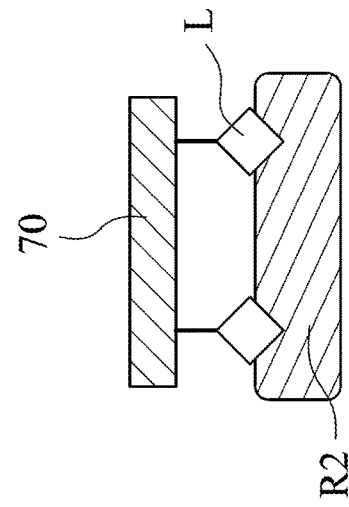
FIG. 2C shows an interaction between a rigid scaffold and the receptor in FIG. 2B.
Figure 3A:
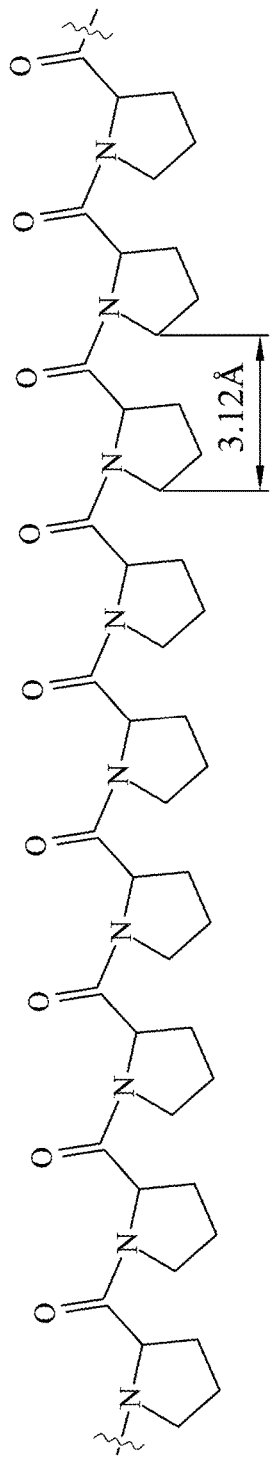
FIG. 3A shows a structural formula of a PPII helix rod having amino acid sequence referenced as SEQ ID NO: 44.
Figure 3B:
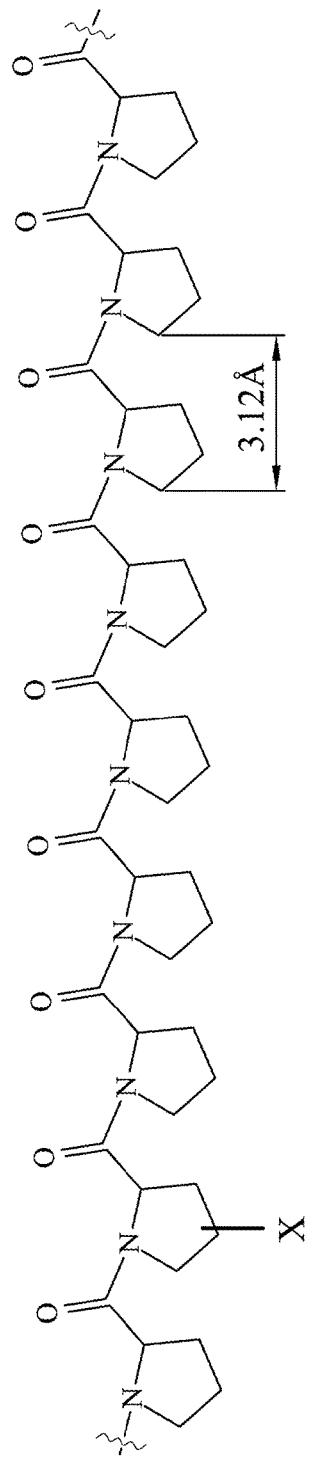
FIG. 3B shows a structural formula of a substituted PPII helix rod having amino acid sequence referenced as SEQ ID NO: 45.
Figure 3C:
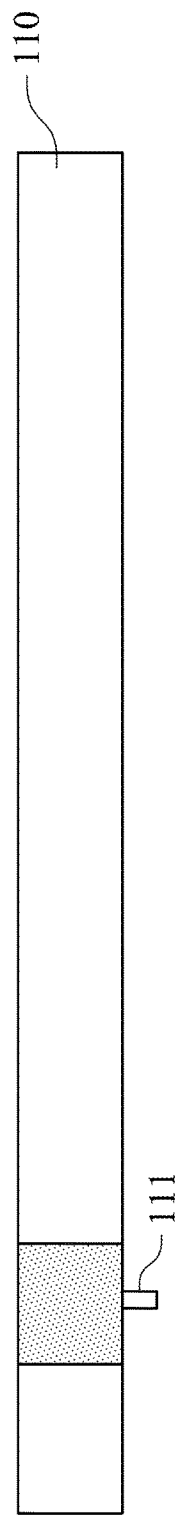
FIG. 3C shows a schematic diagram of the substituted PPII helix rod in FIG. 3B.

FIG. 3A shows a structural formula of a PPII helix rod, wherein the amino acid sequence of the PPII helix rod in FIG. 3A is referenced as SEQ ID NO: 44. FIG. 3B shows a structural formula of a substituted PPII helix rod, wherein the amino acid sequence of the substituted PPII helix rod in FIG. 3B is referenced as SEQ ID NO: 45, and Xaa at residue 2 is the derivative 10 of proline. FIG. 3C shows a schematic diagram of the substituted PPII helix rod in FIG. 3B. In FIG. 3A, the PPII helix rod is composed of nine repeat units represented by Formula (i), no hydrogens of the repeat units are substituted. In FIG. 3B, the PPII helix rod is composed of nine repeat units represented by Formula (i), wherein a hydrogen of the second repeat unit counted from left is substituted by the first chemical handle X for connecting a ligand (not shown). In the embodiment, the number of the repeat units, the position and the number of the repeat unit with the first chemical handle X are only exemplary and can be adjusted according to practical needs. In FIG. 3C, the PPII helix rod 110 is depicted as a long rod and the repeat unit with the first chemical handle 111 (i.e. X) is depicted as a section on the long rod, which is for the sake of simplicity, and the expression will continue to be used hereinafter. As shown in FIGS. 3A and 3B, the PPII helix rod is a peptide composed of proline (i.e. the repeat unit). With the uniform composition (only proline), the PPII helix rods has a stable helical structure under aqueous conditions, which is favorable for pharmaceutical use, and a desired rigidity can be provided. Moreover, a length of the PPII helix rod can be well-defined. As shown in FIGS. 3A and 3B, every proline extends the length of the PPII helix rod about 3.12 Å. Furthermore, the helical structure of the PPII helix rod can be maintained even attaches with a plurality of the first chemical handles X, which is favorable for connecting with ligands and display ligands at specific distance with 1-dimensional control along the PPII helix rod.

Figure 4:
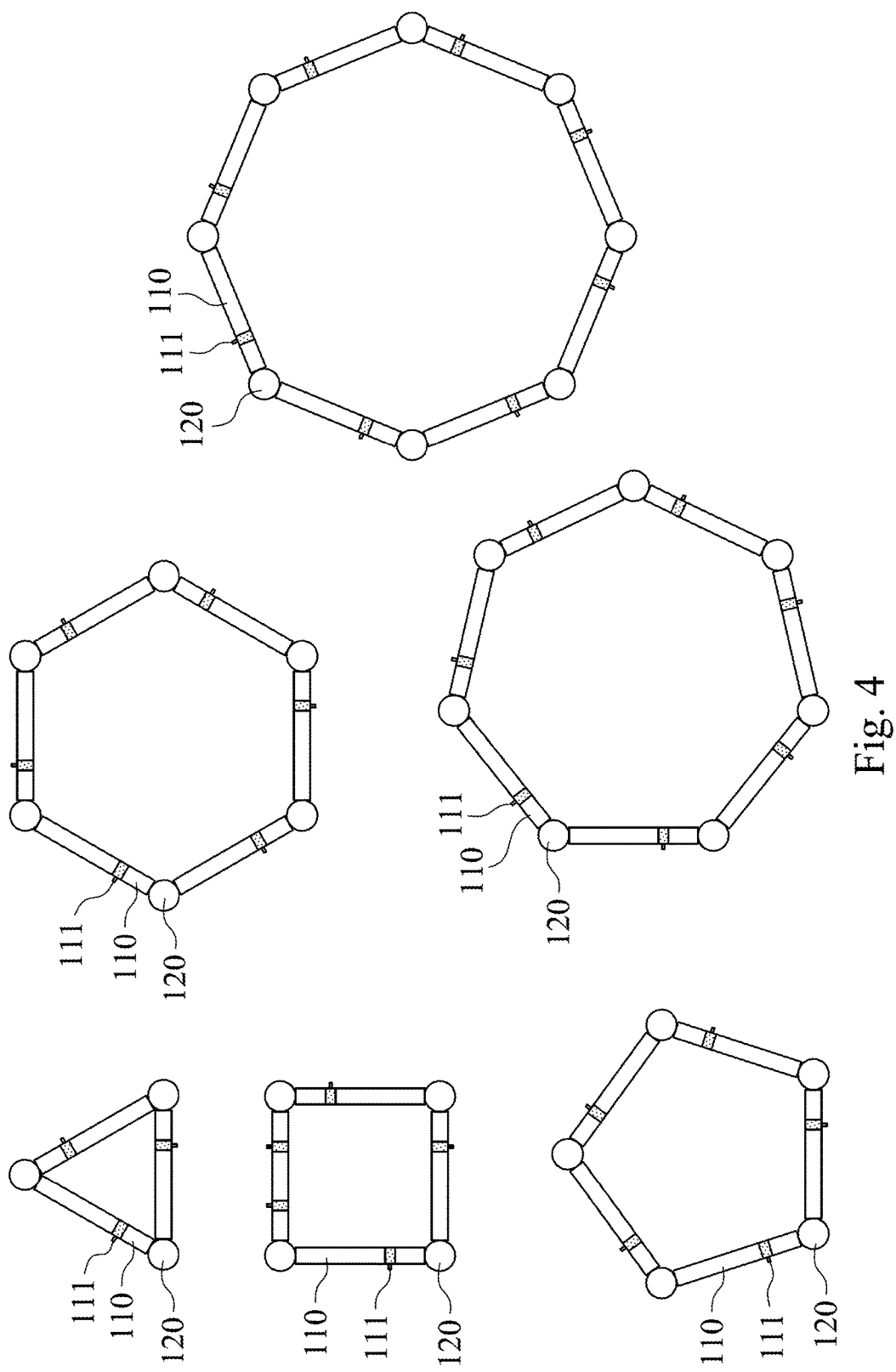
FIG. 4 is a schematic view showing a plurality of polygonal scaffolds according to another embodiment of the present disclosure.

FIG. 4 is a schematic view showing a plurality of polygonal scaffolds according to another embodiment of the present disclosure. As shown in FIG. 4, from top to bottom and from left to right, the closed ring formed by the PPII helix rods 110 and the connectors 120 can be a triangle, a quadrangle, a pentagon, a hexagon, a heptagon or an octagon. Moreover, the position and the number of the repeat unit with the first chemical handle 111 are adjustable. Therefore, the polygonal scaffold according to the present disclosure has advantages as follows. First, the polygonal scaffold forms a plane which is correspondent to the surface of a cell membrane. Accordingly, an excellent spatial correspondence between the polygonal scaffold and the membrane proteins can be provided. Second, the ligand attachment site (i.e., the location of the first chemical handle 111) can be adjusted, so that the location of the ligands can be precisely controlled and can be tailor made for the target proteins on the cell membrane. Third, the polygonal scaffold is relatively rigid due to PPII helix rods 110 and the polygonal structure. As a result, an excellent spatial selectivity can be provided by the polygonal scaffold, and the affinity between the ligands (not shown) attached on the polygonal scaffold and the target membrane proteins can be enhanced significantly.

According to the polygonal scaffold of the present disclosure, a number of the repeat units of each of the PPII helix rods can be 6 to 18, so that the length of the PPII helix rods is proper, which is favorable for maintaining the helical structure and the rigidity thereof.

According to the polygonal scaffold of the present disclosure, the first chemical handle can have a structure represented by Formula (ii-1), Formula (ii-2), Formula (ii-3), Formula (ii-4), Formula (ii-5) or Formula (ii-6):

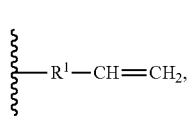
(ii-1)

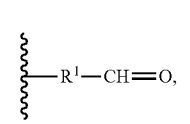
(ii-2)

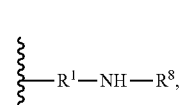
(ii-3)

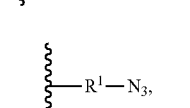
(ii-4)

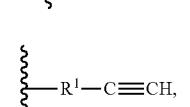
(ii-5)

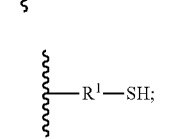
(ii-6)

wherein $R^1$ is independently a single bond or a divalent hydrocarbon group having 1 to 6 carbon atoms, each of —$CH_2$— of the divalent hydrocarbon group is unsubstituted or substituted by —O—, —NH— or —CO—, and $R^8$ is a protecting group or H. The protecting group can be an Alloc group, a Troc group or a Cbz group. The Alloc group can have a structure represented by Formula (vii-1), the Troc group can have a structure represented by Formula (vii-2), and the Cbz group can have a structure represented by Formula (vii-3):

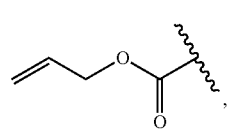
(vii-1)

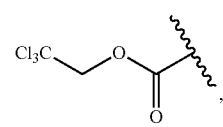
(vii-2)

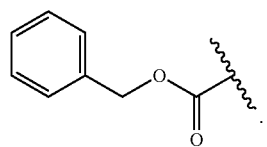
(vii-3)

The first chemical handle can have a structure represented by Formula (ii-1-1), Formula (ii-2-1), Formula (ii-3-1) or Formula (ii-5-1):

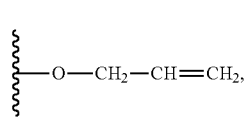
(ii-1-1)

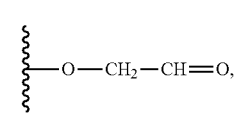
(ii-2-1)

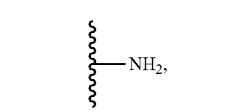
(ii-3-1)

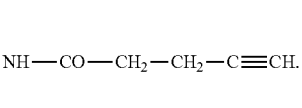
(ii-5-1)

According to the polygonal scaffold of the present disclosure, the connector can have a structure represented by Formula (iii-1):

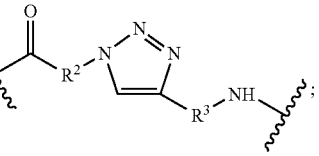
(iii-1)

wherein $R^2$ and $R^3$ are independently a single bond or a divalent hydrocarbon group having 1 to 6 carbon atoms. For example, the connector can have a structure represented by Formula (iii-1-1), Formula (iii-1-2), Formula (iii-1-3), Formula (iii-1-4), Formula (iii-1-5) or Formula (iii-1-6):

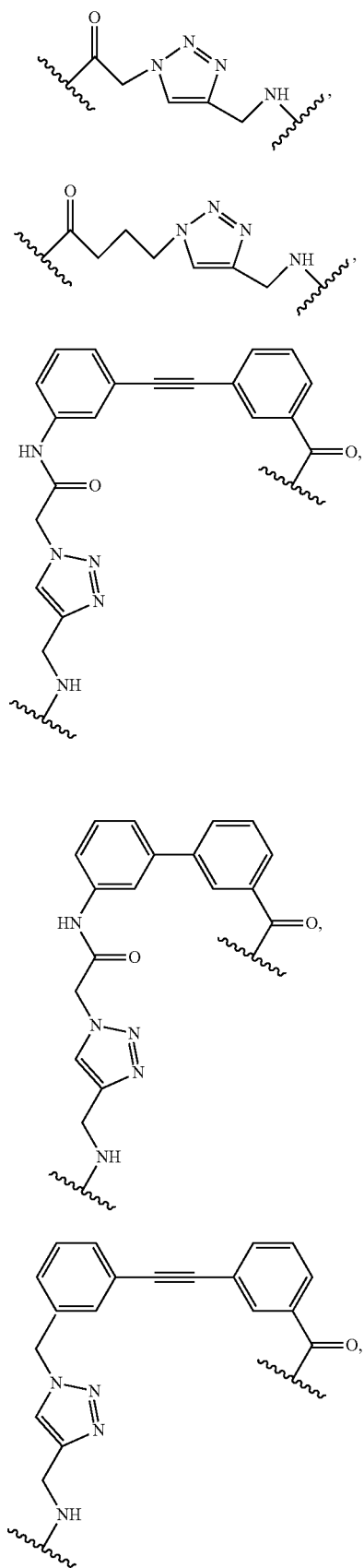

Method for Manufacturing Polygonal Scaffold

Figure 5:
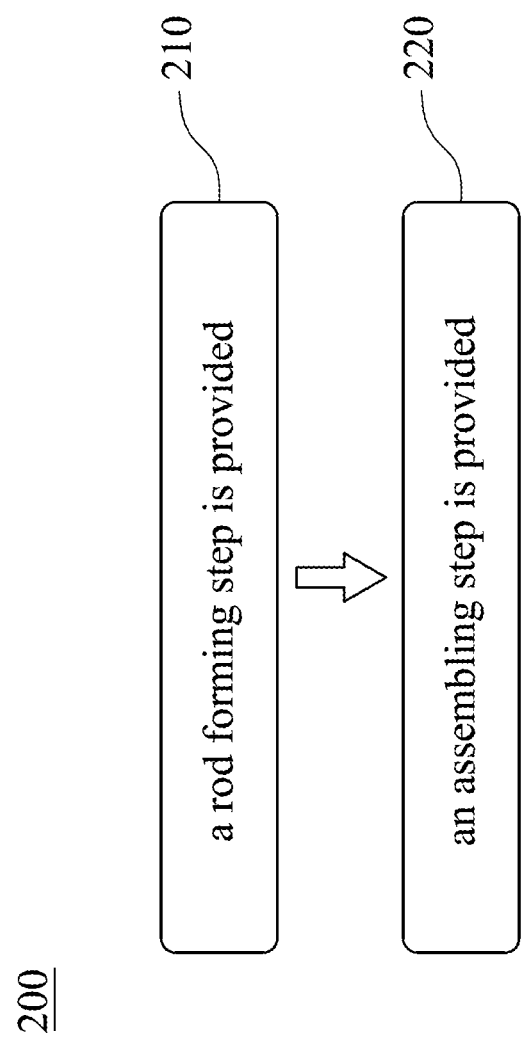
FIG. 5 is a flow diagram showing a method for manufacturing the polygonal scaffold according to further another embodiment of the present disclosure.

FIG. 5 is a flow diagram showing a method 200 for manufacturing the polygonal scaffold according to further another embodiment of the present disclosure. In FIG. 5, the method 200 includes Step 210 and Step 220.

In Step 210, a rod forming step is provided, wherein the PPII helix rods are formed. For example, the rod forming step can be conducted by a solid-phase peptide synthesis (SPPS) process.

In Step 220, an assembling step is provided, wherein every two of the PPII helix rods are connected by one of the connectors to form the closed ring.

Figure 6:
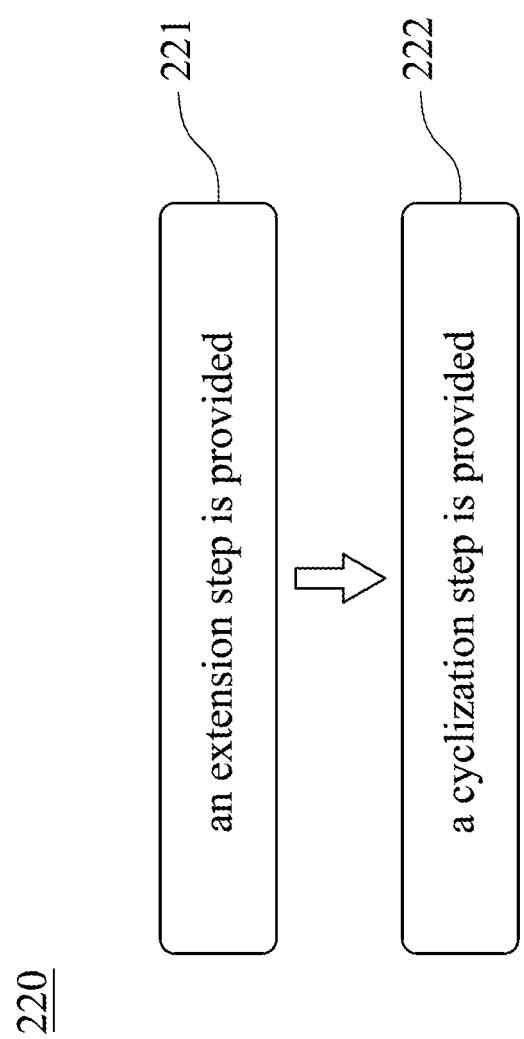
FIG. 6 is a flow diagram showing Step 220 of the method in FIG. 5.

FIG. 6 is a flow diagram showing Step 220 of the method in FIG. 5. In FIG. 6, Step 220 includes Step 221 and Step 222.

In Step 221, an extension step is provided, wherein every two of the PPII helix rods are connected by one of the connectors to form a linear chain. For example, the extension step can be conducted by a Cu(I)-catalyzed azide-alkyne cycloaddition (CuAAC) in solid-phase.

In Step 222, a cyclization step is provided, wherein two ends of the linear chain are connected by one of the connectors to form the closed ring. For example, the cyclization step can be conducted by a CuAAC in solution-phase.

FIG. 7A is a schematic view exemplarily illustrating Step 210 in FIG. 5, FIG. 7B is a schematic view exemplarily illustrating Step 221 in FIG. 6 and FIG. 7C is a schematic view exemplarily illustrating Step 222 in FIG. 6. In FIGS. 7A-7C, the polygonal scaffold is a triangle, while other polygonal scaffolds can be manufactured in a similar way and will not be described herein. In FIG. 7A, PPII helix rod 310, PPII helix rod 320 and PPII helix rod 330 are formed, which is correspondent to Step 210 in FIG. 5. The PPII helix rod 310 has a first chemical handle 311, the PPII helix rod 320 has a first chemical handle 321 and the PPII helix rod 330 has a first chemical handle 331. The position of the first chemical handle 311 on the PPII helix rod 310, the position of the first chemical handle 321 on the PPII helix rod 320, and the position of the first chemical handle 331 on the PPII helix rod 330 are different in this embodiment. However, in other embodiments, the positions of the first chemical handles can be the same. The kinds of the first chemical handle 311, the first chemical handle 321 and the first chemical handle 331 can be the same or different. In FIG. 7B, the PPII helix rod 310 and the PPII helix rod 320 are connected by a connector 340, and the PPII helix rod 320 and the PPII helix rod 330 are connected by another connector 340 to form a linear chain, which is correspondent to Step 221 in FIG. 6. In FIG. 7C, two ends of the linear chain are connected by further another connector 340 to form a closed ring, which is correspondent to Step 222 in FIG. 6.

Protein Modulator

According to present disclosure, a protein modulator is provided. The protein modulator is obtained from the aforementioned polygonal scaffold. Specifically, the protein modulator includes a polygonal scaffold and at least one ligand. The polygonal scaffold includes at least three PPII helix rods and at least three connectors. Each of the PPII helix rods is composed of a plurality of repeat units represented by Formula (i):

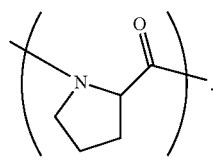
(i)

At least one of the PPII helix rods has at least one of hydrogen atoms of at least one of the repeat units being substituted by a linker. Each of the connectors is a divalent organic group, and every two of the PPII helix rods are connected by one of the connectors to form a closed ring. The ligand is connected with one of the PPII helix rods through the linker.

Figure 8:
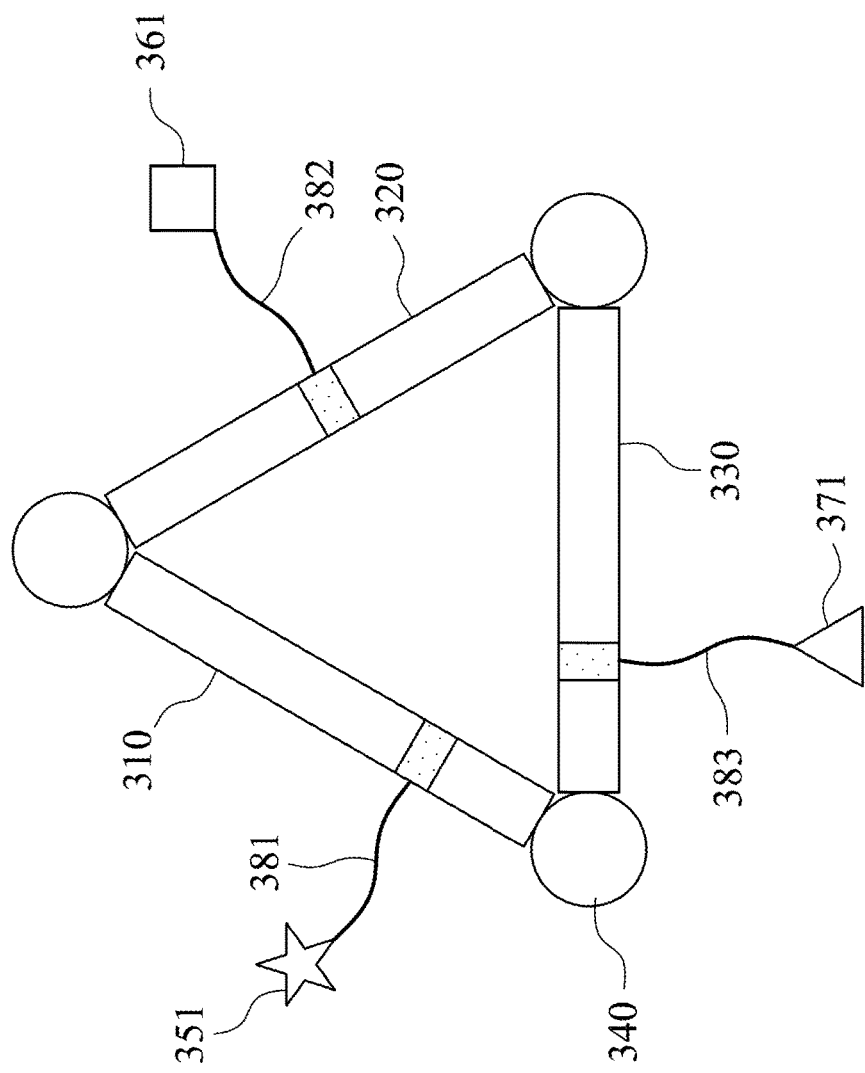
FIG. 8 is a schematic view showing a protein modulator according to yet another embodiment of the present disclosure.

FIG. 8 is a schematic view showing a protein modulator according to yet another embodiment of the present disclosure. In FIG. 8, the protein modulator includes a polygonal scaffold (its reference numeral is omitted) and three ligands, which are ligand 351, ligand 361 and ligand 371. The polygonal scaffold includes a PPII helix rod 310 with a linker 381, a PPII helix rod 320 with a linker 382 and a PPII helix rod 330 with a linker 383. Every two of the PPII helix rod 310, the PPII helix rod 320 and the PPII helix rod 330 are connected by one of the connectors 340 to form a closed ring (a triangle in this embodiment). The ligand 351 is connected with the PPII helix rods 310 through the linker 381, the ligand 361 is connected with the PPII helix rod 320 through the linker 382, and the ligand 371 is connected with the PPII helix rod 330 through the linker 383. With the polygonal scaffold, the ligand 351, the ligand 361 and the ligand 371 are linked to a plane, which is correspondent to the surface of a cell membrane (not shown). Moreover, the ligand attachment site (i.e., the location of the linker 381, the linker 382 and the linker 383) can be adjusted, so that the location of the ligand 351, the ligand 361 and the ligand 371 can be precisely controlled and can be tailor made for the target proteins on the cell membrane. Furthermore, the polygonal scaffold is relatively rigid due to PPII helix rods (310, 320 and 330) and the polygonal structure. Therefore, an excellent spatial selectivity can be provided by the protein modulator, and the affinity between the ligands (351, 361 and 371) and the target proteins on the cell membrane can be enhanced significantly.

According to the protein modulator of the present disclosure, the linker can have a structure represented by Formula (vi-1), Formula (vi-2) or Formula (vi-3):

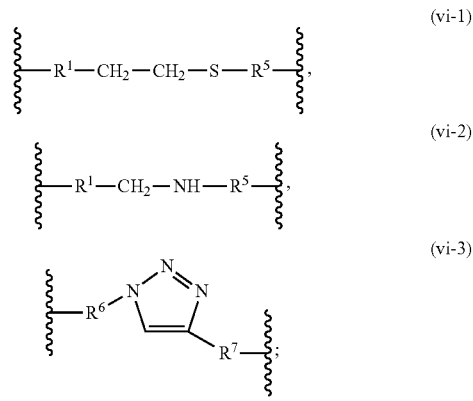

wherein $R^1$, $R^5$, $R^6$ and $R^7$ are independently a single bond or a divalent hydrocarbon group having 1 to 6 carbon atoms, and each of —$CH_2$— of the divalent hydrocarbon group is unsubstituted or substituted by —O—, —NH— or —CO—.

According to the protein modulator of the present disclosure, the ligand can have a structure represented by Formula (iv-1-1), Formula (iv-2-1), Formula (iv-3-1), Formula (iv-4-1), Formula (iv-5-1), Formula (iv-6-1) or Formula (iv-7-1):

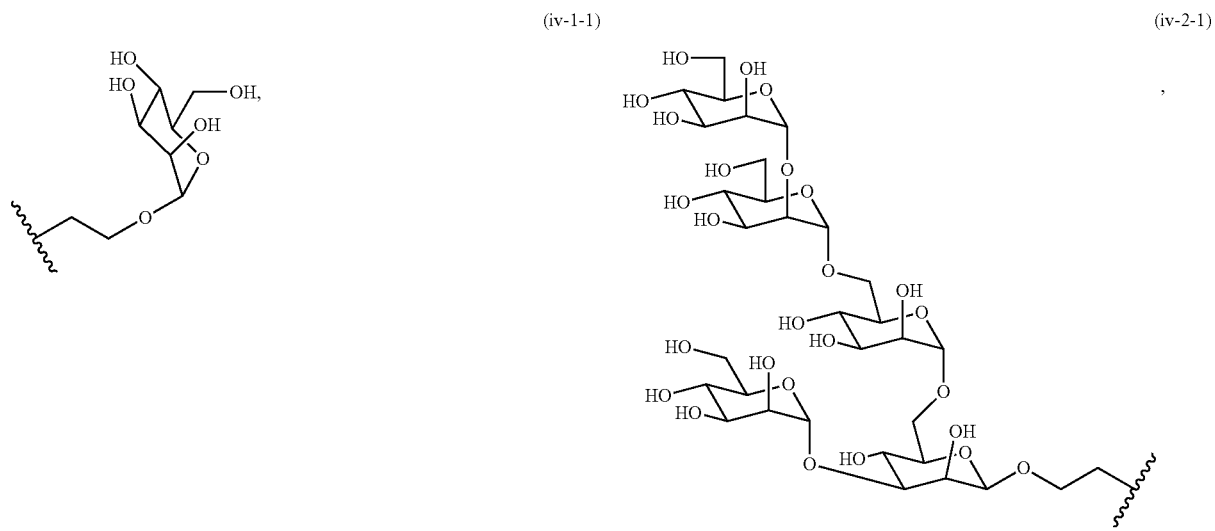

-continued
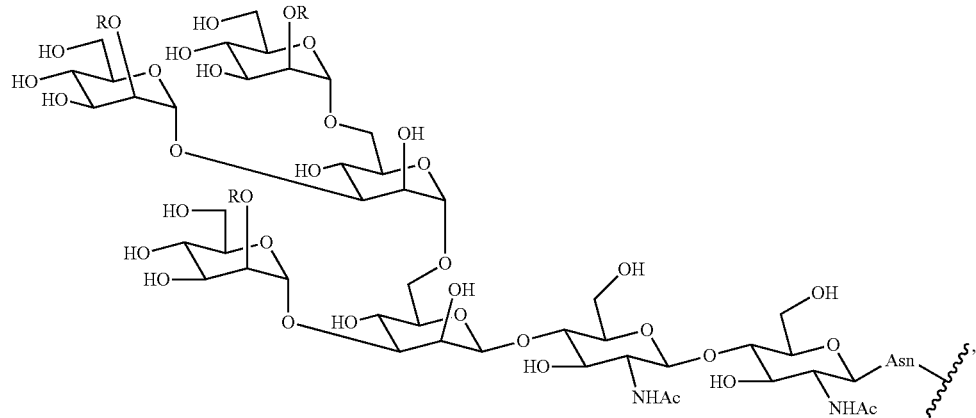
(iv-3-1)
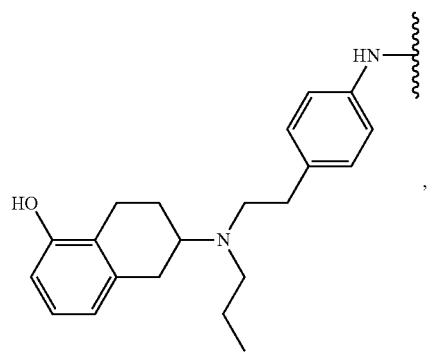
(iv-4-1)
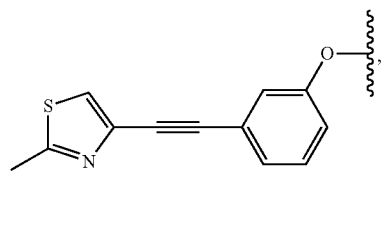
(iv-5-1)
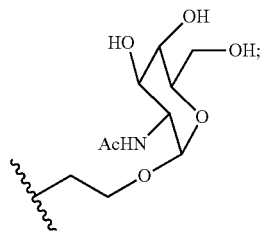
(iv-6-1)
(iv-7-1)
wherein R is H or α 1-2 Man, wherein α 1-2 Man has a structure as follows:
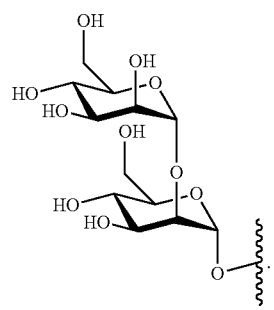
(α 1-2 Man)
For example, the ligand can have a structure represented by Formula (iv-3-1a):

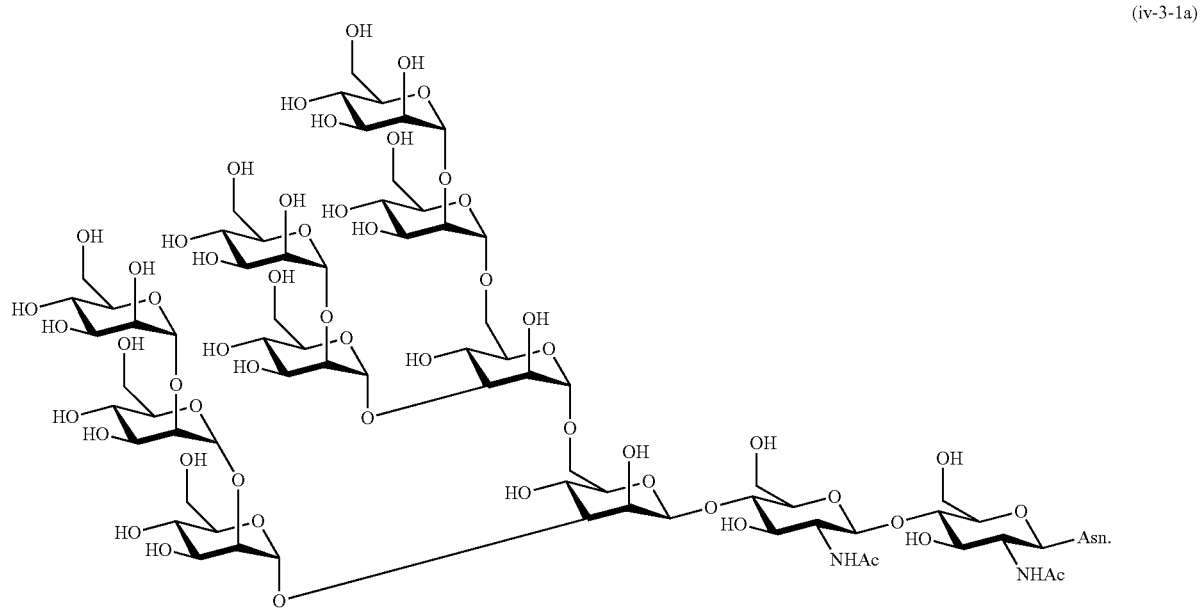

(iv-3-1a)

According to the protein modulator of the present disclosure, the details of the connectors have been mentioned above, and will not be described herein.

Method for Manufacturing Protein Modulator

Figure 9:
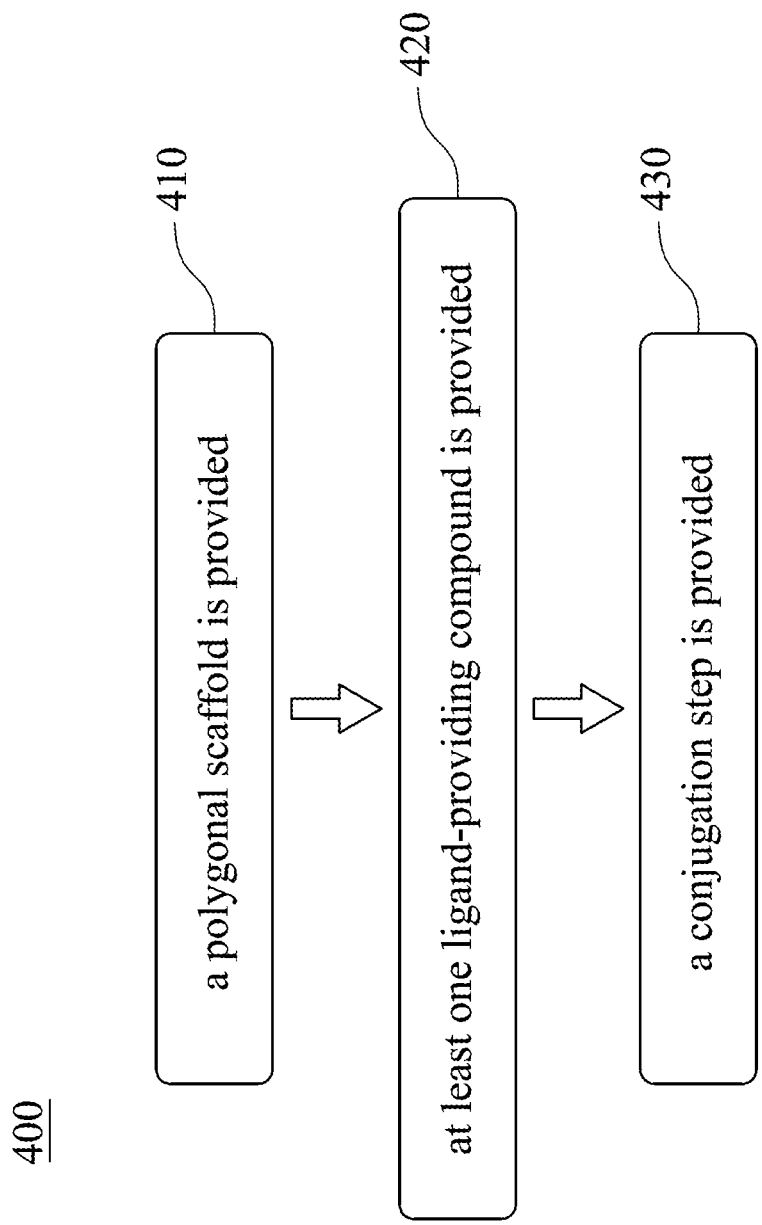
FIG. 9 is a flow diagram showing a method for manufacturing the protein modulator according to yet another embodiment of the present disclosure.

FIG. 9 is a flow diagram showing a method 400 for manufacturing the protein modulator according to yet another embodiment of the present disclosure. In FIG. 9, the method 400 includes Step 410, Step 420 and Step 430.

In Step 410, a polygonal scaffold is provided. The polygonal scaffold includes at least three PPII helix rods and at least three connectors, every two of the PPII helix rods are connected by one of the connectors to form a closed ring, and at least one of the PPII helix rods includes at least one first chemical handle. The details of the polygonal scaffold have been mentioned above, and will not be described herein.

In Step 420, at least one ligand-providing compound is provided, wherein the ligand-providing compound includes the ligand and a second chemical handle, and the ligand is connected with the second chemical handle.

For example, the ligand-providing compound can have a structure represented by Formula (iv-1), Formula (iv-2), Formula (iv-3), Formula (iv-4), Formula (iv-5), Formula (iv-6) or Formula (iv-7):

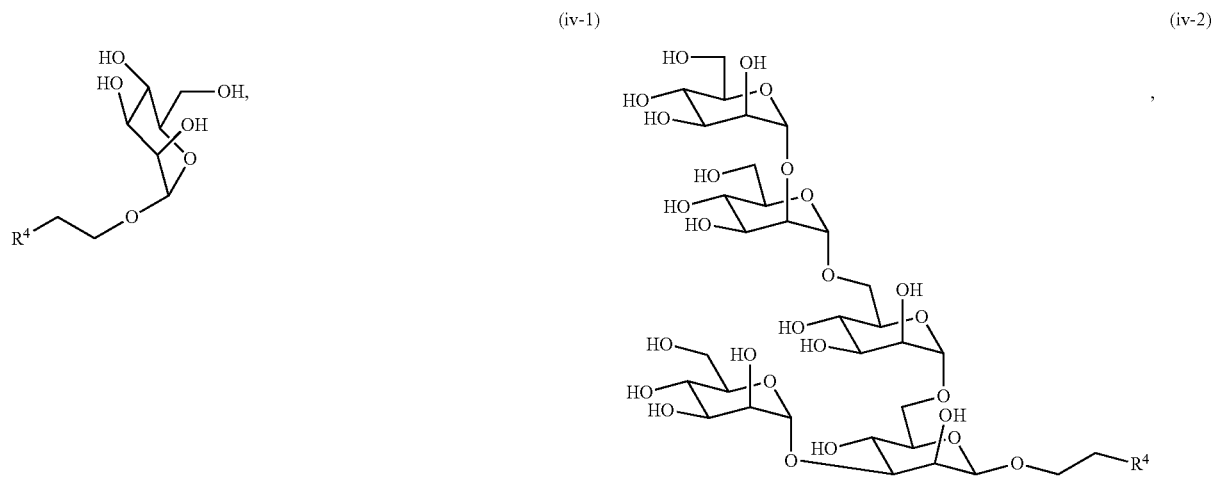

-continued

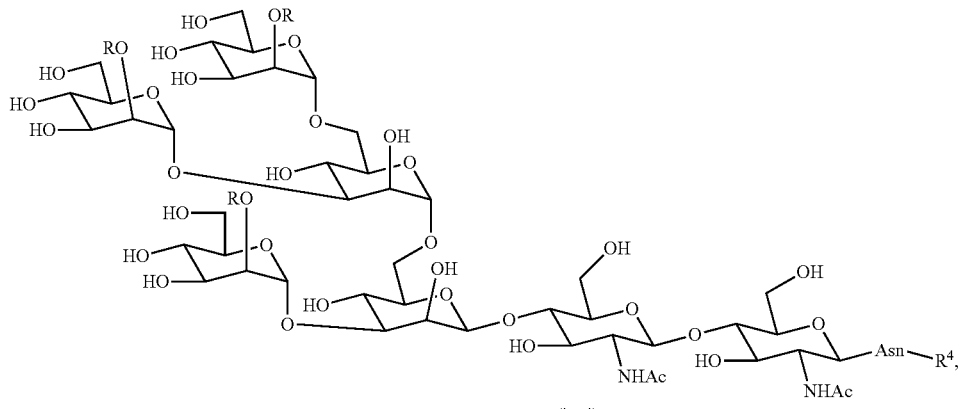
(iv-3)

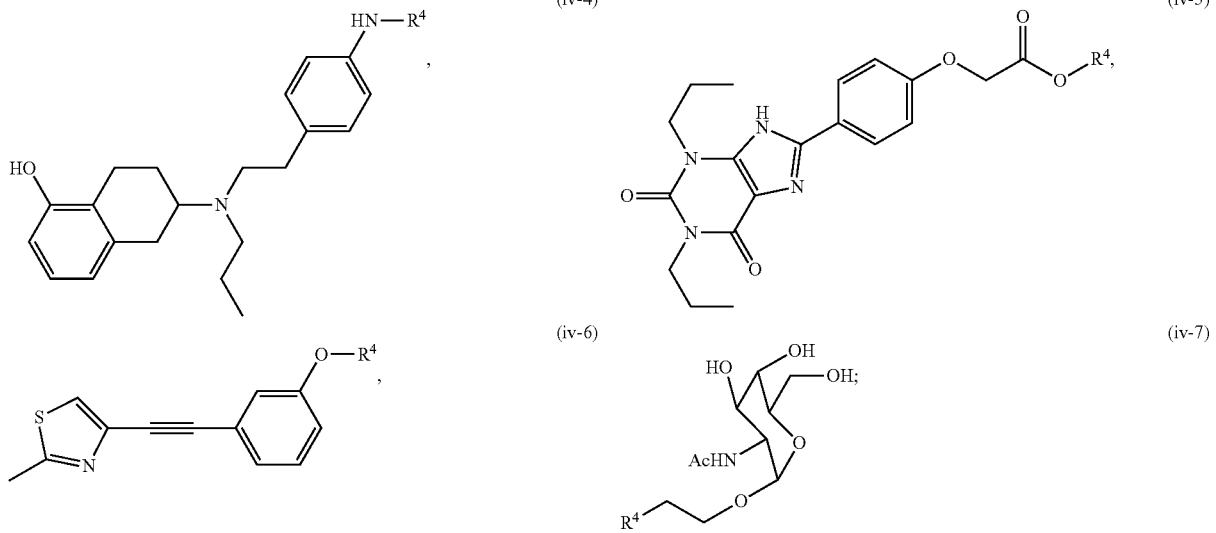
(iv-4)

(iv-5)

(iv-6)

(iv-7)

wherein R⁴ is the second chemical handle for reacting with the first chemical handle of each of the PPII helix rods, and R is H or a 1-2 Man.

R⁴ can have a structure represented by Formula (v-1), Formula (v-2), Formula (v-3), Formula (v-4) or Formula (v-5):

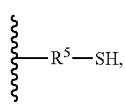
(v-1)

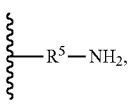
(v-2)

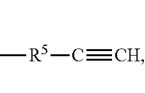
(v-3)

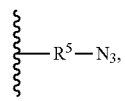
(v-4)

-continued

(v-5)

wherein R⁵ is independently a single bond or a divalent hydrocarbon group having 1 to 6 carbon atoms, and each of —CH₂— of the divalent hydrocarbon group is unsubstituted or substituted by —O—, —NH— or —CO—.

R⁴ can have the structure represented by Formula (v-1-1), Formula (v-2-1), Formula (v-3-1) or Formula (v-4-1):

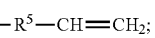
(v-1-1)

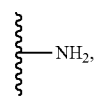
(v-2-1)

-continued

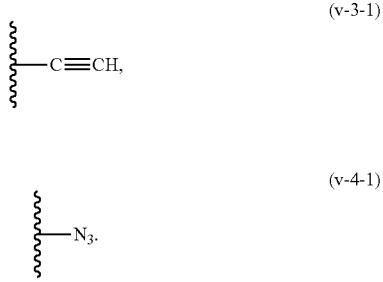

(v-3-1)

(v-4-1)

In Step 430, a conjugation step is provided, wherein the first chemical handle of the PPII helix rod is reacted with the second chemical handle of the ligand-providing compound to form the linker, thus the ligand is connected with one of the PPII helix rods through the linker.

FIG. 10A is a schematic view exemplarily illustrating Step 410 in FIG. 9. FIG. 10B is a schematic view exemplarily illustrating Step 420 in FIG. 9. FIG. 10C is a schematic view exemplarily illustrating Step 430 in FIG. 9. In FIGS. 10A-10C, the polygonal scaffold of the protein modulator is a triangle, while other polygonal scaffolds can be manufactured in a similar way and will not be described herein. In FIG. 10A, the polygonal scaffold is provided, which is correspondent to Step 410 in FIG. 9. The polygonal scaffold is the same as that in FIG. 7C, and the details thereof will not be repeated herein. In FIG. 10B, three ligand-providing compounds, the ligand-providing compound 350, the ligand-providing compound 360 and the ligand-providing compound 370, are provided, which is correspondent to Step 420 in FIG. 9. The ligand-providing compound 350 includes a ligand 351 and a second chemical handle 352, the ligand-providing compound 360 includes a ligand 361 and a second chemical handle 362, and the ligand-providing compound 370 includes a ligand 371 and a second chemical handle 372. In FIG. 10C, a conjugation step is provided, which is correspondent to Step 430 in FIG. 9, wherein the first chemical handle 311 is reacted with the second chemical handle 352 to form the linker 381, the first chemical handle 321 is reacted with the second chemical handle 362 to form the linker 382, and the first chemical handle 331 is reacted with the second chemical handle 372 to form the linker 383. Thus, the ligand 351 is connected with the PPII helix rod 310 through the linker 381, the ligand 361 is connected with the PPII helix rod 320 through the linker 382, and the ligand 371 is connected with the PPII helix rod 330 through the linker 383. In FIG. 10A, each of the PPII helix rods (310, 320, 330) includes a first chemical handle (311, 321, 331), which is only exemplary and the present disclosure is not limited thereto. In other embodiments, the number of PPII helix rod including the first chemical handle can be one or two, and the number of the first chemical handle on a same PPII helix rod can be greater than one. Moreover, the number of the PPII helix rods of the scaffold can be greater than three.

According to the present disclosure, the term "chemical handle" refers to a monovalent organic group including an active group or a protected active group. Preferably, the active group or the protected active group is located at the terminal end of the monovalent organic group. Specifically, the polygonal scaffold includes the first chemical handle, and the ligand-providing compound includes the second chemical handle. When the conjugation step is conducted, the active group of the first chemical handle reacts with the active group of the second chemical handle to form the linker, so that the ligand can be connected with one of the PPII helix rods through the linker. When the monovalent organic group includes the protected active group, a deprotection step should be conducted before conducting the conjugation step.

Figure 11:
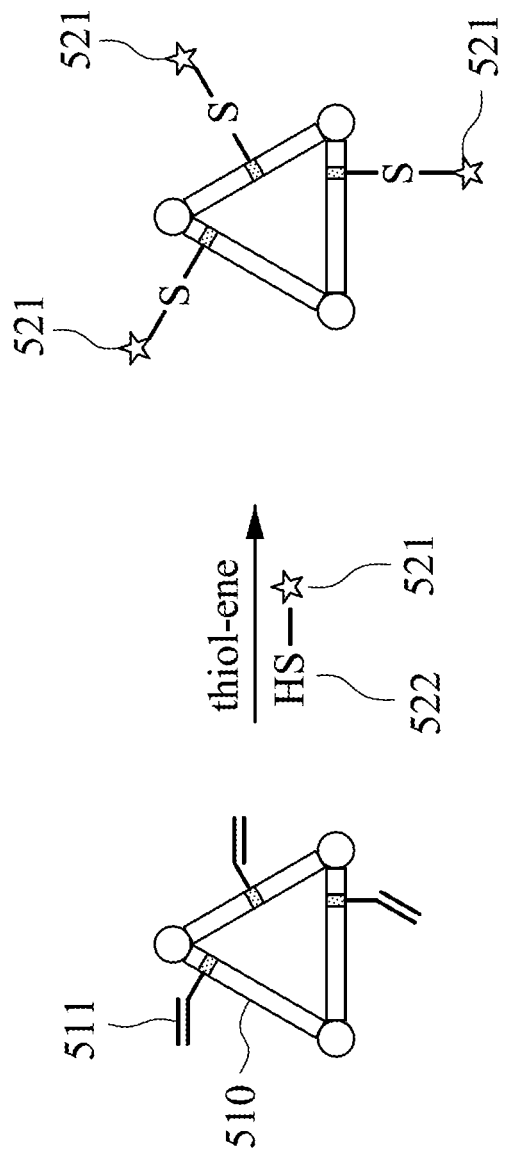
FIG. 11 is a schematic view showing a conjugation step according to yet another embodiment of the present disclosure.

FIG. 11 is a schematic view showing the conjugation step according to yet another embodiment of the present disclosure. In FIG. 11, the conjugation step can be conducted by a thiol-ene reaction. Specifically, the first chemical handle 511 includes a terminal ethylene group. The other portion of the first chemical handle 511 is omitted for conciseness. That is, there can have a linker between the terminal ethylene group and the PPII helix rod 510. The linker can be a divalent organic group, such as a divalent hydrocarbon group having 1 to 6 carbon atoms, and each of —$CH_2$— of the divalent hydrocarbon group is unsubstituted or substituted. The second chemical handle 522 includes a terminal thiol group. The other portion of the second chemical handle 522 is omitted for conciseness, that is, there can have a linker between the terminal thiol group and the ligand 521, and the linker can be the same as the linker between the terminal ethylene group and the PPII helix rod 510. As shown in FIG. 11, the ligand 521 can be connected with the PPII helix rod 510 through the thiol-ene reaction.

Figure 12:
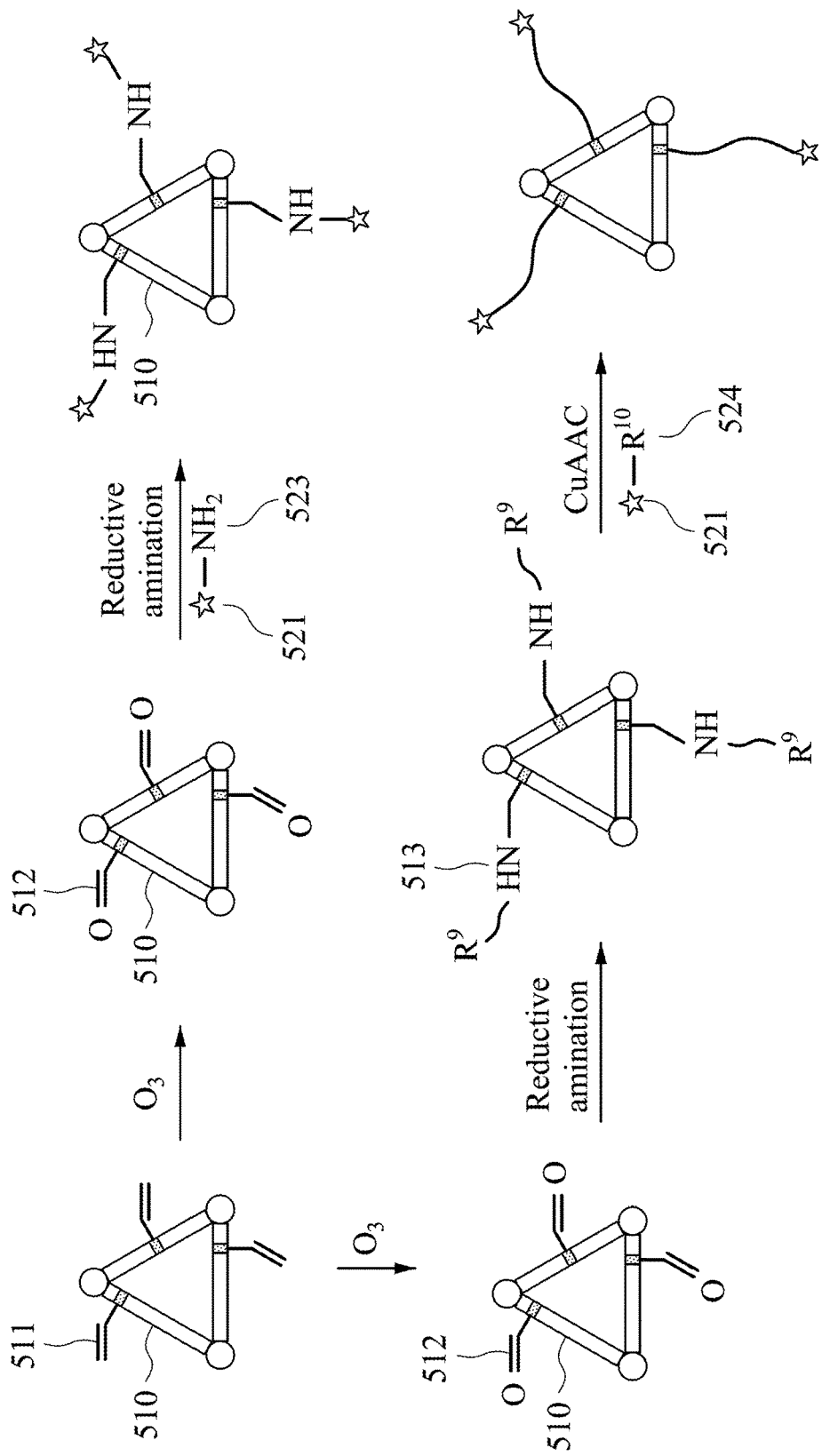
FIG. 12 is a schematic view showing the conjugation step according to yet another embodiment of the present disclosure.

FIG. 12 is a schematic view showing the conjugation step according to yet another embodiment of the present disclosure. In FIG. 12, the conjugation step can be conducted by a reductive amination reaction, or a reductive amination reaction followed by a CuAAC in solution-phase. Specifically, the terminal ethylene group of the first chemical handle 511 can be transformed into another first chemical handle 512 with a terminal aldehyde group. The second chemical handle 523 includes a terminal amino group (—$NH_2$). The other portion of the second chemical handle 523 is omitted for conciseness, that is, there can have a linker between the terminal amino group and the ligand 521, and the linker can be the same as the linker between the terminal ethylene group and the PPII helix rod 510 in FIG. 11. The ligand 521 can be connected with the PPII helix rod 510 through a reductive amination reaction as shown in the upper part of FIG. 12. Alternatively, the first chemical handle 512 can first undergo a reductive amination reaction to be transformed into another first chemical handle 513, which includes a medium group NH and a terminal group $R^9$. The other portion of the first chemical handle 513 is omitted for conciseness, that is, there can have a linker between the terminal group $R^9$ and the medium group NH, and there can have another linker between the medium group NH and the PPII helix rod 510. The second chemical handle 524 includes a terminal group $R^{10}$. One of $R^9$ and $R^{10}$ is an alkyne group, and the other is an azide group, so that the ligand 521 can be connected with the PPII helix rod 510 through the CuAAC in solution-phase.

Figure 13:
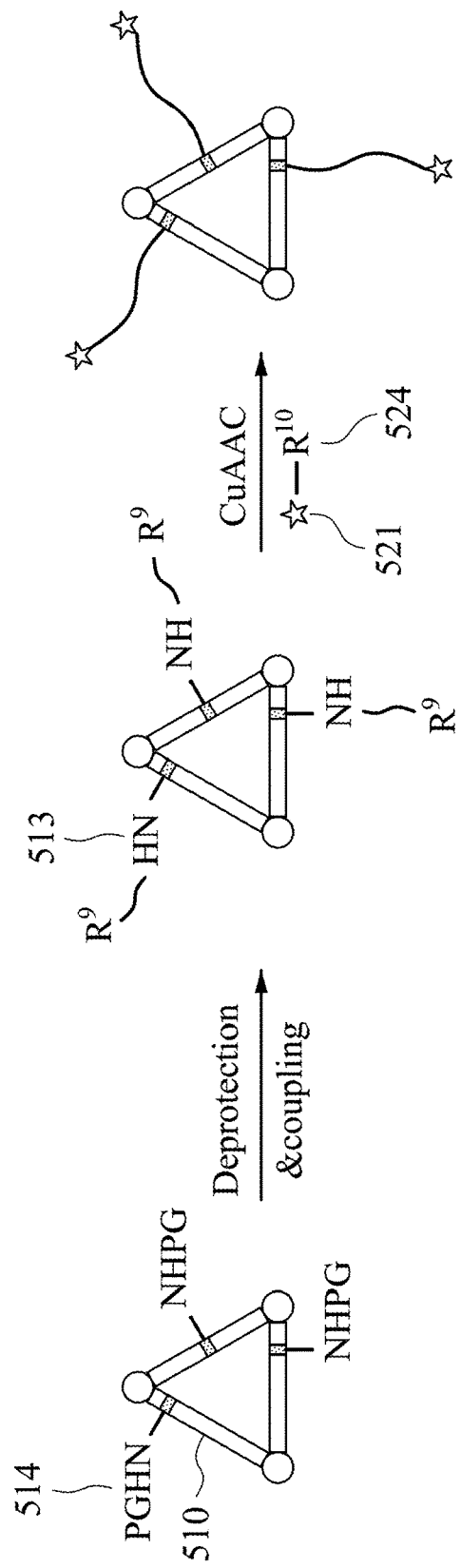
FIG. 13 is a schematic view showing the conjugation step according to yet another embodiment of the present disclosure.

FIG. 13 is a schematic view showing the conjugation steps according to yet another embodiment of the present disclosure. In FIG. 13, the conjugation step can be conducted by a deprotection and coupling reaction followed by a CuAAC in solution-phase. Specifically, the first chemical handle 514 includes a protected amino group PGHN, wherein PG is a protecting group, such as an.

Alloc group. The deprotection and coupling reaction is first conducted, so that the first chemical handle 514 can be transformed into the first chemical handle 513, which includes a medium group NH and a terminal group $R^9$. The second chemical handle 524 includes a terminal group $R^{10}$.

One of $R^9$ and $R^{10}$ is an alkyne group, and the other is an azide group, so that the ligand 521 can be connected with the PPII helix rod 510 through a CuAAC in solution-phase. According to another embodiment of a coupling reaction of the present disclosure, $R^9$ can be a ligand. In other words, the conjugation step can be conducted simply by a deprotection and coupling reaction.

Experimental Instruments

Analytical HPLC is performed using a 218TP54 (4.6 mm×250 mm) column from Vydac. Semi-preparative HPLC is carried out on a 218TP510 (10 mm×250 mm) column from Vydac. 0.1% TFA (trifluoroacetic acid) in water (solvent A) served as the eluent for compound purifications. Acetonitrile (solvent B) served as the mobile phase for compound purifications.

Aviv Model 410 spectropolarimeter (Aviv Associates, Lakewood, N.J.) is used for CD measurements. The solution is measured in a quartz cell with a pathlength of 1.0 mm (Hellma 110-QS).

Experimental Materials

The structures of Fmoc-Pro-OH (I), the first substituted Fmoc-Pro-OH (I-1), and the second substituted Fmoc-Pro-OH (1-2) are as follows.

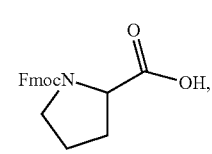
(I)

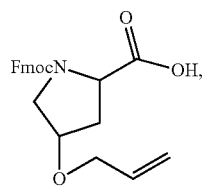
(I-1)

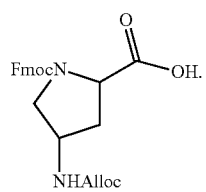
(I-2)

The structures of the ligand-providing compound (iv-1a), the ligand-providing compound (iv-1b), the ligand-providing compound (iv-1c) and the ligand-providing compound (iv-7a) are as follows.

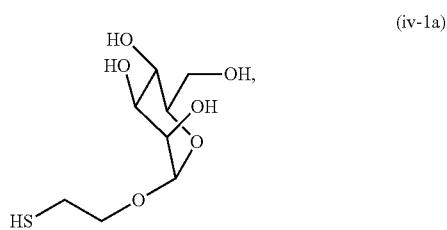
(iv-1a)

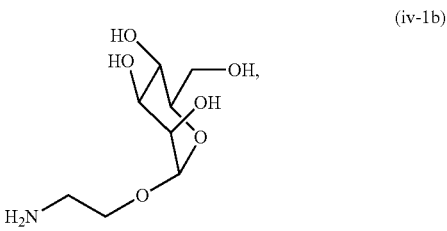
(iv-1b)

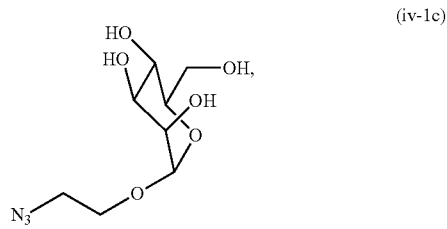
(iv-1c)

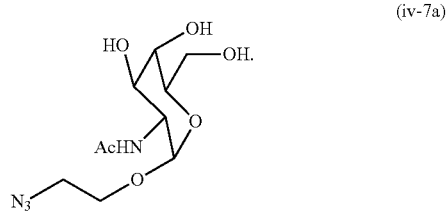
(iv-7a)

EXAMPLES/COMPARATIVE EXAMPLES

Example 1: The Synthesis of PPII Helix Rod C1

The PPII helix rod C1 has a structure as follows:

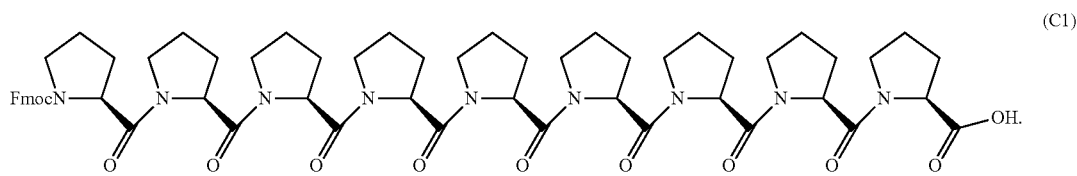
(C1)

The PPII helix rod C1 can be synthesized by a solid-phase peptide synthesis (SPPS) process, which includes Steps A, B, C, D and E. The amino acid sequence of the PPII helix rod C1 is referenced as SEQ ID NO: 1, wherein Xaa at residue 1 is the derivative 11 of proline.

In step A, preloading 2-chlorotrityl chloride resin is conducted. Specifically, 2-chlorotrityl chloride resin used as a solid support is first reactivated. After activation and washing with DCM (Dichloromethane; 5×3 mL), a solution of Fmoc-Pro-OH (I) (4.0 equiv.) and $^i$Pr$_2$NEt (N,N-diisopropylethylamine, 6.0 equiv.) in 1:1 v/v DMF (Dimethylformamide):DCM (final concentration 0.4 M) is added to the 2-chlorotrityl chloride resin. The mixture is gently shaken overnight and sequentially washed with DMF (3×3 mL), DCM (3×3 mL), and DMF (3×3 mL). A solution of DCM/MeOH/$^i$Pr$_2$NEt (17:2:1, 8 mL) is added and shaken for 1 h then sequentially washed with DMF (3×3 mL), DCM (3×3 mL), and DMF (3×3 mL). The loading is determined with a quantitative Fmoc test. The product of Step A is further used in iterative peptide synthesis.

In Step B, Fmoc-deprotection is conducted. Specifically, 10% piperidine in DMF (3 mL) is added to the product of Step A. The vessel is shaken for 10 min and sequentially washed with DMF (3×3 mL), DCM (3×3 mL), and DMF (3×3 mL). A product of Step B is obtained.

In Step C, amino acid coupling is conducted. Specifically, Fmoc-Pro-OH (I) (4 equiv.) and PyBOP (benzotriazol-1-yl-oxytripyrrolidinophosphonium hexafluorophosphate, 4 equiv.) dissolved in DMF followed by NMM (N-Methylmorpholine, 4 equiv.) are added to the product of Step B in DMF (final concentration 0.2 M). The mixture is gently shaken for 1 h then sequentially washed with DMF (3×3 mL), DCM (3×3 mL), and DMF (3×3 mL).

In Step D, capping is conducted. Specifically, the product of Step C is treated with Ac$_2$O/pyridine (1:9, 3 mL) and shaken for 10 min so as to obtain a capping product. The capping product is sequentially washed with DMF (3×3 mL), DCM (3×3 mL), and DMF (3×3 mL).

Step B to Step D are repeated for further seven times.

In Step E, cleavage of the peptides from the solid support is conducted. Specifically, the capping product obtained from the last Step D is first washed with DCM (3×3 mL), then is treated with TFA/H$_2$O/TIS (90:5:5, 3 mL) and shaken for 1 h and a second time for 30 min, wherein TIS is an abbreviation of triisopropylsilane. The filtrate is collected and removed all of the volatiles under reduced pressure. Water (1-2 mL) is added to the resulting syrup like compound and centrifuged. Transferred the supernatant and further purified by HPLC to obtain the final product of Example 1. The measuring results are as follows. Yield: 323 mg, 75%. Semi-preparative HPLC: 5-51% B in 30 min, 5 mL/min; R$_t$=22.3 min. Analytical HPLC: 5-90% B in 60 min, 0.5 mL/min; R$_t$=35.3 min. MS(MALDI) Calculated for C$_{60}$H$_{75}$N$_9$O$_{12}$: 1113.553, Found: 1136.860 [M+Na]$^+$. According to the measuring results, it can confirm that the final product of Example 1 is the PPII helix rod C1.

Example 2: The Synthesis of PPII Helix Rod C2

The PPII helix rod C2 has a structure as follows:

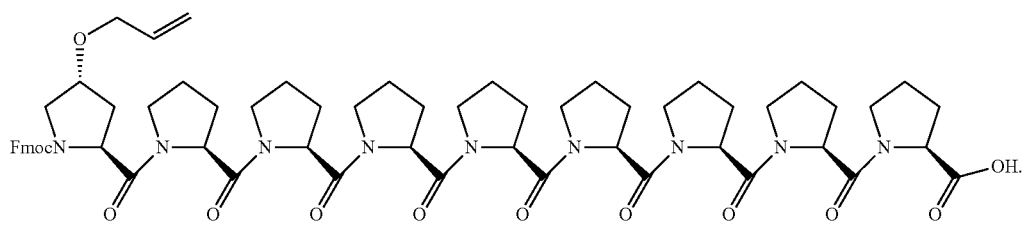

(C2)

The PPII helix rod C2 can be synthesized by the SPPS process, which is similar to that of Example 1. The difference is in the last time of Step C, the Fmoc-Pro-OH (I) is replaced by the first substituted Fmoc-Pro-OH (I-1). The measuring results of the final product of Example 2 are as follows. Yield: 81.2 mg, 63%. Semi-preparative HPLC: 5-51% B in 30 min, 5 mL/min; R$_t$=24.6 min. Analytical HPLC: 5-90% B in 60 min, 0.5 mL/min; R$_t$=35.1 min. MS(MALDI) Calculated for C$_{63}$H$_{79}$N$_9$O$_{13}$: 1169.580, Found: 1195.602 [M+Na]$^+$. According to the measuring results, it can confirm that the final product of Example 2 is the PPII helix rod C2. The amino acid sequence of the PPII helix rod C2 is referenced as SEQ ID NO: 2, wherein Xaa at residue 1 is the derivative 12 of proline.

Example 3: The Synthesis of PPII Helix Rod C3

The PPII helix rod C3 has a structure as follows.

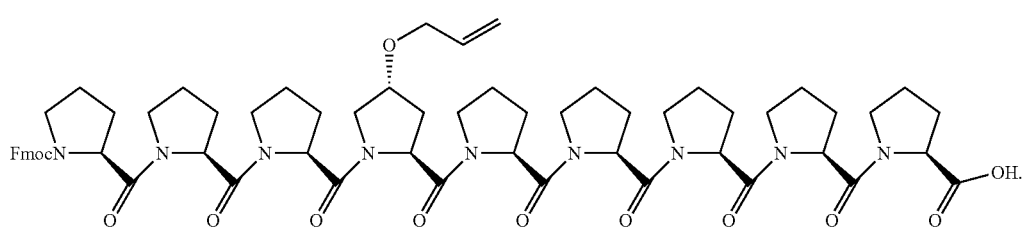

(C3)

The PPII helix rod C3 can be synthesized by the SPPS process, which is similar to that of Example 1. The difference is in the fifth time of Step C, the Fmoc-Pro-OH (I) is replaced by the first substituted Fmoc-Pro-OH (I-1). The measuring results of the final product of Example 3 are as follows. Yield: 92.8 mg, 40%. Semi-preparative HPLC: 5-51% B in 30 min, 5 mL/min; $R_t$=24.5 min. Analytical HPLC: 5-90% B in 60 min, 0.5 mL/min; $R_t$=33.3 min. MS(MALDI) Calculated for $C_{63}H_{79}N_9O_{13}$: 1169.580, Found: 1170.855 $[M+H]^+$. According to the measuring results, it can confirm that the final product of Example 3 is the PPII helix rod C3. The amino acid sequence of the PPII helix rod C3 is referenced as SEQ ID NO: 3, wherein Xaa at residue 1 is the derivative 11 of proline, and Xaa at residue 4 is derivative 1 of proline.

Example 4: The Synthesis of PPII Helix Rod C4

The PPII helix rod C4 has a structure as follows:

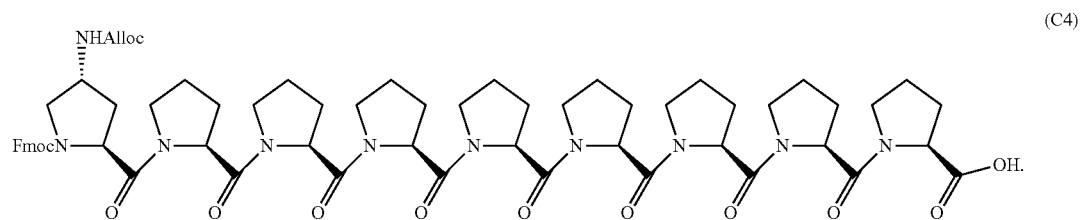

(C4)

The PPII helix rod C4 can be synthesized by the SPPS process, which is similar to that of Example 1. The difference is in the last time of Step C, the Fmoc-Pro-OH (I) is replaced by the second substituted Fmoc-Pro-OH (I-2). The measuring results of the final product of Example 4 are as follows. Yield: 104.3 mg, 98%. Semi-preparative HPLC: 5-51% B in 30 min, 5 mL/min; $R_t$=24.1 min. Analytical HPLC: 5-90% B in 60 min, 0.5 mL/min; $R_t$=36.3 min. MS(MALDI) Calculated for $C_{64}H_{80}N_{10}O_{14}$: 1212.586, Found: 1251.524 $[M+K]^+$. According to the measuring results, it can confirm that the final product of Example 4 is the PPII helix rod C4. The amino acid sequence of the PPII helix rod C4 is referenced as SEQ ID NO: 4, wherein Xaa at residue 1 is the derivative 13 of proline.

Example 5: The Synthesis of PPII Helix Rod C5

The PPII helix rod C5 has a structure as follows:

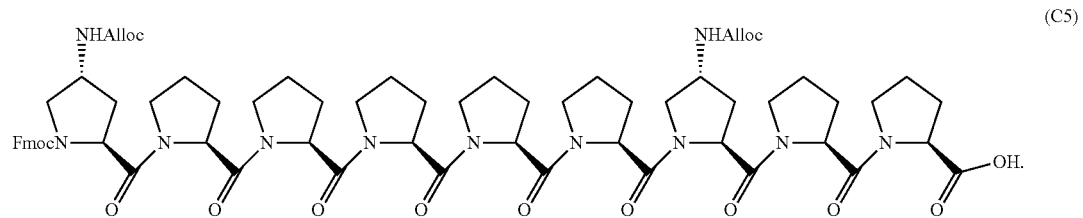

(C5)

The PPII helix rod C5 can be synthesized by the SPPS process, which is similar to that of Example 1. The difference is in the second time and the last time of Step C, the Fmoc-Pro-OH (I) is replaced by the second substituted Fmoc-Pro-OH (I-2). The measuring results of the final product of Example 5 are as follows. Yield: 113.1 mg, 63%. Semi-preparative HPLC: 5-51% B in 30 min, 5 mL/min; $R_t$=26.0 min. Analytical HPLC: 5-90% B in 60 min, 0.5 mL/min; $R_t$=37.6 min. MS(MALDI) Calculated for $C_{68}H_{85}N_{11}O_{16}$: 1311.618, Found: 1334.486 $[M+Na]^+$. According to the measuring results, it can confirm that the final product of Example 5 is the PPII helix rod C5. The amino acid sequence of the PPII helix rod C5 is referenced as SEQ ID NO: 5, wherein Xaa at residue 1 is the derivative 13 of proline, and Xaa at residue 7 is derivative 2 of proline.

Example 6: The Synthesis of PPII Helix Rod C6

The PPII helix rod C6 has a structure as follows:

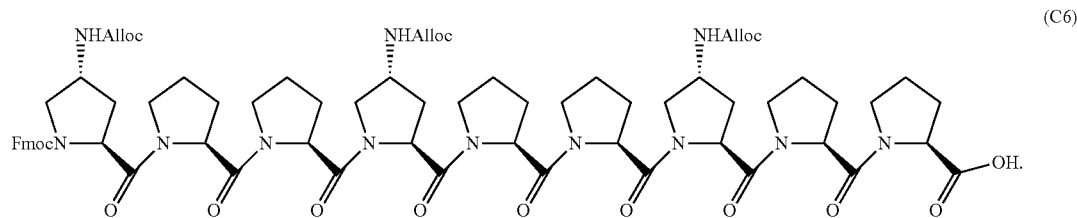

(C6)

The PPII helix rod C6 can be synthesized by the SPPS process, which is similar to that of Example 1. The difference is in the second time, the fifth time and the last time of Step C, the Fmoc-Pro-OH (I) is replaced by the second substituted Fmoc-Pro-OH (I-2). The measuring results of the final product of Example 6 are as follows. Yield: 51.5 mg, 44%. Semi-preparative HPLC: 5-51% B in 30 min, 5 mL/min; $R_t$=27.7 min. Analytical HPLC: 5-90% B in 60 min, 0.5 mL/min; $R_t$=39.8 min. MS(MALDI) Calculated for $C_{72}H_{90}N_{12}O_{18}$: 1410.650, Found: 1433.427 $[M+Na]^+$.

According to the measuring results, it can confirm that the final product of Example 6 is the PPII helix rod C6. The amino acid sequence of the PPII helix rod C6 is referenced as SEQ ID NO: 6, wherein Xaa at residue 1 is the derivative 13 of proline, and Xaa at residues 4 and 7 is the derivative 2 of proline, respectively.

Example 7: The Synthesis of PPII Helix Rod C11

The PPII helix rod C11 has a structure as follows:

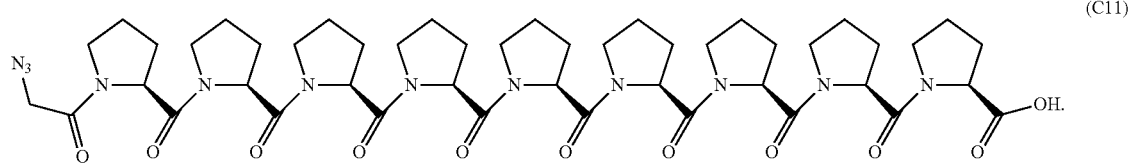 [SMILES: [N-]=[N+]=NCC(=O)N1CCC[C@H]1C(=O)N1CCC[C@H]1C(=O)N1CCC[C@H]1C(=O)N1CCC[C@H]1C(=O)N1CCC[C@H]1C(=O)N1CCC[C@H]1C(=O)N1CCC[C@H]1C(=O)N1CCC[C@H]1C(=O)N1CCC[C@H]1C(=O)O]

(C11)

The PPII helix rod C11 can be synthesized by the SPPS process, which is similar to that of Example 1. The difference is Step B to Step D are repeated for further eight times, and the Fmoc-Pro-OH (I) of last time of Step C in Example 1 is replaced by 2-azidoacetic acid ($N_3CH_2COOH$).

The measuring results of the final product of Example 7 are as follows. Yield: 50.7 mg, 68%. Semi-preparative HPLC: 5-23% B in 23 min, 5 mL/min; $R_t$=17.1 min. Analytical HPLC: 5-90% B in 90 min, 0.5 mL/min; $R_t$=20.5 min. MS(MALDI) Calculated for $C_{47}H_{66}N_{12}O_{11}$: 974.497, Found: 997.022 $[M+Na]^+$. According to the measuring results, it can confirm that the final product of Example 7 is the PPII helix rod C11. The amino acid sequence of the PPII helix rod C11 is referenced as SEQ ID NO: 7, wherein Xaa at residue 1 is the derivative 14 of proline.

Example 8: The Synthesis of PPII Helix Rod C12

The PPII helix rod C12 has a structure as follows:

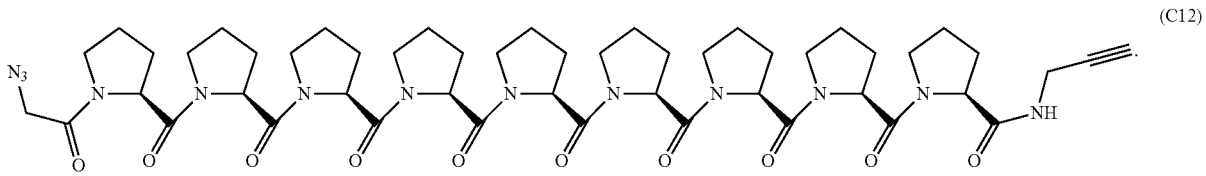 [SMILES: C#CCNC(=O)[C@@H]1CCCN1C(=O)[C@@H]1CCCN1C(=O)[C@@H]1CCCN1C(=O)[C@@H]1CCCN1C(=O)[C@@H]1CCCN1C(=O)[C@@H]1CCCN1C(=O)[C@@H]1CCCN1C(=O)[C@@H]1CCCN1C(=O)[C@@H]1CCCN1C(=O)CN=[N+]=[N-]]

(C12)

The PPII helix rod C12 can be synthesized by Step F. In Step F, an alkynylation reaction is conducted, in which the PPII helix rod C11 is coupled with propargylamine. Specifically, the PPII helix rod C11, propargylamine (3 equiv.), and TEA (5 equiv.) is dissolved in DMF:DCM (1:1, PPII helix rod C1 concentration 10 mM) followed by HATU (4 equiv.) are added to the vial, wherein HATU is an abbreviation of 1-[bis(dimethylamino)methylene]-1H-1,2,3-triazolo[4,5-b]pyridinium 3-oxide hexafluorophosphate. The mixture is stirred overnight, after removal of DCM under reduced pressure and centrifuge, the crude product is purified by HPLC.

The measuring results of the final product of Example 8 are as follows. Yield: 14.9 mg, 61%. Semi-preparative HPLC: 5-23% B in 23 min, 5 mL/min; $R_t$=18.9 min. Analytical HPLC: 5-90% B in 60 min, 0.5 mL/min; $R_t$=21.7 min. MS(MALDI) Calculated for $C_{50}H_{69}N_{13}O_{10}$: 1011.529, Found: 1027.857 $[M+Na]^+$. According to the measuring results, it can confirm that the final product of Example 8 is the PPII helix rod C12. The amino acid sequence of the PPII helix rod C12 is referenced as SEQ ID NO: 8, wherein Xaa at residue 1 is the derivative 14 of proline, and Xaa at residue 9 is the derivative 15 of proline.

Example 9: The Synthesis of PPII Helix Rod C13

The PPII helix rod C13 has a structure as follows:

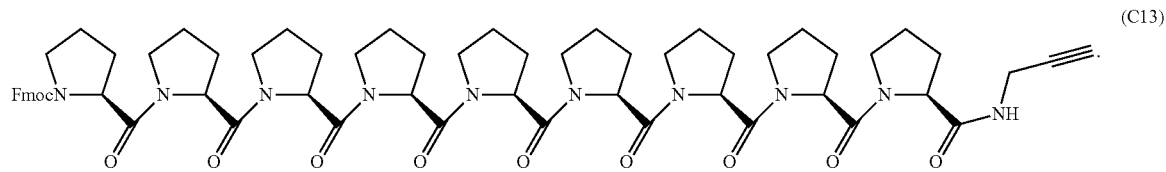
(C13)

The PPII helix rod C13 can be synthesized by an alkynylation reaction, which is similar to Step F in Example 8 but replacing the PPII helix rod C11 with the PPII helix rod C1.

The measuring results of the final product of Example 9 are as follows. Yield: 323.2 mg, 75%. Semi-preparative HPLC: 5-51% B in 30 min, 5 mL/min; $R_f$=23.2 min. Analytical HPLC: 5-90% B in 60 min, 0.5 mL/min; $R_f$=37.5 min. MS(MALDI) Calculated for $C_{63}H_{78}N_{10}O_{11}$: 1150.585, Found: 1174.375 [M+Na]$^+$. According to the measuring results, it can confirm that the final product of Example 9 is the PPII helix rod C13. The amino acid sequence of the PPII helix rod C13 is referenced as SEQ ID NO: 9, wherein Xaa at residue 1 is the derivative 11 of proline, and Xaa at residue 9 is the derivative 15 of proline.

Example 10: The Synthesis of PPII Helix Rod C21

The PPII helix rod C21 has a structure as follows:

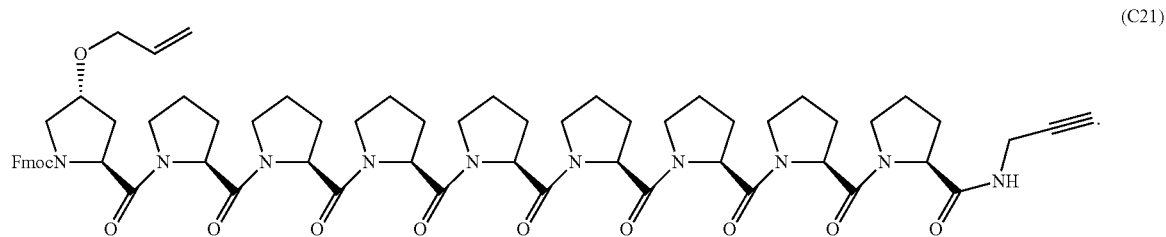
(C21)

The PPII helix rod C21 can be synthesized by an alkynylation reaction, which is similar to Step F in Example 8 but replacing the PPII helix rod C11 with the PPII helix rod C2.

The measuring results of the final product of Example 10 are as follows. Yield: 86.8 mg, 84%. Semi-preparative HPLC: 5-51% B in 30 min, 5 mL/min; $R_f$=25.5 min. Analytical HPLC: 5-90% B in 60 min, 0.5 mL/min; $R_f$=37.7 min. MS(MALDI) Calculated for $C_{66}H_{82}N_{10}O_{12}$: 1206.611, Found: 1208.902 [M+H]$^+$. According to the measuring results, it can confirm that the final product of Example 10 is the PPII helix rod C21. The amino acid sequence of the PPII helix rod C21 is referenced as SEQ ID NO: 10, wherein Xaa at residue 1 is the derivative 12 of proline, and Xaa at residue 9 is the derivative 15 of proline.

Example 11: The Synthesis of PPII Helix Rod C31

The PPII helix rod C31 has a structure as follows:

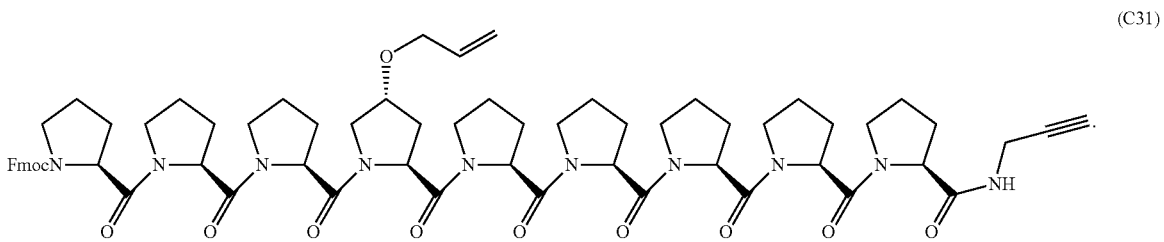
(C31)

The PPII helix rod C31 can be synthesized by an alkynylation reaction, which is similar to Step F in Example 8 but replacing the PPII helix rod C11 with the PPII helix rod C3.

The measuring results of the final product of Example 11 are as follows. Yield: 40.1 mg, 77%. Semi-preparative HPLC: 5-51% B in 30 min, 5 mL/min; $R_t$=25.1 min. Analytical HPLC: 5-90% B in 60 min, 0.5 mL/min; $R_t$=38.9 min. MS(MALDI) Calculated for $C_{66}H_{82}N_{10}O_{12}$: 1206.611, Found: 1230.052 $[M+Na]^+$. According to the measuring results, it can confirm that the final product of Example 11 is the PPII helix rod C31. The amino acid sequence of the PPII helix rod C31 is referenced as SEQ ID NO: 11, wherein Xaa at residue 1 is the derivative 11 of proline, Xaa at residue 4 is the derivative 1 of proline, and Xaa at residue 9 is the derivative 15 of proline.

Example 12: The Synthesis of PPII Helix Rod C41

The PPII helix rod C41 has a structure as follows:

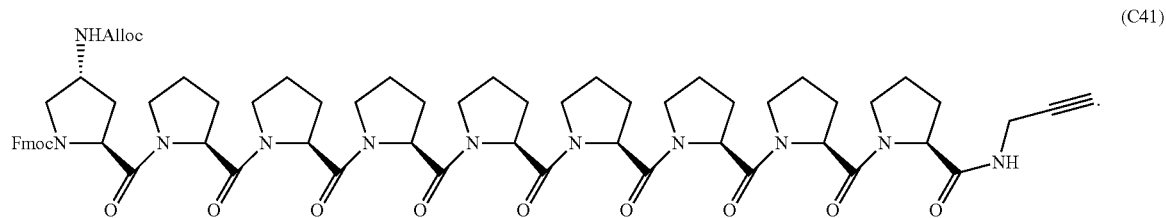
(C41)

The PPII helix rod C41 can be synthesized by an alkynylation reaction, which is similar to Step F in Example 8 but replacing the PPII helix rod C11 with the PPII helix rod C4.

The measuring results of the final product of Example 12 are as follows. Yield: 55.8 mg, 68%. Semi-preparative HPLC: 5-51% B in 30 min, 5 mL/min; $R_t$=25.0 min. Analytical HPLC: 5-90% B in 60 min, 0.5 mL/min; $R_t$=34.1 min. MS(MALDI) Calculated for $C_{67}H_{83}N_{11}O_{13}$: 1249.617, Found: 1250.071 $[M+H]^+$. According to the measuring results, it can confirm that the final product of Example 12 is the PPII helix rod C41. The amino acid sequence of the PPII helix rod C41 is referenced as SEQ ID NO: 12, wherein Xaa at residue 1 is the derivative 13 of proline, and Xaa at residue 9 is the derivative 15 of proline.

Example 13: The Synthesis of PPII Helix Rod C51

The PPII helix rod C51 has a structure as follows:

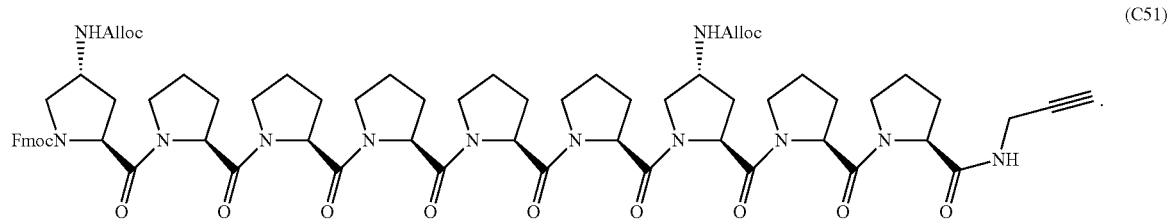
(C51)

The PPII helix rod C51 can be synthesized by an alkynylation reaction, which is similar to Step F in Example 8 but replacing the PPII helix rod C11 with the PPII helix rod C5.

The measuring results of the final product of Example 13 are as follows. Yield: 58.4 mg, 50%. Semi-preparative HPLC: 5-51% B in 30 min, 5 mL/min; $R_t$=26.1 min. Analytical HPLC: 5-90% B in 60 min, 0.5 mL/min; $R_t$=39.5 min. MS(MALDI) Calculated for $C_{71}H_{88}N_{12}O_{15}$: 1348.649, Found: 1349.748 $[M+H]^+$. According to the measuring results, it can confirm that the final product of Example 13 is the PPII helix rod C51. The amino acid sequence of the PPII helix rod C51 is referenced as SEQ ID NO: 13, wherein Xaa at residue 1 is the derivative 13 of proline, Xaa at residue 7 is the derivative 2 of proline, and Xaa at residue 9 is the derivative 15 of proline.

Example 14: The Synthesis of PPII Helix Rod C61

The PPII helix rod C61 has a structure as follows:

The linear chain L1 can be synthesized by a CuAAC in solid-phase, which includes Step G, a Fmoc-deprotection step and a coupling step.

In Step G, the azide-functionalized resin corresponding to Example 2 (used as a solid support) is treated with PPII helix rod C21 (1.5 equiv.), $CuSO_4 \cdot 5H_2O$ (0.13 equiv., from 40 mM solution water), ligand triethyl 2,2',2"-(4,4',4"-nitrilotris (methylene)tris(1H-1,2,3-triazole-4,1-diyl))triacetate (0.13 equiv., from 40 mM solution in DMSO (Dimethyl sulfoxide)), sodium ascorbate (2.6 equiv., from 800 mM solution in water), and $^iPr_2NEt$ (4.0 equiv.) in DMF:THF (tetrahydrofuran)(1:1, final copper concentration 3.6 mM) at 30° C. for 6 h. The final product is sequentially washed with DMF (5×1 mL), DCM (5×1 mL), and DMF (5×1 mL).

The Fmoc-deprotection step is similar to Step B in Example 1 but replacing the product of Step A with the product of Step G.

The coupling step is similar to Step C in Example 1 but replacing Fmoc-Pro-OH (I) with 2-azidoacetic acid.

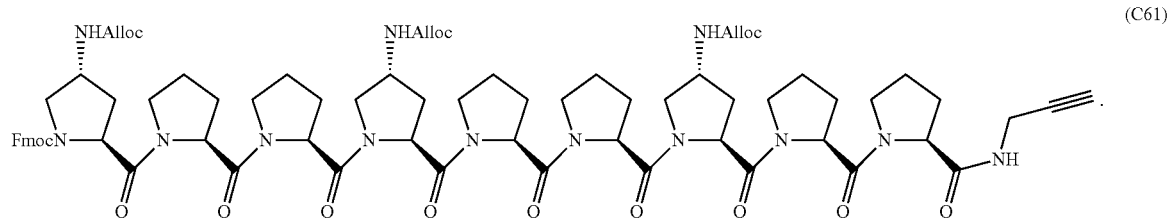

(C61)

The PPII helix rod C61 can be synthesized by an alkynylation reaction, which is similar to Step F in Example 8 but replacing the PPII helix rod C11 with the PPII helix rod C6.

The measuring results of the final product of Example 14 are as follows. Yield: 17.81 mg, 34%. Semi-preparative HPLC: 5-90% B in 30 min, 5 mL/min; $R_t$=18.0 min. Analytical HPLC: 5-90% B in 60 min, 0.5 mL/min; $R_t$=41.8 min. MS(MALDI) Calculated for $C_{75}H_{93}N_{13}O_{17}$: 1447.681, Found: 1470.361 $[M+Na]^+$. According to the measuring results, it can confirm that the final product of Example 14 is the PPII helix rod C61. The amino acid sequence of the PPII helix rod C61 is referenced as SEQ ID NO: 14, wherein Xaa at residue 1 is the derivative 13 of proline, Xaa at residues 4 and 7 is the derivative 2 of proline, respectively, and Xaa at residue 9 is the derivative 15 of proline.

Example 15: The Synthesis of Linear Chain L1

The linear chain L1 has a structure as follows:

Then Step G, the Fmoc-deprotection step and the coupling step are repeated once more.

Finally, a cleavage step is conducted, which is similar to Step E in Example 1 but replacing the capping resin obtained from the last Step D with the product of the last coupling step in Example 15.

The measuring results of the final product of Example 15 are as follows. Yield: 2.00 mg, 26%. Semi-preparative HPLC: 5-90% B in 30 min, 5 mL/min; $R_t$=13.6 min. Analytical HPLC: 5-90% B in 60 min, 0.5 mL/min; $R_t$=30.7 min. MS(MALDI) Calculated for $C_{156}H_{216}N_{38}O_{34}$: 3165.634, Found: 3166.348 $[M+H]^+$. According to the measuring results, it can confirm that the final product of Example 15 is the linear chain L1. The amino acid sequence of the linear chain L1 is referenced as SEQ ID NO: 15, wherein Xaa at residue 1 is the derivative 16 of proline, and Xaa at residues 10 and 19 is the derivative 1 of proline, respectively.

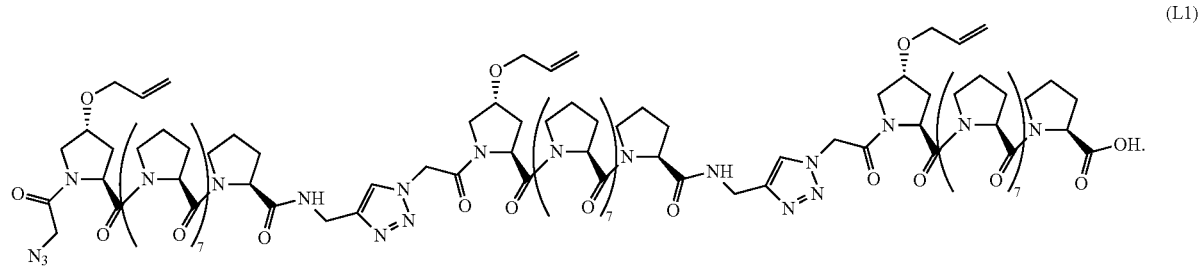

(L1)

Example 16: The Synthesis of Linear Chain L2

The linear chain L2 has a structure as follows:

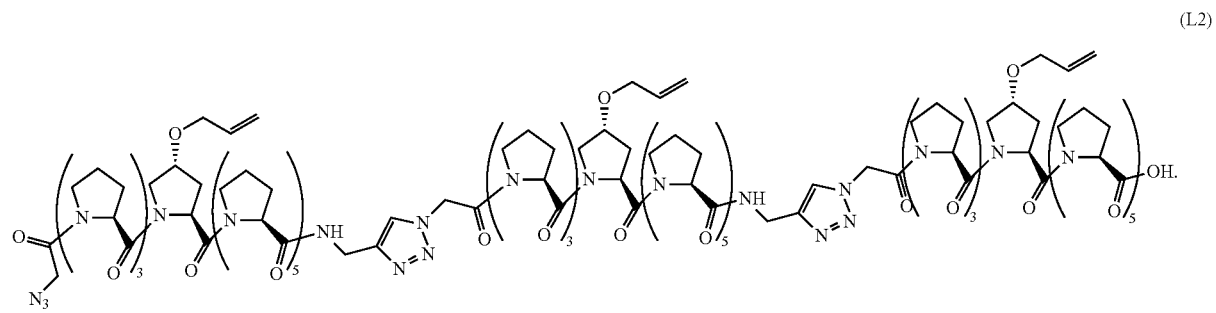
(L2)

The linear chain L2 can be synthesized by a CuAAC in solid-phase, which is similar to that in Example 15 but replacing the azide-functionalized resin corresponding to Example 2 with the azide-functionalized resin corresponding to Example 3 and the PPII helix rod C21 with the PPII helix rod C31 in Step G.

The measuring results of the final product of Example 16 are as follows. Yield: 1.02 mg, 10%. Semi-preparative HPLC: 5-90% B in 30 min, 5 mL/min; $R_t$=12.7 min. Analytical HPLC: 5-90% B in 60 min, 0.5 mL/min; $R_t$=30.0 min. MS(MALDI) Calculated for $C_{156}H_{216}N_{38}O_{34}$: 3165.634, Found: 3166.689 $[M+H]^+$. According to the measuring results, it can confirm that the final product of Example 16 is the linear chain L2. The amino acid sequence of the linear chain L2 is referenced as SEQ ID NO: 16, wherein Xaa at residue 1 is the derivative 14 of proline, and Xaa at residues 4, 13 and 22 is the derivative 1 of proline, respectively.

Example 17: The Synthesis of Linear Chain L3

The linear chain L3 has a structure as follows:

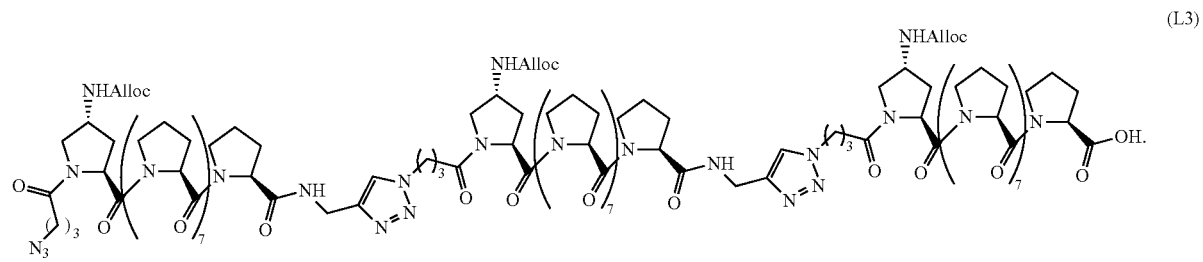
(L3)

The linear chain L3 can be synthesized by a CuAAC in solid-phase, which is similar to that in Example 15 but replacing the azide-functionalized resin corresponding to Example 2 with the azide-functionalized resin corresponding to Example 4, the 2-azidoacetic acid with 4-azidobutanoic acid in the coupling step and the PPII helix rod C21 with the PPII helix rod C41 in Step G.

The measuring results of the final product of Example 17 are as follows. Yield: 4.70 mg, 24%. Semi-preparative HPLC: 5-51% B in 30 min, 5 mL/min; $R_t$=20.2 min. Analytical HPLC: 5-90% B in 60 min, 0.5 mL/min; $R_t$=32.4 min. MS(MALDI) Calculated for $C_{165}H_{231}N_{41}O_{37}$: 3378.745, Found: 3380.558 $[M+H]^+$. According to the measuring results, it can confirm that the final product of Example 17 is the linear chain L3. The amino acid sequence of the linear chain L3 is referenced as SEQ ID NO: 17, wherein Xaa at residue 1 is the derivative 17 of proline, and Xaa at residues 10 and 19 is the derivative 2 of proline, respectively.

Example 18: The Synthesis of Linear Chain L4

The linear chain L4 has a structure as follows:

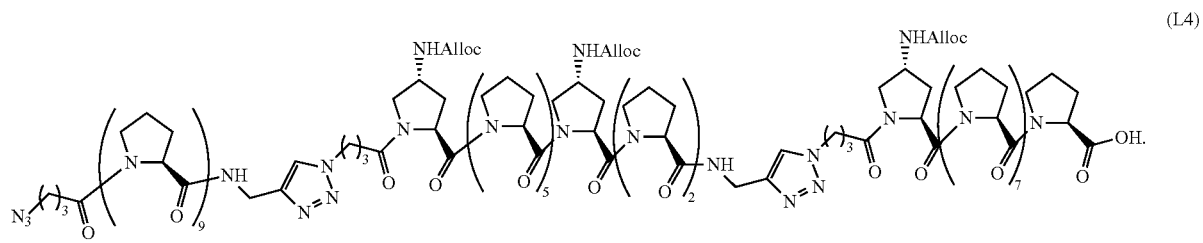
(L4)

The linear chain L4 can be synthesized by a CuAAC in solid-phase, which is similar to that in Example 17 but replacing the PPII helix rod C41 with the PPII helix rod C51 in the first Step G and the PPII helix rod C41 with the PPII helix rod C13 in the second Step G.

The measuring results of the final product of Example 18 are as follows. Yield: 3.41 mg, 42%. Semi-preparative HPLC: 5-90% B in 30 min, 5 mL/min; $R_f$=13.6 min. Analytical HPLC: 5-90% B in 60 min, 0.5 mL/min; $R_t$=31.8 min. MS(MALDI) Calculated for $C_{165}H_{231}N_{41}O_{37}$: 3378.745, Found: 3401.112 [M+Na]$^+$. According to the measuring results, it can confirm that the final product of Example 18 is the linear chain L4. The amino acid sequence of the linear chain L4 is referenced as SEQ ID NO: 18, wherein Xaa at residue 1 is the derivative 18 of proline, and Xaa at residues 10, 16 and 19 is the derivative 2 of proline, respectively.

Example 19: The Synthesis of Linear Chain L5

The linear chain L5 has a structure as follows:

Example 2 with the azide-functionalized resin corresponding to Example 1, the 2-azidoacetic acid with 4-azidobutanoic acid in the coupling step, the PPII helix rod C21 with the PPII helix rod C61 in the first Step G and the PPII helix rod C21 with the PPII helix rod C13 in the second step G.

The measuring results of the final product of Example 19 are as follows. Yield: 5.01 mg, 69%. Semi-preparative HPLC: 5-90% B in 30 min, 5 mL/min; $R_f$=13.0 min. Analytical HPLC: 5-90% B in 60 min, 0.5 mL/min; $R_t$=33.2 min. MS(MALDI) Calculated for $C_{165}H_{231}N_{41}O_{37}$: 3378.745, Found: 3399.406 [M+Na]$^+$. According to the measuring results, it can confirm that the final product of Example 19 is the linear chain L5. The amino acid sequence of the linear chain L5 is referenced as SEQ ID NO: 19, wherein Xaa at residue 1 is the derivative 18 of proline, and Xaa at residues 10, 13 and 16 is the derivative 2 of proline, respectively.

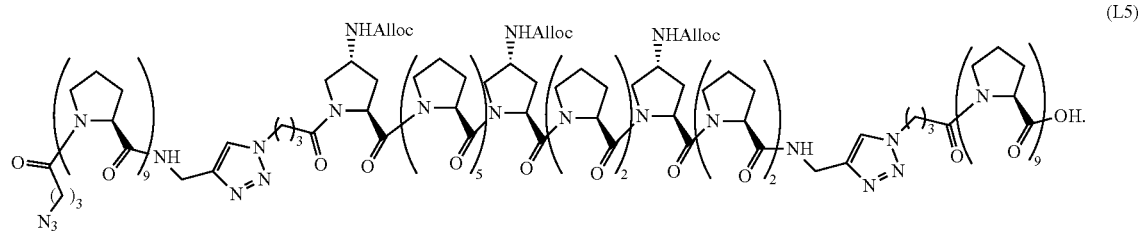
(L5)

The linear chain L5 can be synthesized by a CuAAC in solid-phase, which is similar to that in Example 15 but replacing the azide-functionalized resin corresponding to Example 20: The Synthesis of Linear Chain L11

The linear chain L11 has a structure as follows:

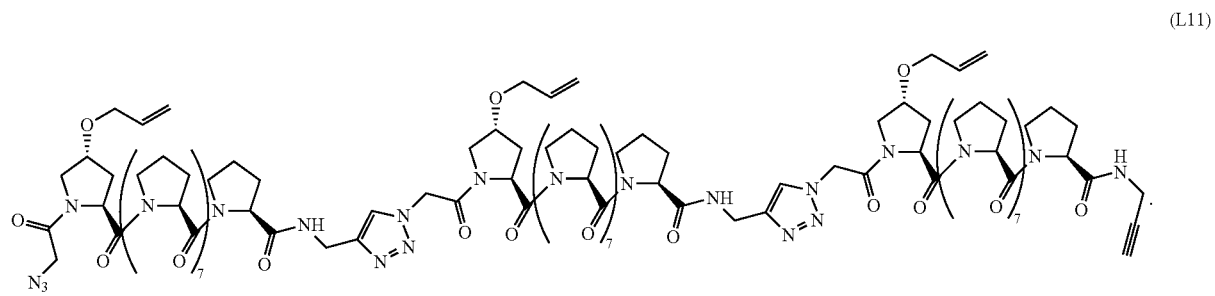
(L11)

The linear chain L11 can be synthesized by an alkynylation reaction, which is similar to Step F in Example 8 but replacing the PPII helix rod C11 with the linear chain L1.

The measuring results of the final product of Example 20 are as follows. Yield: 2.1 mg, 92%. Semi-preparative HPLC: 5-90% B in 30 min, 5 mL/min; $R_f$=13.9 min. Analytical HPLC: 5-90% B in 60 min, 0.5 mL/min; $R_f$=32.1 min. MS(MALDI) Calculated for $C_{159}H_{219}N_{39}O_{33}$: 3202.666, Found: 3225.378 $[M+Na]^+$. According to the measuring results, it can confirm that the final product of Example 20 is the linear chain L11. The amino acid sequence of the linear chain L11 is referenced as SEQ ID NO: 20, wherein Xaa at residue 1 is the derivative 16 of proline, Xaa at residues 10 and 19 is the derivative 1 of proline, respectively, and Xaa at residue 27 is the derivative 15 of proline.

Example 21: The Synthesis of Linear Chain L21

The linear chain L21 has a structure as follows:

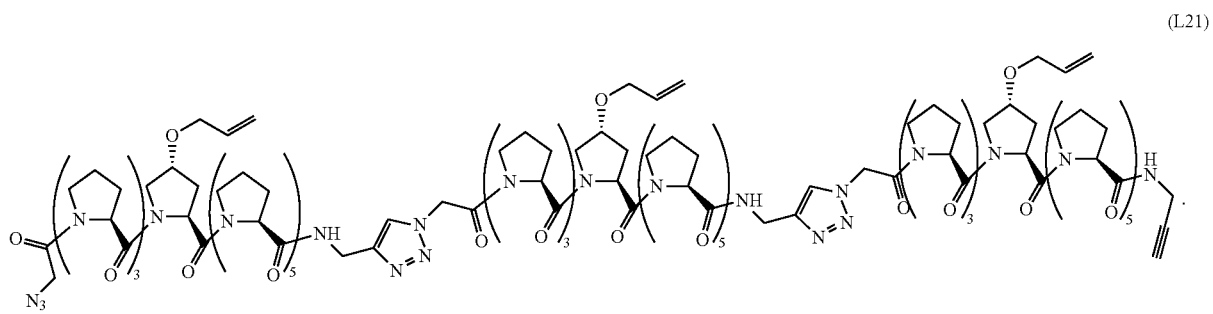

(L21)

The linear chain L21 can be synthesized by an alkynylation reaction, which is similar to Step F in Example 8 but replacing the PPII helix rod C11 with the linear chain L2.

The measuring results of the final product of Example 21 are as follows. Yield: 0.83 mg, 80%. Semi-preparative HPLC: 5-90% B in 30 min, 5 mL/min; $R_f$=13.9 min. Analytical HPLC: 5-90% B in 60 min, 0.5 mL/min; $R_f$=31.8 min. MS(MALDI) Calculated for $C_{159}H_{219}N_{39}O_{33}$: 3202.666, Found: 3203.625 $[M+H]^+$. According to the measuring results, it can confirm that the final product of Example 21 is the linear chain L21. The amino acid sequence of the linear chain L21 is referenced as SEQ ID NO: 21, wherein Xaa at residue 1 is the derivative 14 of proline, and Xaa at residues 4, 13 and 22 is the derivative 1 of proline, respectively.

Example 22: The Synthesis of Linear Chain L31

The linear chain L31 has a structure as follows:

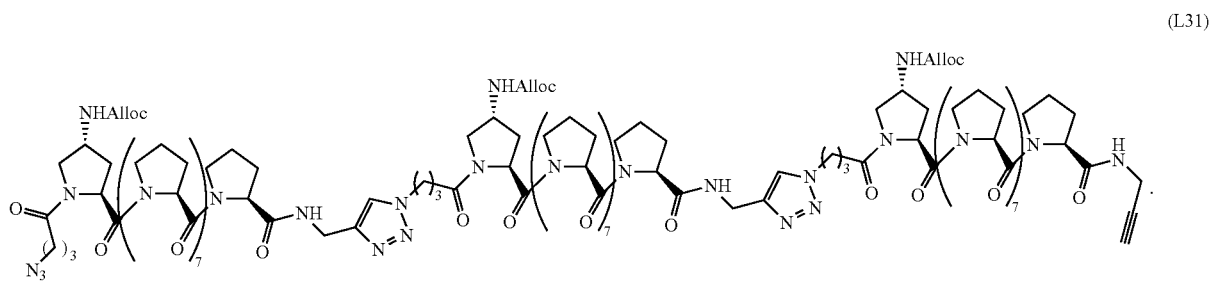

(L31)

The linear chain L31 can be synthesized by an alkynylation reaction, which is similar to Step F in Example 8 but replacing the PPII helix rod C11 with the linear chain L3.

The measuring results of the final product of Example 22 are as follows. Yield: 3.48 mg, 97%. Semi-preparative HPLC: 5-51% B in 30 min, 5 mL/min; $R_f$=22.9 min. Analytical HPLC: 5-90% B in 60 min, 0.5 mL/min; $R_t$=34.1 min. MS(MALDI) Calculated for $C_{168}H_{234}N_{42}O_{36}$: 3415.777, Found: 3416.579 $[M+H]^+$. According to the measuring results, it can confirm that the final product of Example 22 is the linear chain L31. The amino acid sequence of the linear chain L31 is referenced as SEQ ID NO: 22, wherein Xaa at residue 1 is the derivative 17 of proline, Xaa at residues 10 and 19 is the derivative 2 of proline, respectively, and Xaa at residue 27 is the derivative 15 of proline.

Example 23: The Synthesis of Linear Chain L41

The linear chain L41 has a structure as follows:

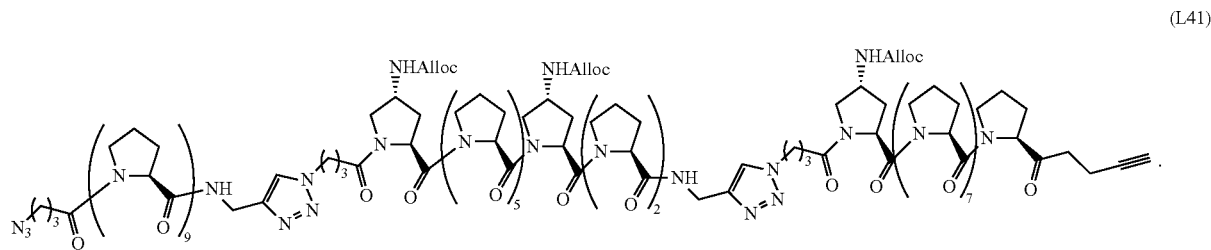

(L41)

The linear chain L41 can be synthesized by an alkynylation reaction, which is similar to Step F in Example 8 but replacing the PPII helix rod C11 with the linear chain L4.

The measuring results of the final product of Example 23 are as follows. Yield: 3.21 mg, 93%. Semi-preparative HPLC: 5-90% B in 60 min, 5 mL/min; $R_f$=14.6 min. Analytical HPLC: 5-90% B in 60 min, 0.5 mL/min; $R_t$=33.2 min. MS(MALDI) Calculated for $C_{168}H_{234}N_{42}O_{36}$: 3415.777, Found: 3439.562 $[M+Na]^+$. According to the measuring results, it can confirm that the final product of Example 23 is the linear chain L41. The amino acid sequence of the linear chain L41 is referenced as SEQ ID NO: 23, wherein Xaa at residue 1 is the derivative 18 of proline, Xaa at residues 10, 16 and 19 is the derivative 2 of proline, respectively, and Xaa at residue 27 is the derivative 15 of proline.

Example 24: The Synthesis of Linear Chain L51

The linear chain L51 has a structure as follows:

The linear chain L51 can be synthesized by an alkynylation reaction, which is similar to Step F in Example 8 but replacing the PPII helix rod C11 with the linear chain L5.

The measuring results of the final product of Example 24 are as follows. Yield: 6.22 mg, 79%. Semi-preparative HPLC: 5-90% B in 30 min, 5 mL/min; $R_f$=14.5 min. Analytical HPLC: 5-90% B in 60 min, 0.5 mL/min; $R_t$=33.0 min. MS(MALDI) Calculated for $C_{168}H_{234}N_{42}O_{36}$: 3415.777, Found: 3436.565 $[M+Na]^+$. According to the measuring results, it can confirm that the final product of Example 24 is the linear chain L51. The amino acid sequence of the linear chain L51 is referenced as SEQ ID NO: 24, wherein Xaa at residue 1 is the derivative 18 of proline, Xaa at residues 10, 13 and 16 is the derivative 2 of proline, respectively, and Xaa at residue 27 is the derivative 15 of proline.

(L51)

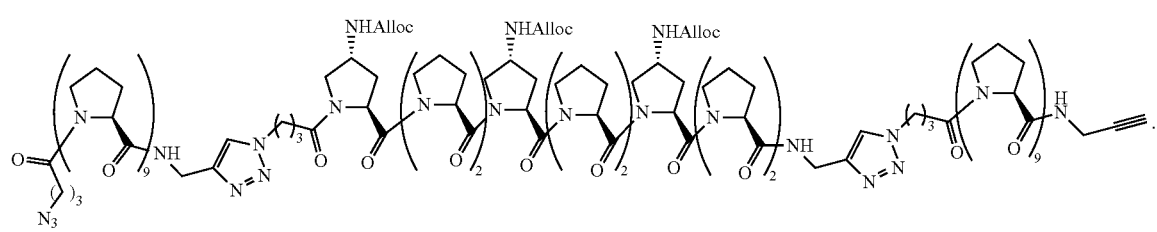

Example 25: The Synthesis of Polygonal Scaffold S1

The polygonal scaffold S1 has a structure as follows:

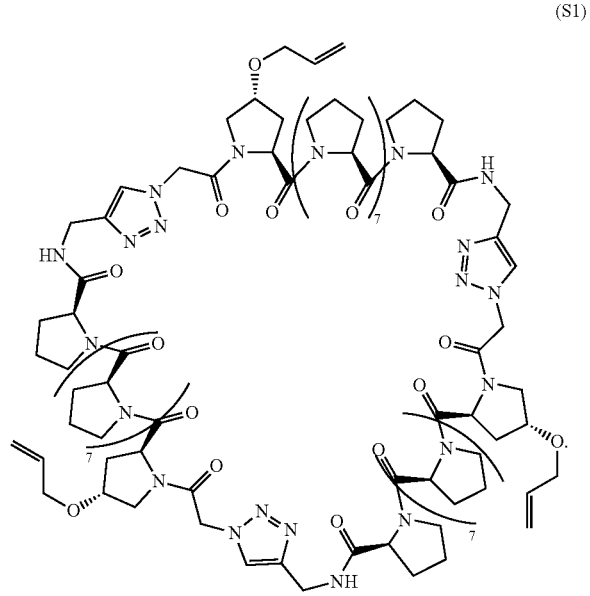

(S1)

The polygonal scaffold S1 can be synthesized by Step H, which is conducted by a CuAAC in solution-phase.

In Step H, the linear chain L11 is prepared as 2 mM aqueous solution, and treated with $CuSO_4 \cdot 5H_2O$ (4.2 equiv., from 40 mM solution water), ligand triethyl 2,2',2"-(4,4',4"-nitrilotris(methylene)tris(1H-1,2,3-triazole-4,1-diyl))triacetate (4.2 equiv., from 40 mM solution in DMSO), sodium ascorbate (84 equiv., from 800 mM solution in water) and $^{i}Pr_2NEt$ (144 equiv.) (final copper concentration 5 mM) at 40° C. for 1 h, the crude product is purified by HPLC.

Figure 14:
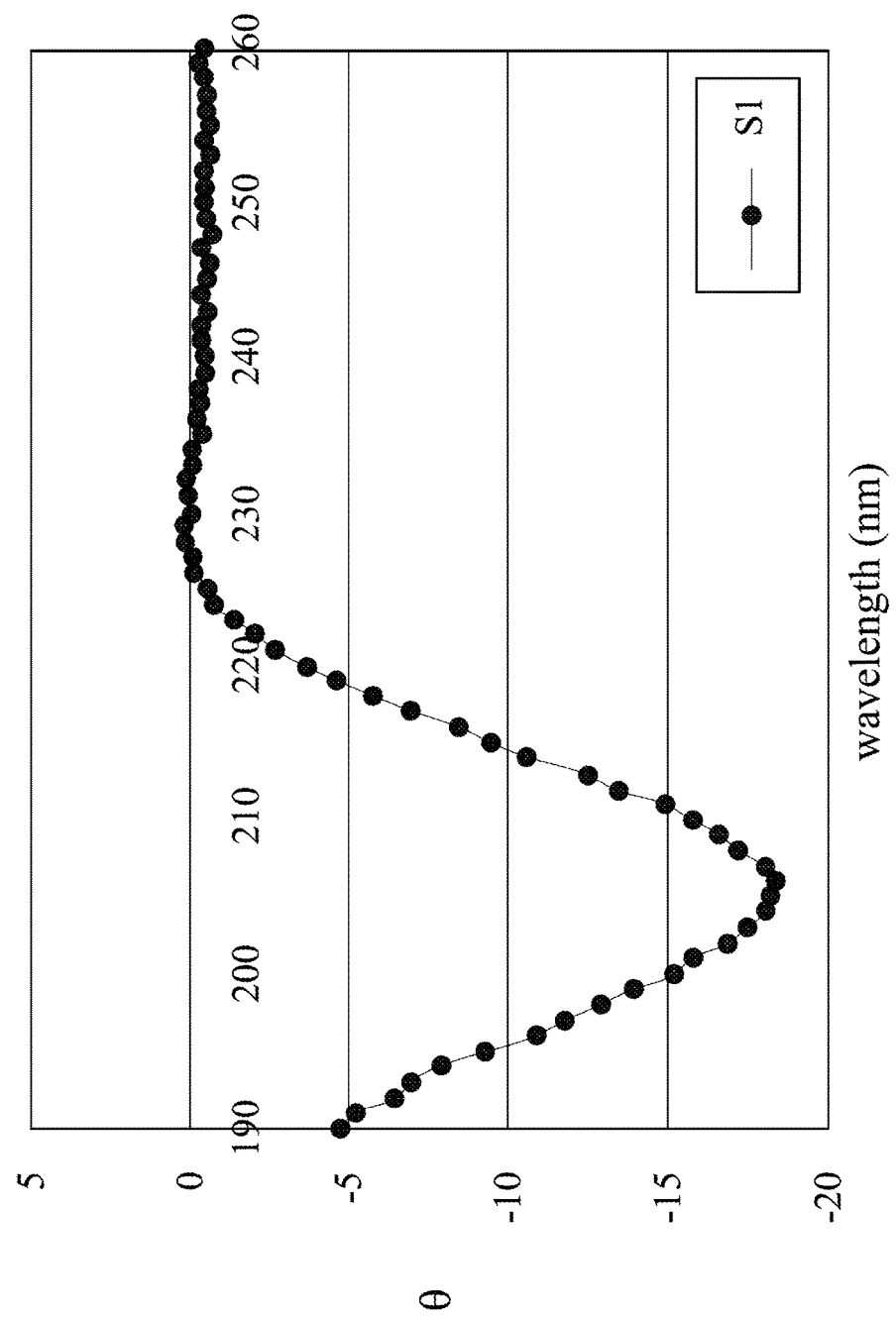
FIG. 14 is a CD (Circular dichroism) spectrum of polygonal scaffold 51 in water of Example 25 according to the present disclosure.

The measuring results of the final product of Example 25 are as follows. Yield: 1.1 mg, 95%. Semi-preparative HPLC: 5-90% B in 30 min, 5 mL/min; $R_t$=14.9 min. Analytical HPLC: 5-90% B in 60 min, 0.5 mL/min; $R_t$=34.7 min. MS(MALDI) Calculated for $C_{159}H_{219}N_{39}O_{33}$: 3202.666, Found: 3228.155 $[M+Na]^+$. FIG. 14 is a CD spectrum of polygonal scaffold S1 in water of Example 25 according to the present disclosure. According to the measuring results and FIG. 14, it can confirm that the final product of Example 25 is the polygonal scaffold S1. The amino acid sequence of the polygonal scaffold S1 is referenced as SEQ ID NO: 25, wherein Xaa at residues 1, 10 and 19 is the derivative 1 of proline, respectively.

Example 26: The Synthesis of Polygonal Scaffold S2

The polygonal scaffold S2 has a structure as follows:

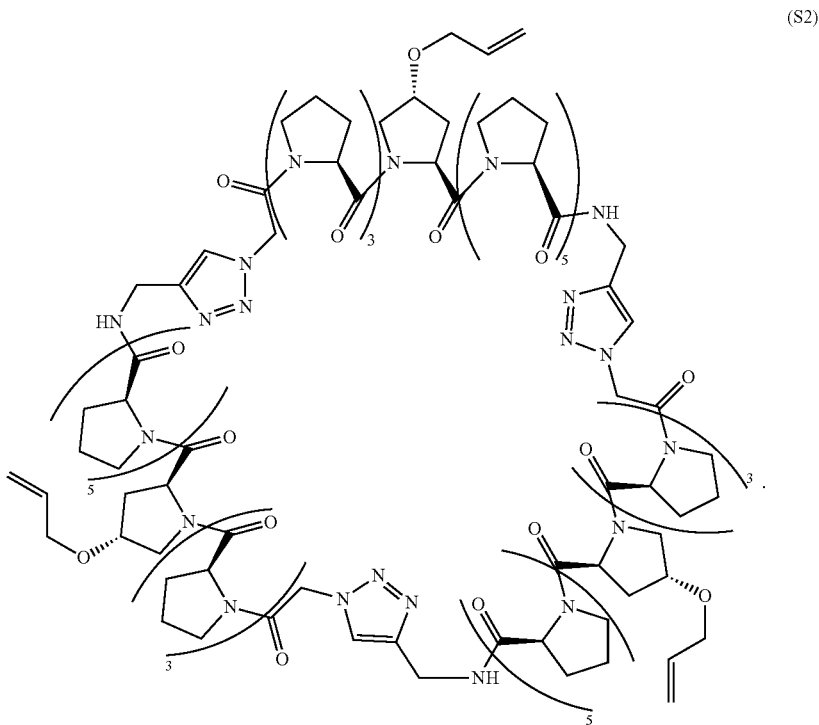

(S2)

The polygonal scaffold S2 can be synthesized by a CuAAC in solution-phase, which similar to Step H in Example 25 but replacing the linear chain L11 with the linear chain L21.

Figure 15:
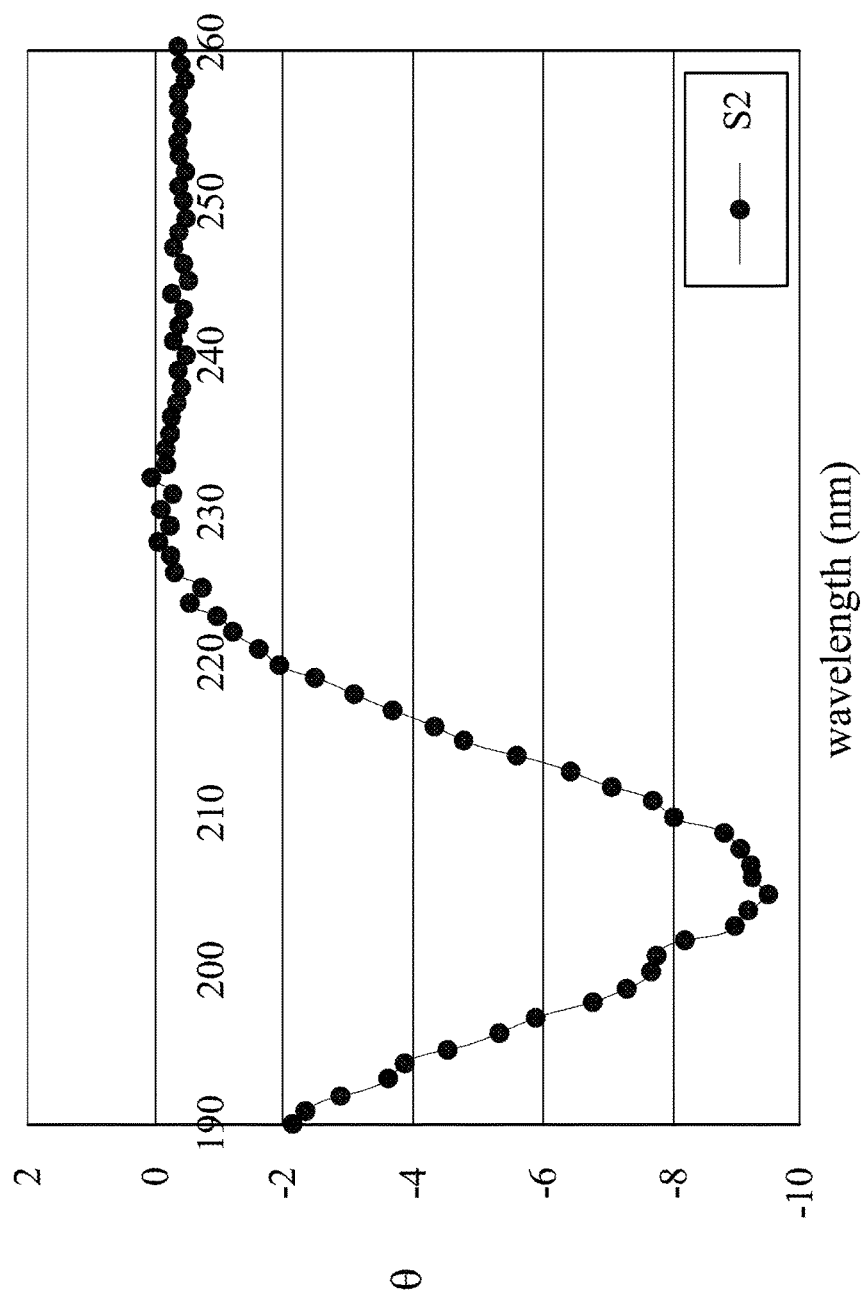
FIG. 15 is a CD spectrum of polygonal scaffold S2 in water of Example 26 according to the present disclosure.

The measuring results of the final product of Example 26 are as follows. Yield: 0.51 mg, 80%. Semi-preparative HPLC: 5-90% B in 30 min, 5 mL/min; $R_t$=14.7 min. Analytical HPLC: 5-90% B in 60 min, 0.5 mL/min; $R_t$=34.5 min. MS(MALDI) Calculated for $C_{159}H_{219}N_{39}O_{33}$: 3202.666, Found: 3204.472 $[M+H]^+$. FIG. 15 is a CD spectrum of polygonal scaffold S2 in water of Example 26 according to the present disclosure. According to the measuring results and FIG. 15, it can confirm that the final product of Example 26 is the polygonal scaffold S2. The amino acid sequence of the polygonal scaffold S2 is referenced as SEQ ID NO: 26, wherein Xaa at residues 4, 13 and 22 is the derivative 1 of proline, respectively.

Example 27: The Synthesis of Polygonal Scaffold S3

The polygonal scaffold S3 has a structure as follows:

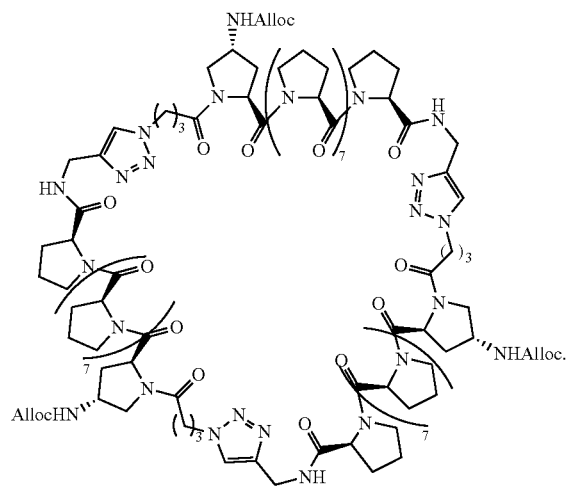

(S3)

The polygonal scaffold S3 can be synthesized by a CuAAC in solution-phase, which similar to Step H in Example 25 but replacing the linear chain L11 with the linear chain L31.

Figure 16:
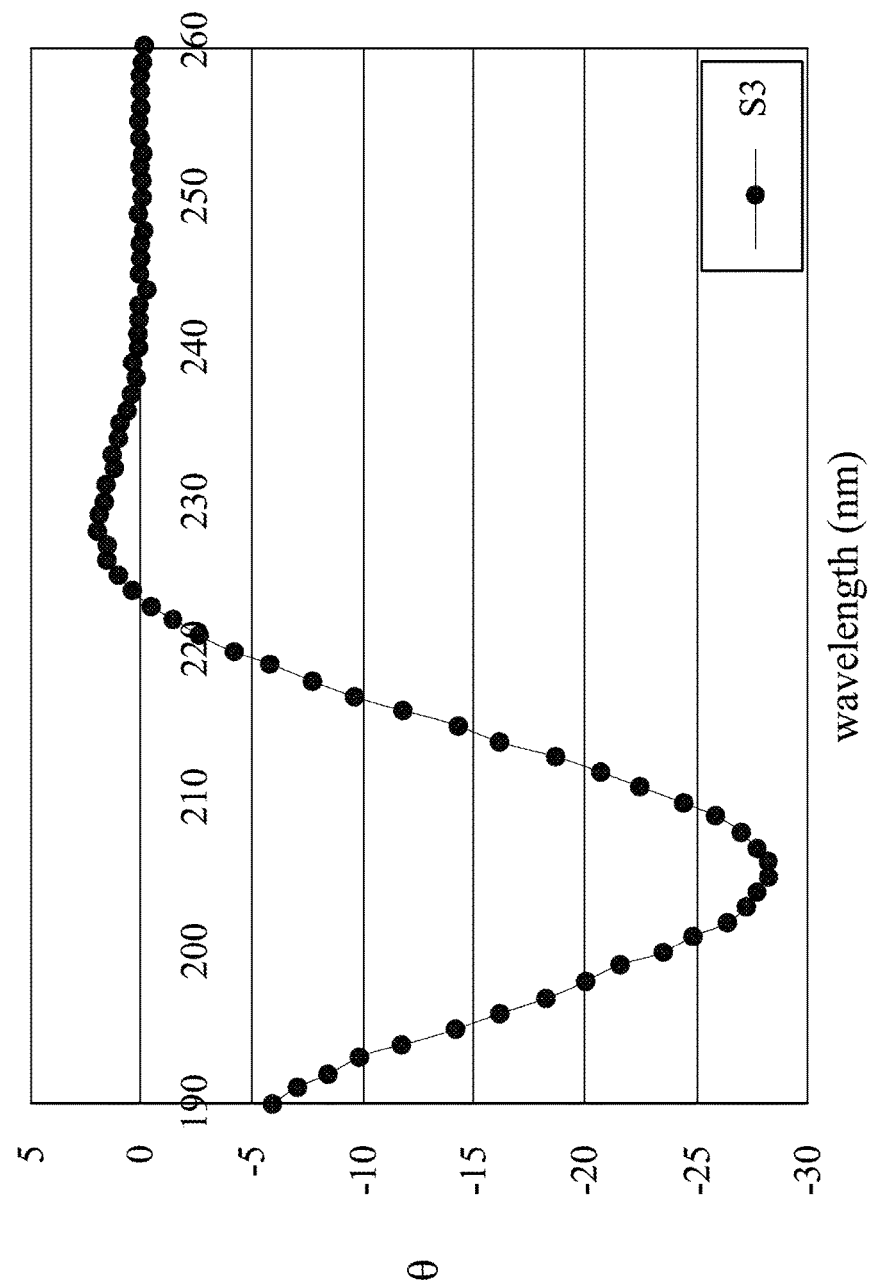
FIG. 16 is a CD spectrum of polygonal scaffold S3 in water of Example 27 according to the present disclosure.

The measuring results of the final product of Example 27 are as follows. Yield: 1.09 mg, 55%. Semi-preparative HPLC: 5-90% B in 30 min, 5 mL/min; $R_t$=14.0 min. Analytical HPLC: 5-90% B in 60 min, 0.5 mL/min; $R_t$=33.9 min. MS(MALDI) Calculated for $C_{168}H_{234}N_{42}O_{36}$: 3415.777, Found: 3416.833 $[M+H]^+$. FIG. 16 is a CD spectrum of polygonal scaffold S3 in water of Example 27 according to the present disclosure. According to the measuring results and FIG. 16, it can confirm that the final product of Example 27 is the polygonal scaffold S3. The amino acid sequence of the polygonal scaffold S3 is referenced as SEQ ID NO: 27, wherein Xaa at residues 1, 10 and 19 is the derivative 2 of proline, respectively.

Example 28: The Synthesis of Polygonal Scaffold S4

The polygonal scaffold S4 has a structure as follows:

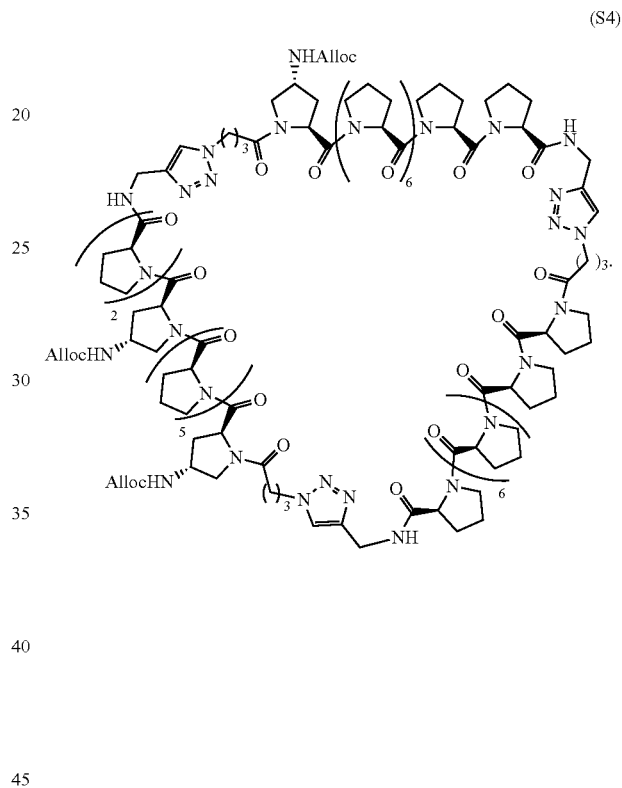

(S4)

The polygonal scaffold S4 can be synthesized by a CuAAC in solution-phase, which similar to Step H in Example 25 but replacing the linear chain L11 with the linear chain L41.

The measuring results of the final product of Example 28 are as follows. Yield: 2.00 mg, 49%. Semi-preparative HPLC: 5-90% B in 30 min, 5 mL/min; $R_t$=15.1 min. MS(MALDI) Calculated for $C_{168}H_{234}N_{42}O_{36}$: 3415.777, Found: 3439.083 $[M+Na]^+$. According to the measuring results, it can confirm that the final product of Example 28 is the polygonal scaffold S4. The amino acid sequence of the polygonal scaffold S4 is referenced as SEQ ID NO: 28, wherein Xaa at residues 10, 16 and 19 is the derivative 2 of proline, respectively.

Example 29: The Synthesis of Polygonal Scaffold S5

The polygonal scaffold S5 has a structure as follows:

(S5)

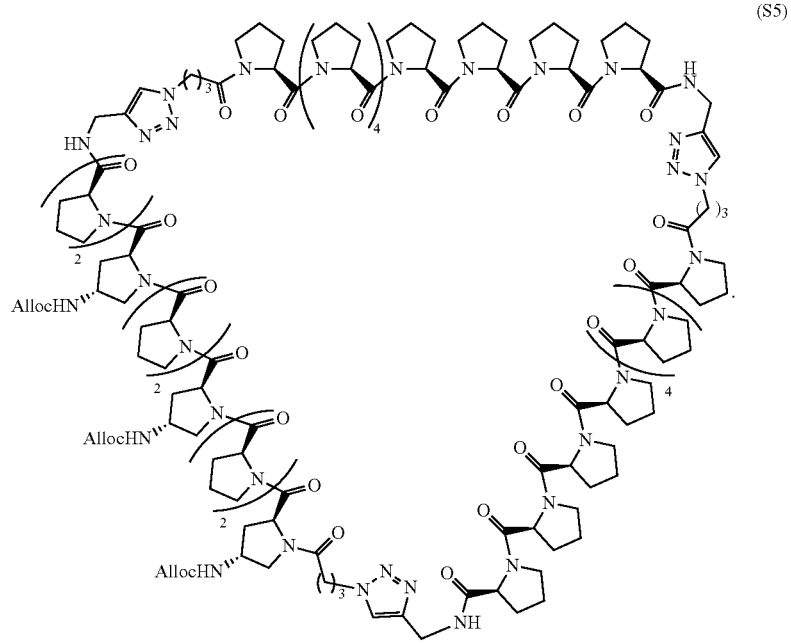

The polygonal scaffold S5 can be synthesized by a CuAAC in solution-phase, which similar to Step H in Example 25 but replacing the linear chain L11 with the linear chain L51.

The measuring results of the final product of Example 29 are as follows. Yield: 1.1 mg, 54%. Semi-preparative HPLC: 5-90% B in 30 min, 5 mL/min; $R_t$=15.2 min. MS(MALDI) Calculated for $C_{168}H_{234}N_{42}O_{36}$: 3415.777, Found: 3436.988 [M+Na]$^+$. According to the measuring results, it can confirm that the final product of Example 29 is the polygonal scaffold S5. The amino acid sequence of the polygonal scaffold S5 is referenced as SEQ ID NO: 29, wherein Xaa at residues 10, 13 and 16 is the derivative 1 of proline, respectively.

Example 30: The Synthesis of Polygonal Scaffold S6

The polygonal scaffold S6 has a structure as follows:

(S6)

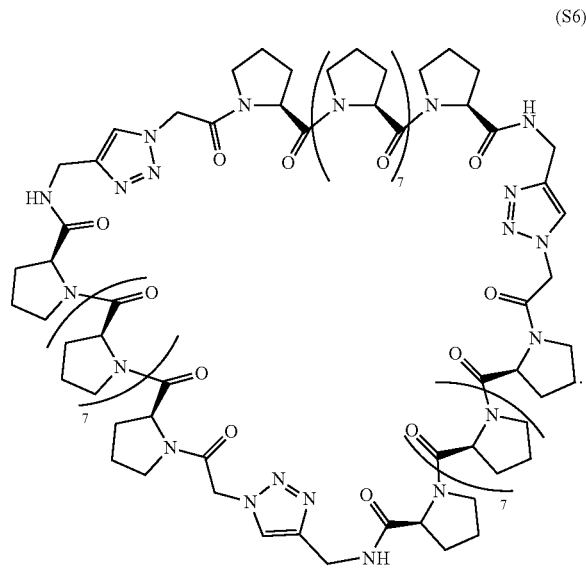

The polygonal scaffold S6 can be synthesized by a CuAAC in solution-phase, which similar to Step H in Example 25 but replacing the linear chain L11 with the PPII helix rod C12.

The measuring results of the final product of Example 30 are as follows. Analytical HPLC: 5-90% B in 60 min, 0.5 mL/min; $R_t$=30.6 min. MS(MALDI) Calculated for $C_{156}H_{222}N_{42}O_{30}$: 3034.587, Found: 3057.865 [M+Na]$^+$. According to the measuring results, it can confirm that the final product of Example 30 is the polygonal scaffold S6. The amino acid sequence of the polygonal scaffold S6 is referenced as SEQ ID NO: 30.

In Example 30, all the hydrogen atoms of the repeat units (i) are not substituted. However, as shown in Examples 2-6, by replacing the Fmoc-Pro-OH (I) with a substituted Fmoc-Pro-OH (such as the Fmoc-Pro-OH (I-1) and the Fmoc-Pro-OH (I-2)) during the SPPS process, it can allow at least one of the PPII helix rod C12 to have at least one hydrogen atom of the repeat units (i) being substituted by a first chemical handle. In other words, the polygonal scaffold S6 is allowed to have at least one hydrogen atom of the repeat units (i) being substituted by the first chemical handle, which is the polygonal scaffold according to the present disclosure.

Moreover, as shown in Example 30, the polygonal scaffold S6 is obtained by connecting the PPII helix rods C12 end-to-end to form a closed ring in one step. That is, according to the present disclosure, the assembling step (corresponding to Step 220) in FIG. 5 can be implemented in one-step manner, such as adopting the PPII helix rods with a terminal alkyl group and a terminal azide group. In other words, the extension step (corresponding to Step 221 in FIG. 6) followed by the cyclization step (corresponding to Step 222 in FIG. 6) is not essential for synthesizing the polygonal scaffold.

Example 31: The Synthesis of Polygonal Scaffold S11

The polygonal scaffold S11 has a structure as follows:

(S11)

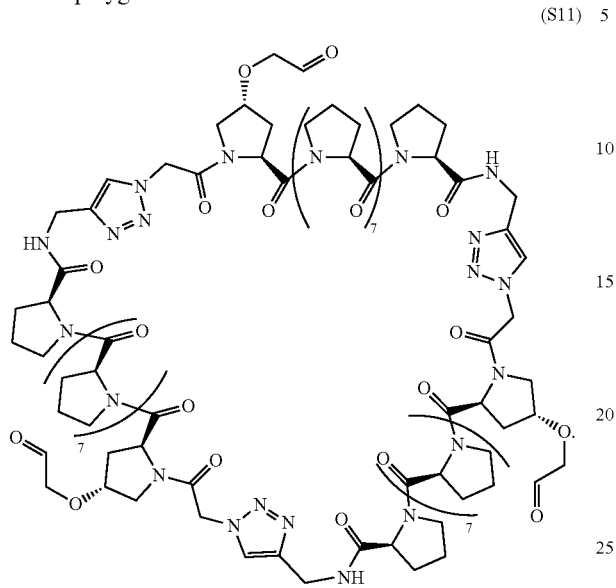

Example 32: The Synthesis of Polygonal Scaffold S31

The polygonal scaffold S31 has a structure as follows:

(S31)

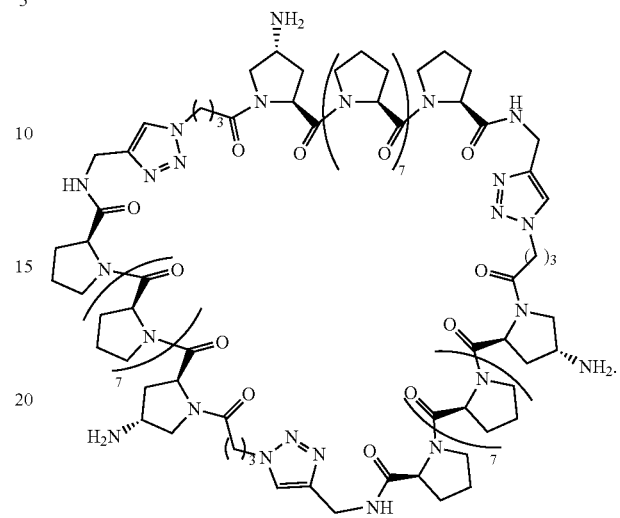

The polygonal scaffold S11 can be synthesized by Step I.

In Step I, ozonolysis is conducted. Specifically, the polygonal scaffold 51 is dissolved in MeOH (polygonal scaffold 51 concentration 0.1 mM) at −78° C. and subjected to an ozone stream. When the color of solution turned deep blue (usually in few minutes) turn off the ozone stream and stir under Ar for 10 min. Adding activated zinc powder and 50% AcOH(aq), stir at room temperature for 30 min. Remove the solvent under reduced pressure then purified by HPLC.

The measuring results of the final product of Example 31 are as follows. Yield: 1.1 mg, quanti. Analytical HPLC: 5-90% B in 60 min, 0.5 mL/min; $R_t$=22.4 min. MS(MALDI) Calculated for $C_{156}H_{213}N_{39}O_{36}$: 3208.604, Found: 3248.962 [M+K]$^+$. According to the measuring results, it can confirm that the final product of Example 31 is the polygonal scaffold S11. The amino acid sequence of the polygonal scaffold S11 is referenced as SEQ ID NO: 31, wherein Xaa at residues 1, 10 and 19 is the derivative 3 of proline, respectively.

The polygonal scaffold S31 can be synthesized by Step J.

In Step J, Alloc deprotection is conducted. Specifically, the polygonal scaffold S3 and Pd(PPh$_3$)$_2$Cl$_2$ (0.1 equiv.) is dissolved in DCM (polygonal scaffold S3 concentration 40 mM) followed by acetic acid (4 equiv.) and Bu$_3$SnH (3 equiv.) is added to the vial. The mixture was stirred 2 h, after addition of water to quench the reaction and removal of DCM under reduced pressure and centrifuge, the crude product is purified by HPLC.

The measuring results of the final product of Example 32 are as follows. Yield: 0.76 mg, 75%. Analytical HPLC: 5-90% B in 60 min, 0.5 mL/min; $R_t$=22.4 min. MS(MALDI) Calculated for $C_{156}H_{222}N_{42}O_{30}$: 3163.714, Found: 3164.758 [M+H]$^+$. According to the measuring results, it can confirm that the final product of Example 32 is the polygonal scaffold S31. The amino acid sequence of the polygonal scaffold S31 is referenced as SEQ ID NO: 32, wherein Xaa at residues 1, 10 and 19 is the derivative 4 of proline, respectively.

Example 33: The Synthesis of Polygonal Scaffold S41

The polygonal scaffold S41 has a structure as follows:

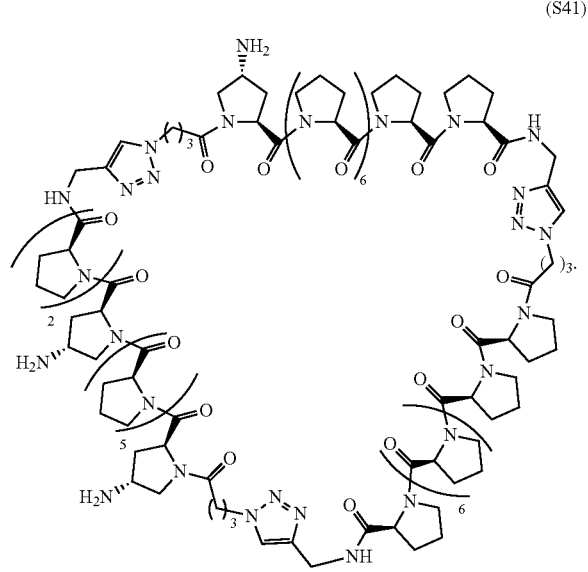

(S41)

The polygonal scaffold S41 can be synthesized by an Alloc deprotection step, which is similar to Step J in Example 32 but replacing the polygonal scaffold S3 with the polygonal scaffold S4.

The measuring results of the final product of Example 33 are as follows. Yield: 0.90 mg, 49%. Analytical HPLC: 5-90% B in 60 min, 0.5 mL/min; $R_t$=22.1 min. MS(MALDI) Calculated for $C_{156}H_{222}N_{42}O_{30}$: 3163.714, Found: 3185.297 $[M+Na]^+$. According to the measuring results, it can confirm that the final product of Example 33 is the polygonal scaffold S41. The amino acid sequence of the polygonal scaffold S41 is referenced as SEQ ID NO: 33, wherein Xaa at residues 10, 16 and 19 is the derivative 4 of proline, respectively.

Example 34: The Synthesis of Polygonal Scaffold S51

The polygonal scaffold S51 has a structure as follows:

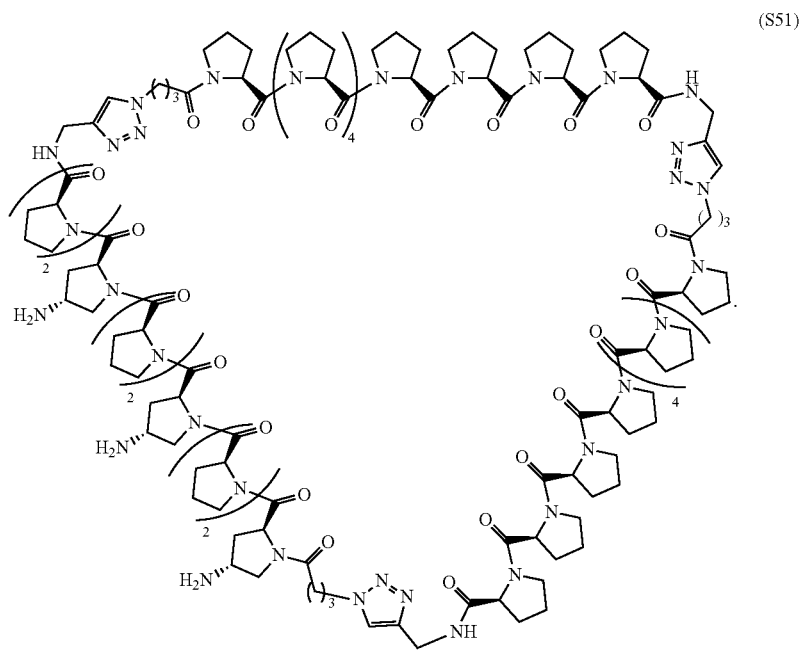

(S51)

The polygonal scaffold S51 can be synthesized by an Alloc deprotection step, which is similar to Step J in Example 32 but replacing the polygonal scaffold S3 with the polygonal scaffold S5.

The measuring results of the final product of Example 34 are as follows. Yield: 0.47 mg, 46%. Analytical HPLC: 5-90% B in 60 min, 0.5 mL/min; $R_t$=24.2 min. MS(MALDI) Calculated for $C_{156}H_{222}N_{42}O_{30}$: 3163.714, Found: 3186.392 $[M+Na]^+$. According to the measuring results, it can confirm that the final product of Example 34 is the polygonal scaffold S51. The amino acid sequence of the polygonal scaffold S51 is referenced as SEQ ID NO: 34, wherein Xaa at residues 10, 13, 16 and 19 is the derivative 4 of proline, respectively.

Example 35: The Synthesis of Polygonal Scaffold S32

The polygonal scaffold S32 has a structure as follows:

(S32)

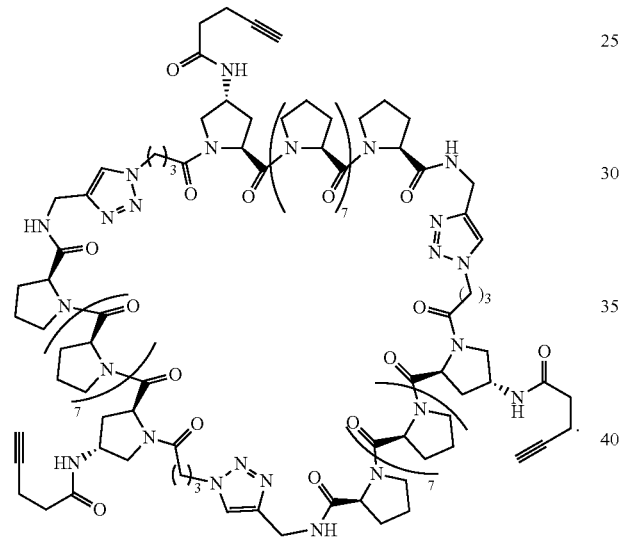

The polygonal scaffold S32 can be synthesized by an alkynylation reaction, which is similar to Step F in Example 8 but replacing the PPII helix rod C11 with the polygonal scaffold S31 and replacing propargylamine with 4-pentynoic acid.

The measuring results of the final product of Example 35 are as follows. Yield: 0.66 mg, 80%. Analytical HPLC: 5-90% B in 60 min, 0.5 mL/min; $R_t$=31.7 min. MS(MALDI) Calculated for $C_{171}H_{234}N_{42}O_{33}$: 3403.792, Found: 3405.165 $[M+H]^+$. According to the measuring results, it can confirm that the final product of Example 35 is the polygonal scaffold S32. The amino acid sequence of the polygonal scaffold S32 is referenced as SEQ ID NO: 35, wherein Xaa at residues 1, 10 and 19 is the derivative 5 of proline, respectively.

Example 36: The Synthesis of Polygonal Scaffold S42

The polygonal scaffold S42 has a structure as follows:

(S42)

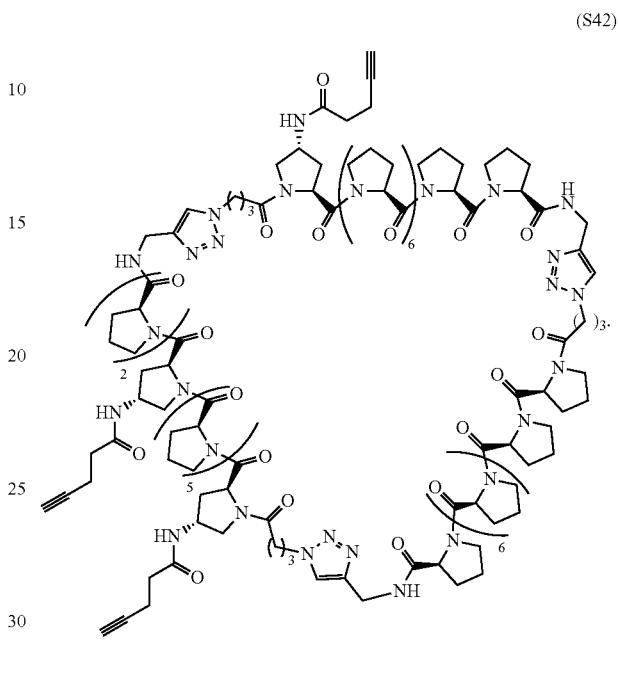

The polygonal scaffold S42 can be synthesized by an alkynylation reaction, which is similar to Step F in Example 8 but replacing the PPII helix rod C11 with the polygonal scaffold S41 and replacing propargylamine with 4-pentynoic acid.

The measuring results of the final product of Example 36 are as follows. Yield: 0.47 mg, 54%. Analytical HPLC: 5-90% B in 60 min, 0.5 mL/min; $R_t$=32.3 min. MS(MALDI) Calculated for $C_{171}H_{234}N_{42}O_{33}$: 3403.792, Found: 3428.036 $[M+Na]^+$. According to the measuring results, it can confirm that the final product of Example 36 is the polygonal scaffold S42. The amino acid sequence of the polygonal scaffold S42 is referenced as SEQ ID NO: 36, wherein Xaa at residues 10, 16 and 19 is the derivative 5 of proline, respectively.

Example 37: The Synthesis of Polygonal Scaffold S52

The polygonal scaffold S52 has a structure as follows:

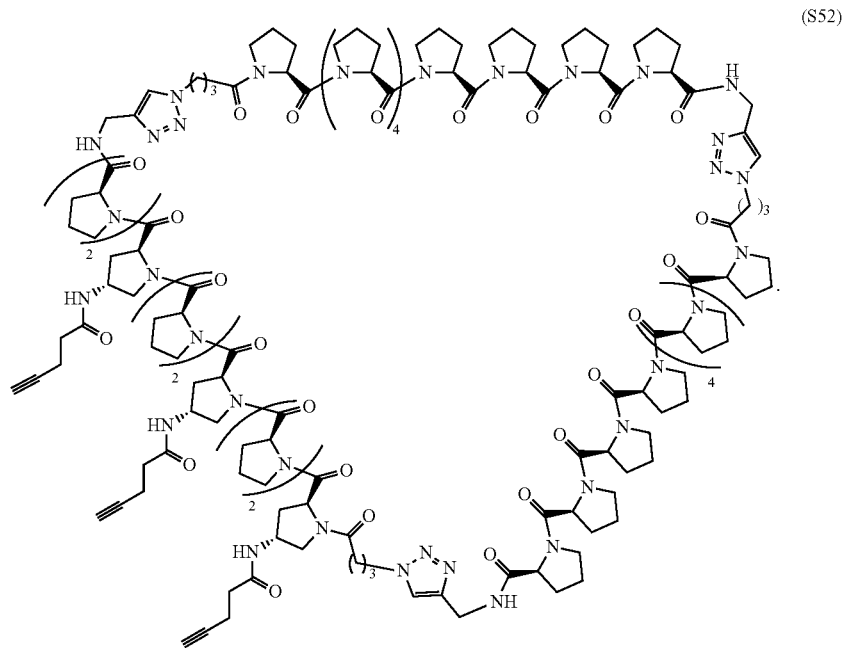

(S52)

The polygonal scaffold S52 can be synthesized by an alkynylation reaction, which is similar to Step F in Example 8 but replacing the PPII helix rod C11 with the polygonal scaffold S51 and replacing propargylamine with 4-pentynoic acid.

The measuring results of the final product of Example 37 are as follows. Yield: 0.71 mg, 81%. Analytical HPLC: 5-90% B in 60 min, 0.5 mL/min; $R_f$=32.0 min. MS(MALDI) Calculated for $C_{171}H_{234}N_{42}O_{33}$: 3403.792, Found: 3429.040 [M+Na]$^+$. According to the measuring results, it can confirm that the final product of Example 37 is the polygonal scaffold S52. The amino acid sequence of the polygonal scaffold S52 is referenced as SEQ ID NO: 37, wherein Xaa at residues 10, 13 and 16 is the derivative 5 of proline, respectively.

Example 38: The Synthesis of Protein Modulator SL1

The protein modulator SL1 has a structure as follows:

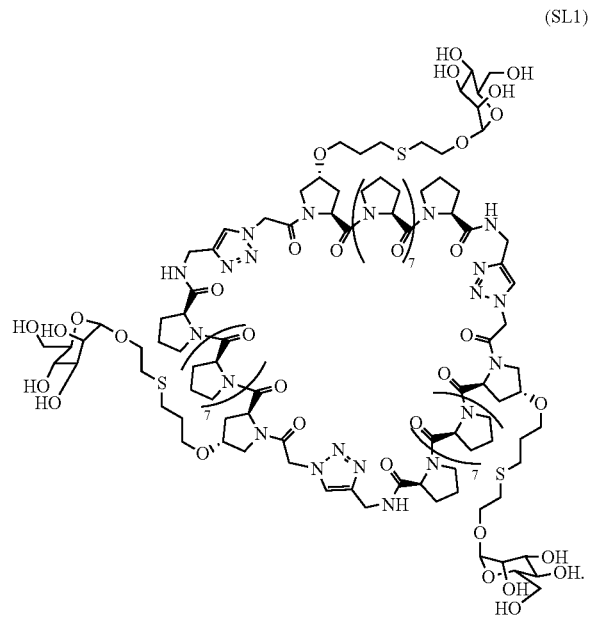

(SL1)

The protein modulator SL1 can be synthesized by Step K. In Step K, a thiol-ene reaction is conducted. Specifically, the polygonal scaffold S1, ligand-providing compound (iv-1a) (10 equiv.), and radical initiator VA-044 (2,2'-azobis[2-(2-imidazolin-2-yl)propane]dihydrochloride) (6 equiv.) is dissolved in acetate buffer (pH=4-5, polygonal scaffold S1 concentration 3.0 mM). The reaction is performed under 365 nm UV light for 1 h, the crude product is purified by HPLC.

The measuring results of the final product of Example 38 are as follows. Analytical HPLC: 20-90% B in 60 min, 0.5 mL/min; $R_t$=16.9 min. MS(MALDI) Calculated for $C_{183}H_{267}N_{39}O_{51}S_3$: 3922.866, Found: 3961.892 [M+K]$^+$. According to the measuring results, it can confirm that the final product of Example 38 is the protein modulator SL1. The amino acid sequence of the protein modulator SL1 is referenced as SEQ ID NO: 38, wherein Xaa at residues 1, 10 and 19 is the derivative 6 of proline, respectively.

Example 39: The Synthesis of Protein Modulator SL2

The protein modulator SL2 has a structure as follows:

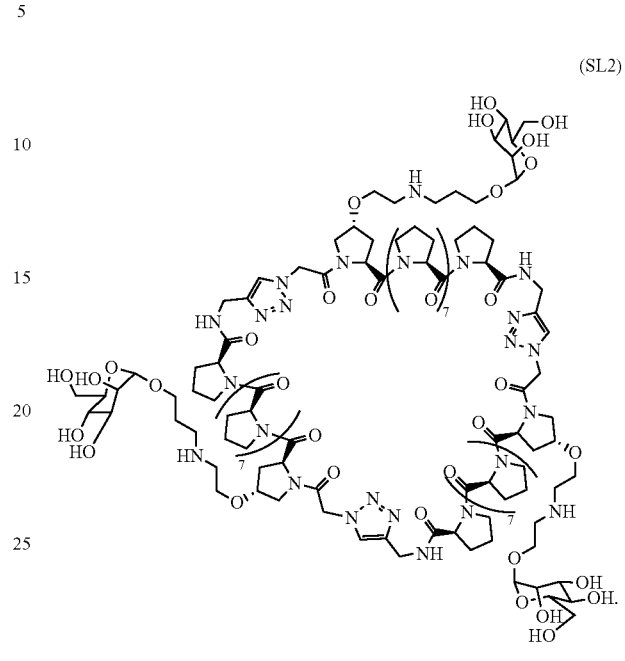

(SL2)

The protein modulator SL2 can be synthesized by Step L. In Step L, a reductive amination is conducted. Specifically, the polygonal scaffold S11 is dissolved in MeOH or water, treated with ligand-providing compound (iv-1b) (5-15 equiv.) and NaBH$_3$CN (1.5 equiv., from 1 M solution in water) for 1-8 h. Quenched the excess amount reductant by acetone, the crude product is purified by HPLC.

The measuring results of the final product of Example 39 are as follows. Analytical HPLC: 5-90% B in 60 min, 0.5 mL/min; $R_t$=21.2 min. MS(MALDI) Calculated for $C_{180}H_{264}N_{42}O_{51}$: 3829.936, Found: 3830.827 [M+H]$^+$. According to the measuring results, it can confirm that the final product of Example 39 is the protein modulator SL2. The amino acid sequence of the protein modulator SL2 is referenced as SEQ ID NO: 39, wherein Xaa at residues 1, 10 and 19 is the derivative 7 of proline, respectively.

Example 40: The Synthesis of Protein Modulator SL3

The protein modulator SL3 has a structure as follows:

(SL3)

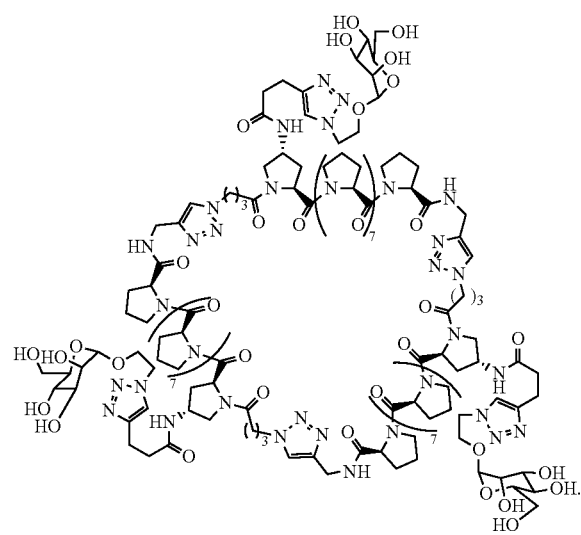

The protein modulator SL3 can be synthesized by a CuAAC in solution-phase. Specifically, the polygonal scaffold S32 is prepared as 2 mM aqueous solution, and treated with CuSO$_4$.5H$_2$O (4.2 equiv., from 40 mM solution water), ligand triethyl 2,2',2''-(4,4',4''-nitrilotris(methylene)tris(1H-1,2,3-triazole-4,1-diyl))triacetate (4.2 equiv., from 40 mM solution in DMSO), sodium ascorbate (84 equiv., from 800 mM solution in water), $^i$Pr$_2$NEt (144 equiv.), and ligand-providing compound (iv-1c) (final copper concentration 5 mM) at 40° C. for 1 h, the crude product is purified by HPLC.

The measuring results of the final product of Example 40 are as follows. Analytical HPLC: 5-90% B in 60 min, 0.5 mL/min; R$_t$=26.2 min. MS(MALDI) Calculated for C$_{195}$H$_{279}$N$_{51}$O$_{51}$: 4151.081, Found: 4151.907 [M+H]$^+$. According to the measuring results, it can confirm that the final product of Example 40 is the protein modulator SL3. The amino acid sequence of the protein modulator SL3 is referenced as SEQ ID NO: 40, wherein Xaa at residues 1, 10 and 19 is the derivative 8 of proline, respectively.

Example 41: The Synthesis of Protein Modulator SL4

The protein modulator SL4 has a structure as follows:

(SL4)

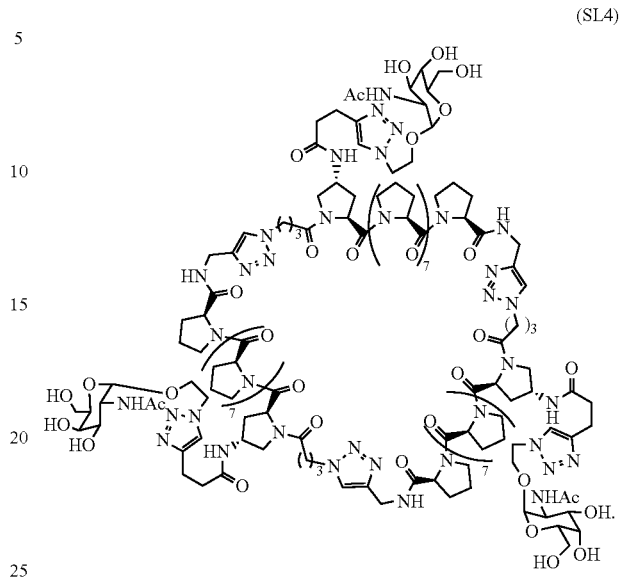

The protein modulator SL4 can be synthesized by a CuAAC in solution-phase, which is similar to that in Example 40 but replacing the ligand-providing compound (iv-1c) with the ligand-providing compound (iv-7a).

The measuring results of the final product of Example 41 are as follows. Yield: 0.37 mg, 96%. Analytical HPLC: 5-90% B in 60 min, 0.5 mL/min; R$_t$=26.2 min. MS(MALDI) Calculated for C$_{201}$H$_{288}$N$_{54}$O$_{51}$: 4274.160, Found: 4297.245 [M+Na]$^+$. According to the measuring results, it can confirm that the final product of Example 41 is the protein modulator SL4. The amino acid sequence of the protein modulator SL4 is referenced as SEQ ID NO: 41, wherein Xaa at residues 1, 10 and 19 is the derivative 9 of proline, respectively.

Example 42: The Synthesis of Protein Modulator SL5

The protein modulator SL5 has a structure as follows:

(SL5)

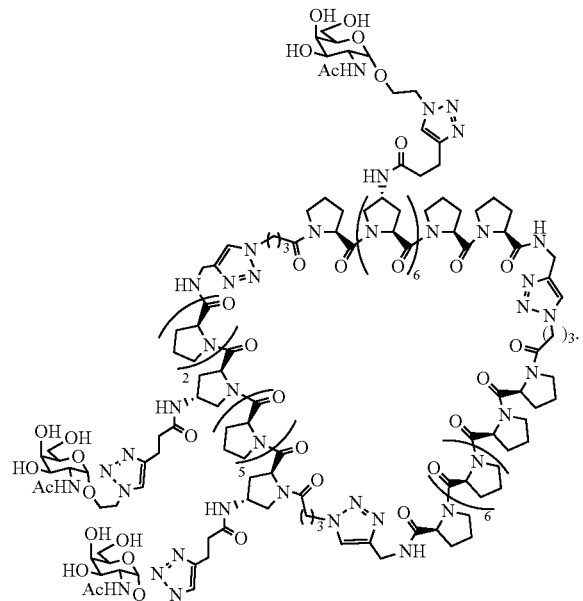

The protein modulator SL5 can be synthesized by a CuAAC in solution-phase, which is similar to that in Example 41 but replacing the polygonal scaffold S32 with the polygonal scaffold S42.

The measuring results of the final product of Example 42 are as follows. Yield: 0.27 mg, 70%. Analytical HPLC: 5-90% B in 60 min, 0.5 mL/min; $R_t$=25.5 min. MS(MALDI) Calculated for $C_{201}H_{288}N_{54}O_{51}$: 4274.160, Found: 4298.057 [M+Na]$^+$. According to the measuring results, it can confirm that the final product of Example 42 is the protein modulator SL5. The amino acid sequence of the protein modulator SL5 is referenced as SEQ ID NO: 42, wherein Xaa at residues 10, 16 and 19 is the derivative 9 of proline, respectively.

Example 43: The Synthesis of Protein Modulator SL6

The protein modulator SL6 has a structure as follows:

The protein modulator SL6 can be synthesized by a CuAAC in solution-phase, which is similar to that in Example 41 but replacing the polygonal scaffold S32 with the polygonal scaffold S52.

The measuring results of the final product of Example 52 are as follows. Yield: 0.16 mg, 42%. Analytical HPLC: 5-90% B in 60 min, 0.5 mL/min; $R_t$=28.2 min. MS(MALDI) Calculated for $C_{201}H_{288}N_{54}O_{51}$: 4274.160, Found: 4298.512 [M+Na]$^+$. According to the measuring results, it can confirm that the final product of Example 43 is the protein modulator SL6. The amino acid sequence of the protein modulator SL6 is referenced as SEQ ID NO: 43, wherein Xaa at residues 10, 13 and 16 is the derivative 9 of proline, respectively.

In each of Examples 1-7 and 15-19, the yield is based on quantitative Fmoc test and after lyophilization. In each of Examples 8-14 and 20-43, the yield is based on after lyophilization.

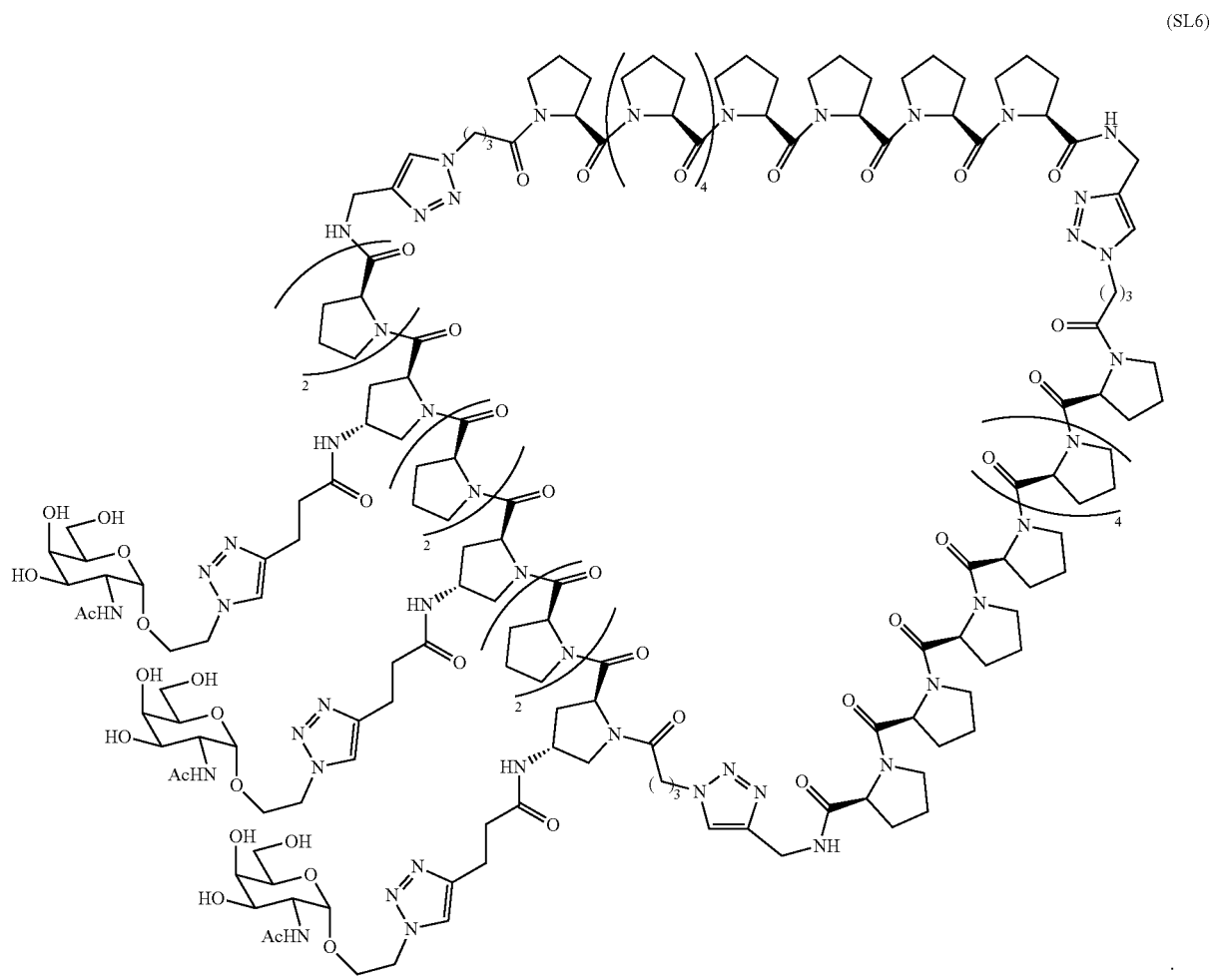

(SL6)

Comparative Example 1

A protein modulator COM1 with a flexible scaffold has a structure as follows:

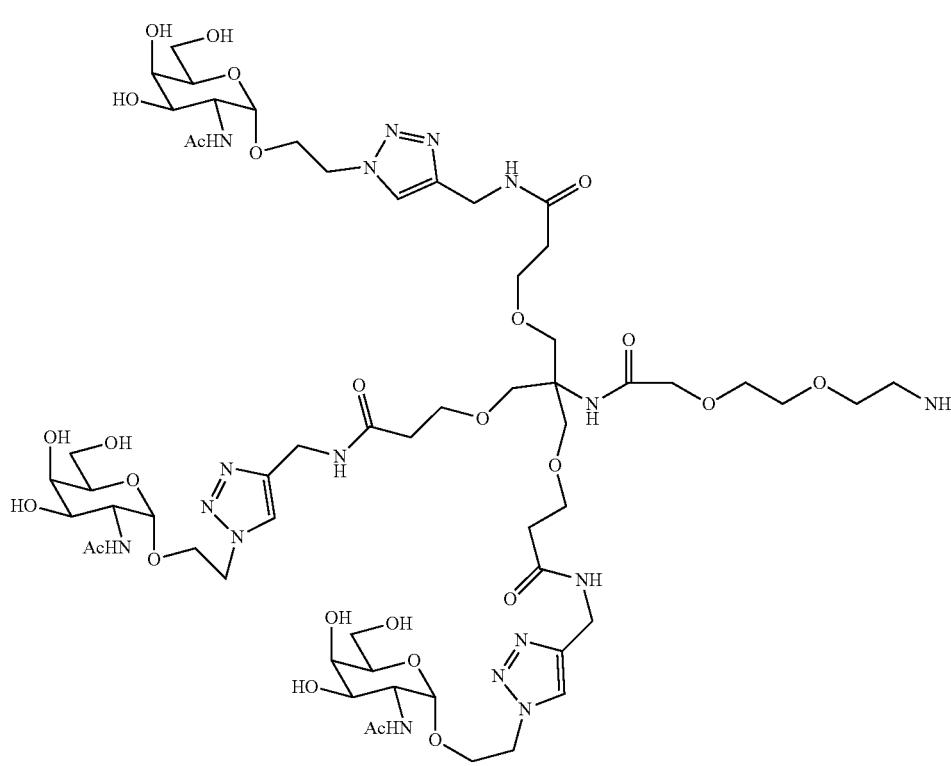

Surface Plasmon Resonance Experiment

Assay: surface plasmon resonance (SPR) experiments were performed on the Biacore T200 at 25° C. using a functionalized CM5 sensor chip. Protein immobilization was performed according to the instrument build-in wizard template. The CM5 sensor chip was activated with a solution containing N-ethyl-N'-(3-diethyl-aminopropyl)-carbodiimide (EDC) (0.2 M) and N-hydroxysuccinimide (NHS) (0.05 M). HPA (10 μg/mL) in NaOAc buffer (pH 6) or SBA (10 μg/mL) in NaOAc buffer (pH 4) was injected over the activated flow cell at flow rate of 10 μL/min for 420 s. Then 1 M ethanolamine at pH 8.5 was injected to block the remaining activated groups. Binding assays were performed with HBS-P+(10 mM HEPES, 150 mM NaCl, 0.05% tween 20, pH 7.4) for HPA or 10 mM HEPES, 150 mM NaCl, 0.05% tween 20, and 100 μM $CaCl_2$, 0.05% tween 20, pH 7.5 for SBA as running buffer. Protein modulator for test (COM1, SL4, SL5 and SL6) were injected onto the surface, with several concentrations of ranging from 6.25 nM to 100 nM for protein modulator COM1 and 10 nM to 160 nM for protein modulators SL4, SL5 and SL6 to HPA or from 62.5 nM to 1000 nM for protein modulator COM1 and 100 nM to 1600 nM for protein modulators SL4, SL5 and SL6 to SBA at the rate of 30 μL/min diluted in the running buffer. The surface was regenerated by 30 s injection of 300 mM GlcNAc for HPA or 100 mM methyl β-D-galactopyranoside for LecA. The sensorgrams were reference subtracted, quality controlled and analyzed by Biacore T200 Evaluation Software, and the kinetic parameters were obtained by fitting curves to 1:1 Langmuir model.

The results of SPR experiments are shown in Table 2.

TABLE 2

| protein modulator | KD(nM) | |
|---|---|---|
| | HPA | SBA |
| COM1 (flexible) | 7.34 | 61.21 |
| SL4 (rigid and correct design to HPA) | 8.25 | 98.05 |
| SL5 (rigid and wrong design to HPA) | 22.0 | 138.3 |
| SL6 (rigid and wrong design to HPA) | 79.36 | 255.1 |

Note:
HPA is an abbreviation of *Helix pomatia* agglutinin.
SBA is an abbreviation of soybean agglutinin.

Among the protein modulators SL4, SL5 and SL6, the protein modulator SL4 is designed for HPA. That is, the protein modulator SL4 is regarded as the correct design for HPA, and the protein modulators SL5 and SL6 are reg SBA and for HPA is greater than that of the protein modulator COM1 for SBA and for HPA, which shows the spatial selectivity of the protein modulator SL4 is better than that of the protein modulator COM1.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A polygonal scaffold, comprising:
   at least three polyproline II (PPII) helix rods, wherein each of the PPII helix rods is composed of a plurality of repeat units represented by Formula (i):

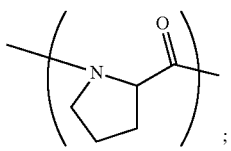
   (i)

wherein at least one of the PPII helix rods has at least one hydrogen atom of at least one of the repeat units being substituted by a first chemical handle for connecting a ligand; and
   at least three connectors, wherein each of the connectors is a divalent organic group, and each PPII helix rod is connected by two connectors to two other PPII helix rods to form a closed ring.

2. The polygonal scaffold of claim 1, wherein a number of the repeat units of each of the PPII helix rods is 6 to 18.

3. The polygonal scaffold of claim 1, wherein the first chemical handle has a structure represented by Formula (ii-1), Formula (ii-2), Formula (ii-3), Formula (ii-4), Formula (ii-5) or Formula (ii-6):

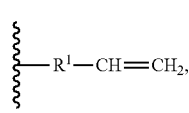
(ii-1)

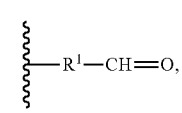
(ii-2)

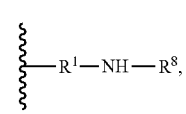
(ii-3)

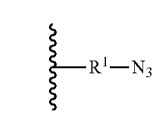
(ii-4)

(ii-5)
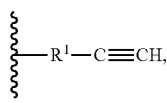

(ii-6)
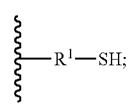

wherein $R^1$ is independently a single bond or a divalent hydrocarbon group having 1 to 6 carbon atoms, each —$CH_2$— of the divalent hydrocarbon group is unsubstituted or substituted by —O—, —NH— or —CO—, and $R^8$ is a protecting group or H.

4. The polygonal scaffold of claim 3, wherein the first chemical handle has the structure represented by Formula (ii-1-1), Formula (ii-2-1), Formula (ii-3-1) or Formula (ii-5-1):

(ii-1-1)
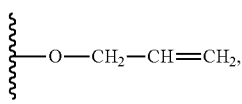

(ii-2-1)
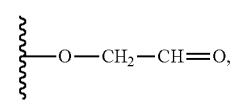

(ii-3-1)

(ii-5-1)
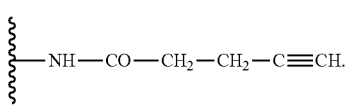

5. The polygonal scaffold of claim 1, wherein at least one connector has a structure represented by Formula (iii-1):

(iii-1)
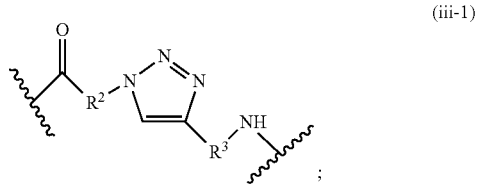

wherein $R^2$ and $R^3$ are independently a single bond or a divalent hydrocarbon group having 1 to 6 carbon atoms.

6. The polygonal scaffold of claim 1, wherein the ligand is provided by a ligand-providing compound having a structure represented by Formula (iv-1), Formula (iv-2), Formula (iv-3), Formula (iv-4), Formula (iv-5), Formula (iv-6) or Formula (iv-7):

(iv-1)
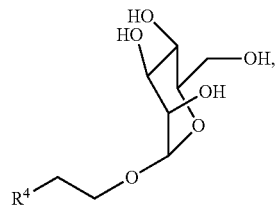

(iv-2)
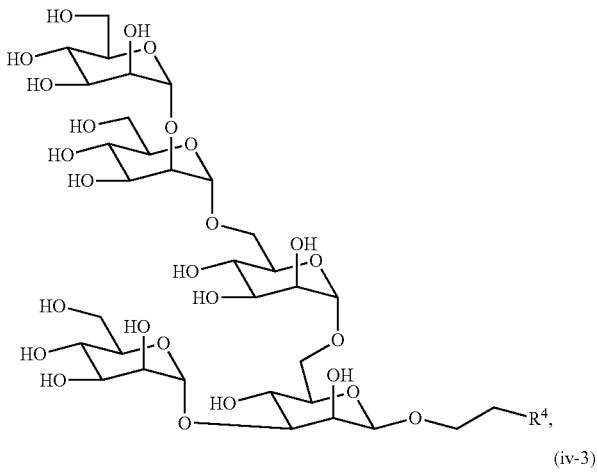

(iv-3)
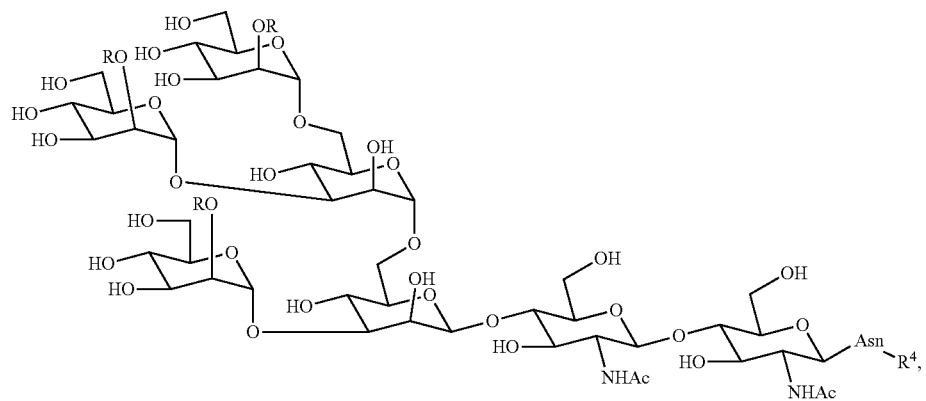

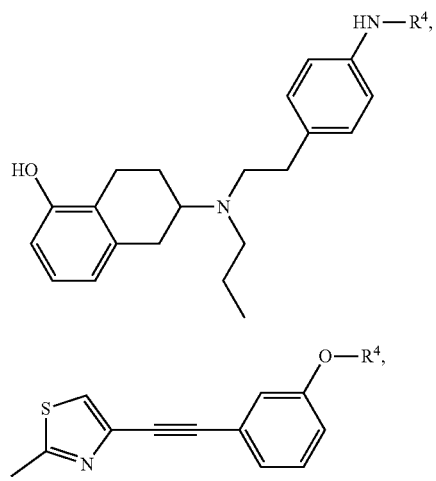

(iv-4)

(iv-5)

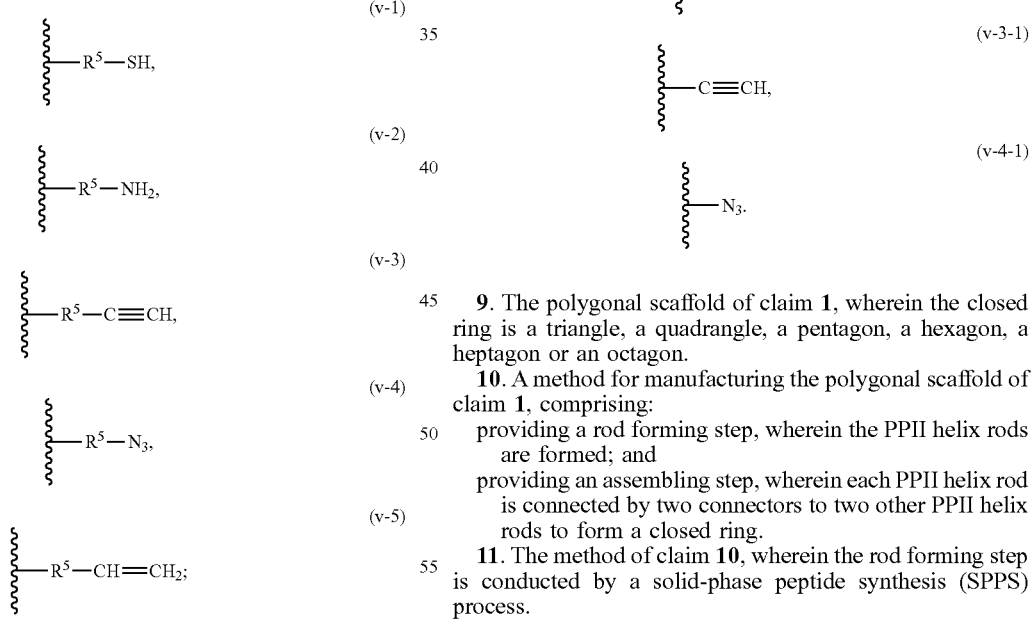

(iv-6)

(iv-7)

wherein R⁴ is a second chemical handle for reacting with the first chemical handle of at least one of the PPII helix rods, and R is H or a 1-2 Man.

7. The polygonal scaffold of claim 6, wherein R⁴ has a structure represented by Formula (v-1), Formula (v-2), Formula (v-3), Formula (v-4) or Formula (v-5):

$$\text{⸺} R^5\text{⸺}SH, \quad (v\text{-}1)$$

$$\text{⸺} R^5\text{⸺}NH_2, \quad (v\text{-}2)$$

$$\text{⸺} R^5\text{⸺}C{\equiv}CH, \quad (v\text{-}3)$$

$$\text{⸺} R^5\text{⸺}N_3, \quad (v\text{-}4)$$

$$\text{⸺} R^5\text{⸺}CH{=}CH_2; \quad (v\text{-}5)$$

wherein $R^5$ is independently a single bond or a divalent hydrocarbon group having 1 to 6 carbon atoms, and each —CH₂— of the divalent hydrocarbon group is unsubstituted or substituted by —O—, —NH— or —CO—.

8. The polygonal scaffold of claim 7, wherein R⁴ has the structure represented by Formula (v-1-1), Formula (v-2-1), Formula (v-3-1) or Formula (v-4-1):

$$\text{⸺}SH, \quad (v\text{-}1\text{-}1)$$

$$\text{⸺}NH_2, \quad (v\text{-}2\text{-}1)$$

$$\text{⸺}C{\equiv}CH, \quad (v\text{-}3\text{-}1)$$

$$\text{⸺}N_3. \quad (v\text{-}4\text{-}1)$$

9. The polygonal scaffold of claim 1, wherein the closed ring is a triangle, a quadrangle, a pentagon, a hexagon, a heptagon or an octagon.

10. A method for manufacturing the polygonal scaffold of claim 1, comprising:
providing a rod forming step, wherein the PPII helix rods are formed; and
providing an assembling step, wherein each PPII helix rod is connected by two connectors to two other PPII helix rods to form a closed ring.

11. The method of claim 10, wherein the rod forming step is conducted by a solid-phase peptide synthesis (SPPS) process.

12. The method of claim 10, wherein the assembling step comprising:
providing an extension step, wherein at least one PPII helix rod is connected by two connectors to two other PPII helix rods to form a linear chain; and
providing a cyclization step, wherein two ends of the linear chain are connected by one of the connectors to form the closed ring.

13. The method of claim 12, wherein the extension step is conducted by a Cu(I)-catalyzed azidealkyne cycloaddition (CuAAC) in solid-phase.

14. The method of claim 12, wherein the cyclization step is conducted by a CuAAC in solution-phase.

15. The method of claim 10, wherein a number of the repeat units of each of the PPII helix rods is 6 to 18.

16. The method of claim 10, wherein the first chemical handle has a structure represented by Formula (ii-1), Formula (ii-2), Formula (ii-3), Formula (ii-4), Formula (ii-5) or Formula (ii-6):

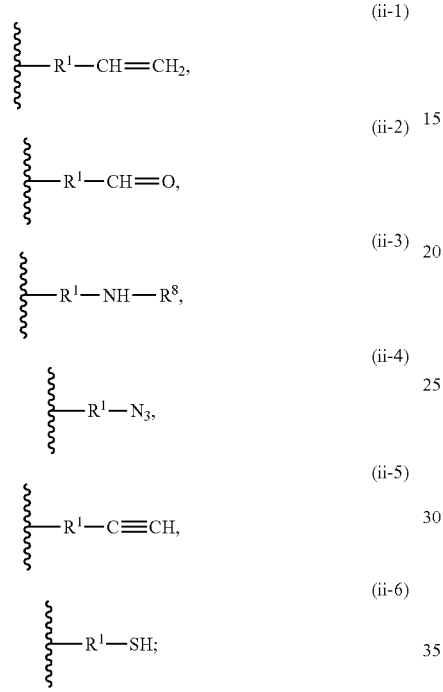

wherein $R^1$ is independently a single bond or a divalent hydrocarbon group having 1 to 6 carbon atoms, each —$CH_2$— of the divalent hydrocarbon group is unsubstituted or substituted by —O—, —NH— or —CO—, and $R^8$ is a protecting group or H.

17. The method of claim 16, wherein the first chemical handle has the structure represented by Formula (ii-1-1), Formula (ii-2-1), Formula (ii-3-1) or Formula (ii-5-1):

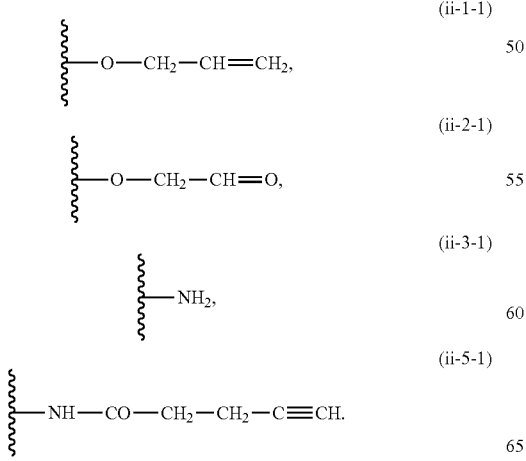

18. The method of claim 10, wherein at least one connector has the structure represented by Formula (iii-1):

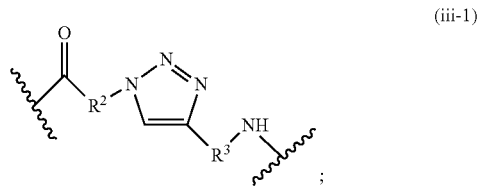

wherein $R^2$ and $R^3$ are independently a single bond or a divalent hydrocarbon group having 1 to 6 carbon atoms.

19. A protein modulator, comprising:
a polygonal scaffold, comprising:
at least three PPII helix rods, wherein each of the PPII helix rods is composed of a plurality of repeat units represented by Formula (i):

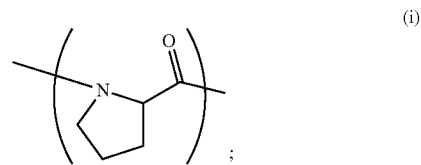

wherein at least one of the PPII helix rods has at least one hydrogen atom of at least one of the repeat units being substituted by a linker; and
at least three connectors, wherein each of the connectors is a divalent organic group, and each PPII helix rod is connected by two connectors to two other PPII helix rods to form a closed ring; and
at least one ligand, wherein the ligand is connected with one of the PPII helix rods through the linker.

20. The protein modulator of claim 19, wherein the linker has a structure represented by Formula (vi-1), Formula (vi-2) or Formula (vi-3):

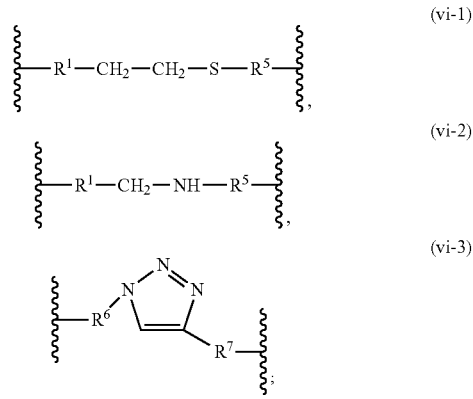

wherein $R^1$, $R^5$, $R^6$ and $R^7$ are independently a single bond or a divalent hydrocarbon group having 1 to 6 carbon atoms, and each —$CH_2$— of the divalent hydrocarbon group is unsubstituted or substituted by —O—, —NH— or —CO—.

21. The protein modulator of claim 19, wherein at least one connector has a structure represented by Formula (iii-1):

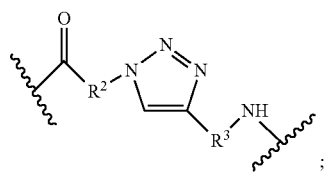
(iii-1)
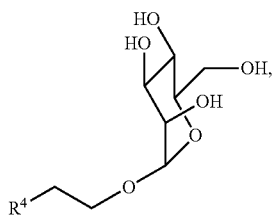
wherein $R^2$ and $R^3$ are independently a single bond or a divalent hydrocarbon group having 1 to 6 carbon atoms.
22. The protein modulator of claim 19, wherein the ligand has a structure represented by Formula (iv-1-1), Formula (iv-2-1), Formula (iv-3-1), Formula (iv-4-1), Formula (iv-5-1), Formula (iv-6-1) or Formula (iv-7-1):
(iv-1)
(iv-2)
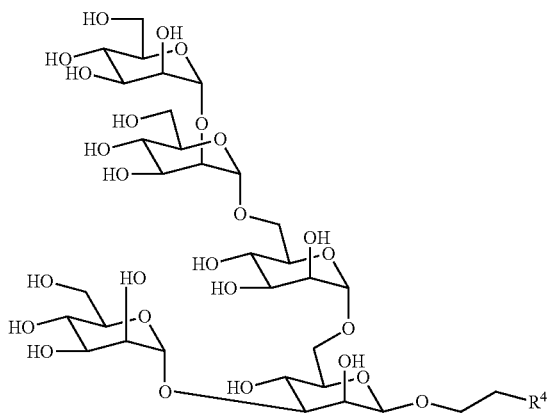
(iv-3)
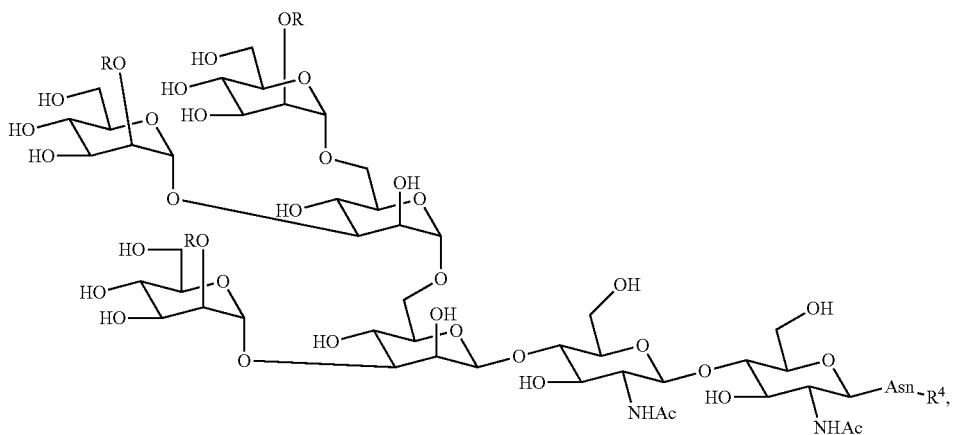
(iv-4)
(iv-5)
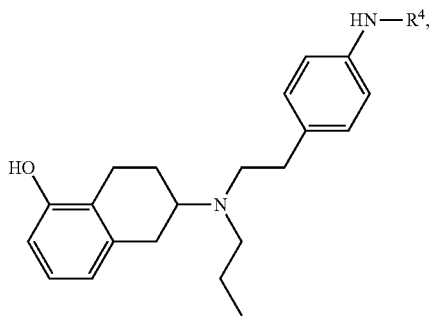
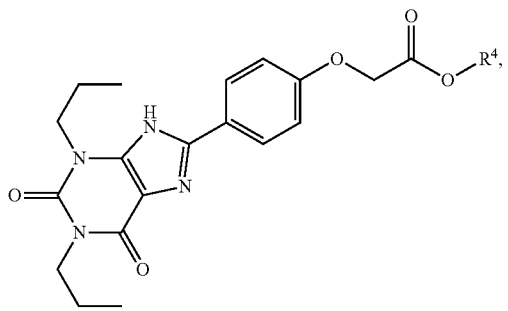

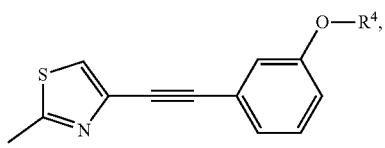 (iv-6)

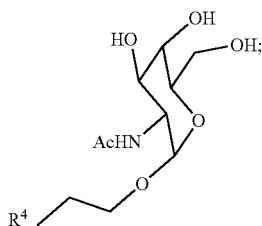 (iv-7)

wherein R is H or a 1-2 Man.

23. A method for manufacturing the protein modulator of claim 19, comprising:
providing a polygonal scaffold, wherein the polygonal scaffold comprises:
at least three PPII helix rods, wherein each of the PPII helix rods is composed of a plurality of repeat units represented by Formula (i):

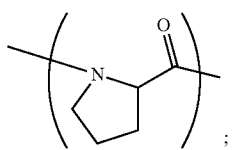 (i)

wherein at least one of the PPII helix rods has at least one hydrogen atom of at least one of the repeat units being substituted by a first chemical handle for connecting the ligand; and
at least three connectors, wherein each of the connectors is a divalent organic group, and each PPII helix rod is connected by two connectors to two other PPII helix rods to form a closed ring;
providing at least one ligand-providing compound, wherein the ligand-providing compound comprises the ligand and a second chemical handle, and the ligand is connected with the second chemical handle; and
providing a conjugation step, wherein the first chemical handle of the PPII helix rod is reacted with the second chemical handle of the ligand-providing compound to form the linker, thus the ligand is connected with one of the PPII helix rods through the linker.

24. The method of claim 23, wherein the conjugation step is conducted by a thiol-ene reaction, a coupling reaction, a reductive amination reaction or a CuAAC in solution-phase.

* * * * *